United States Patent [19]
Imai et al.

[11] Patent Number: 5,985,864
[45] Date of Patent: Nov. 16, 1999

[54] POLYMORPHS OF DONEPEZIL HYDROCHLORIDE AND PROCESS FOR PRODUCTION

[75] Inventors: Akio Imai; Hideaki Watanabe; Takashi Kajima; Yasushi Ishihama; Akiyo Ohtsuka; Tomohide Tanaka; Yukio Narabu, all of Ibaraki, Japan

[73] Assignee: Eisai Co., Ltd., Tokyo, Japan

[21] Appl. No.: 08/870,394

[22] Filed: Jun. 6, 1997

Related U.S. Application Data

[63] Continuation-in-part of application No. 08/794,802, Dec. 30, 1996.

[30] Foreign Application Priority Data

Jun. 7, 1996 [JP] Japan ...................................... 8-146293

[51] Int. Cl.⁶ .......................... A01N 43/40; A01N 43/46; C07D 211/20; C07D 207/00
[52] U.S. Cl. .......................... 514/212; 514/319; 514/321; 514/357; 514/408; 514/422; 514/429; 540/484; 540/596; 540/611; 540/612; 546/197; 546/206; 548/400; 548/526; 548/529
[58] Field of Search ...................................... 514/357, 212, 514/319, 321, 408, 422, 429; 540/484, 596, 611, 612; 546/197, 206; 548/400, 526, 528

[56] References Cited

U.S. PATENT DOCUMENTS 4,895,841  1/1990  Sugimoto et al. ...................... 514/212

FOREIGN PATENT DOCUMENTS 0296560  12/1988  European Pat. Off. .

OTHER PUBLICATIONS

Haleblian et al, Chemical Abstract, vol. 71 No. 105142, "Pharmaceutical Application of Polymorphism" (1969).
Sabon et al, Chemical Abstract, vol. 91 No. 112384, "Polymorphism and Solubility" (1979).
Brown, Chemical Abstract, vol. 73 No. 80415, "Pharmaceutical Reviews" (1970).

*Primary Examiner*—John Kight
*Assistant Examiner*—Raymond Covington
*Attorney, Agent, or Firm*—Birch, Stewart, Kolasch & Birch, LLP

[57] ABSTRACT

Donepezil hydrochloride, 1-benzyl-4-[(5,6-dimethoxy-1-indanon)-2-yl]methylpiperidine hydrochloride, is provided here in the form of four polymorphs which are stable against heat and humidity in the pharmaceutical use. They can be industrially produced. They are specified by peaks in X-ray powder diffraction pattern and absorption peaks in infrared absorption spectra in potassium bromide.

33 Claims, 36 Drawing Sheets

POLYMORPHS OF DONEPEZIL HYDROCHLORIDE AND PROCESS FOR PRODUCTION

This application is a continuation-in-part of application Ser. No. 08/794,802 filed on Dec. 30, 1996, the entire contents of which are hereby incorporated by reference.

FIELD OF THE INVENTION

The present invention relates to the stable polymorphs of Donepezil hydrochloride, that is, 1-benzyl-4-[(5,6-dimethoxy-1-indanon)-2-yl]methyl-piperidine hydrochloride, disclosed in the example 4 of U.S. Pat. No. 4,895,841 or EP-A 296560, having an excellent efficacy as pharmaceuticals, and industrial processes for producing them.

BACKGROUND OF THE INVENTION

Donepezil hydrochloride shows the acetylcholine esterase-inhibitory action and is useful for the treatment of all kinds of senile dementia, in particular being useful for prevention, treatment and amelioration of Alzheimer Disease. Donepezil hydrochloride is administered orally as usual and it may be placed for distribution and storage in a period of time before the administration. It may then be stored at patient's home for about one month at the maximum because of the property of the target disease. The stability of this medicinal substance (bulk pharmaceutical chemicals) against heat and humidity during the storage period is very important. A more stable medicinal substance of Donepezil hydrochloride is, therefore, desired. It is not known, however, that polymorphs of Donepezil hydrochloride exist. No sufficiently stable medicinal substance of Donepezil hydrochloride has been found.

PRIOR ARTS

U.S. Pat. No. 4,895,841 discloses in Example 4 that recrystalization of the crude product mixture of Donepezil hydrochloride from ethanol/isopropyl ether afforded a purified Donepezil hydrochloride. If there is a more stable crystalline form of Donepezil hydrochloride for a long period, it is more practical for distribution and storage.

SUMMARY OF THE INVENTION

Regarding the foregoing problems, the present inventors have proceeded with extensive research. As a result, it has been found that novel polymorphs of Donepezil hydrochloride (I) to (IV) and (V) can be produced and have an excellent stability, establishing the present invention. The present invention offers the five forms or species of novel polymorphs of Donepezil hydrochloride and industrially excellent processes for producing them. In detail, the present invention relates to the five polymorphs (I) to (V) of Donepezil hydrochloride represented by the following chemical structure, the polymorphs being specified by the peaks appearing in the powder X-ray diffraction pattern and infrared absorption spectra in potassium bromide.

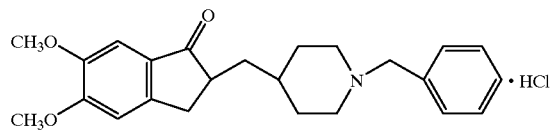

Method, and Condition of the Measurement of X-ray Diffraction Patterns (1) Method of the Measurement X-ray diffraction patterns were measured on each 100 mg of the samples by the following condition.

(2) Condition of the Measurement

| | |
|---|---|
| Target | Cu |
| Filter | monochro |
| Voltage | 40 KV |
| Current | 20 mA |
| Slit | DS 1, RS 0.15, SS 1 |
| Scan speed | 2 deg/min. |
| Range | 5–30 |
| Step/Sample | 0.02 deg |

Method and Condition of the Measurement of Infrared Absorption

Infrared absorption spectra in potassium bromide were measured according to the general method recorded in the Japanese Pharmacopoeia.

(1) Polymorphs (I)

Peaks in the powder X-ray diffraction pattern are:

| Diffraction angles (2θ, °) | Intensity (I/I$_0$) |
|---|---|
| 9.94 | 24 |
| 10.60 | 19 |
| 12.66 | 69 |
| 13.12 | 55 |
| 13.66 | 44 |
| 13.86 | 40 |
| 14.92 | 49 |
| 15.26 | 17 |
| 16.08 | 35 |
| 16.86 | 34 |
| 17.50 | 34 |
| 17.58 | 42 |
| 18.42 | 20 |
| 19.28 | 27 |
| 19.80 | 45 |
| 19.94 | 45 |
| 21.22 | 100 |
| 22.00 | 32 |
| 22.54 | 31 |
| 22.98 | 49 |
| 23.60 | 56 |
| 23.78 | 75 |
| 23.92 | 78 |
| 26.46 | 33 |
| 28.02 | 25 |
| 29.50 | 37. |

Wave numbers (cm$^{-1}$) of infrared absorption spectra in potassium bromide are:
463, 502, 563, 589, 604, 701, 750, 759, 799, 860, 922, 947, 972, 1012, 1038, 1104, 1120, 1128, 1175, 1192, 1218, 1250, 1267, 1316, 1368, 1410, 1433, 1440, 1455, 1472, 1502, 1591, 1606, 1644, 1684, 2412, 2530, 2559, 2595, 2620, 2717, 2840, 2858, 2924, 3004, 3074, 3259, 3373, 3547, 3589 cm$^{-1}$.

(2) Polymorphs (II)

Peaks in the powder X-ray diffraction pattern are:

| Diffraction angles (2θ, °) | Intensity (I/I$_0$) |
| --- | --- |
| 7.40 | 8 |
| 9.88 | 100 |
| 12.36 | 13 |
| 15.54 | 40 |
| 16.10 | 38 |
| 16.22 | 38 |
| 16.48 | 35 |
| 17.30 | 17 |
| 18.04 | 20 |
| 18.44 | 17 |
| 18.84 | 19 |
| 19.34 | 19 |
| 19.84 | 47 |
| 21.16 | 24 |
| 22.40 | 19 |
| 23.18 | 33 |
| 24.02 | 22 |
| 24.92 | 25 |
| 25.72 | 27 |
| 26.40 | 18 |
| 27.22 | 14. |

Wave numbers (cm$^{-1}$) of infrared absorption spectra in potassium bromide are:
699, 748, 762, 845, 947, 1009, 1035, 1067, 1103, 1118, 1129, 1174, 1193, 1206, 1222, 1247, 1267, 1317, 1365, 1422, 1436, 1456, 1465, 1502, 1592, 1607, 1688, 2412, 2489, 2627, 2846, 2868, 2913, 2928, 3435 cm$^{-1}$.

(3) Polymorphs (III)

Peaks in the powder X-ray diffraction pattern are:

| Diffraction angles (2θ, °) | Intensity (I/I$_0$) |
| --- | --- |
| 6.56 | 30 |
| 9.94 | 8 |
| 13.00 | 17 |
| 15.00 | 47 |
| 15.26 | 14 |
| 15.74 | 6 |
| 16.48 | 35 |
| 17.42 | 4 |
| 18.10 | 21 |
| 18.50 | 56 |
| 19.50 | 17 |
| 20.10 | 32 |
| 20.94 | 21 |
| 21.66 | 100 |
| 22.32 | 25 |
| 22.92 | 17 |
| 23.92 | 19 |
| 24.68 | 17 |
| 26.00 | 44 |
| 27.20 | 23 |
| 28.02 | 29 |
| 28.22 | 40 |
| 28.60 | 13. |

Wave numbers (cm$^{-1}$) of infrared absorption spectrum in potassium bromide are:
559, 641, 648, 702, 749, 765, 786, 807, 851, 872, 927, 949, 966, 975, 982, 1007, 1034, 1071, 1080, 1111, 1119, 1131, 1177, 1190, 1205, 1217, 1230, 1250, 1265, 1292, 1313, 1367, 1389, 1420, 1438, 1453, 1461, 1470, 1500, 1589, 1605, 1697, 2407, 2419, 2461, 2624, 2641, 2651, 2667, 2837, 2848, 2873, 2924, 2954, 2961, 2993, 3007, 3377, 3433 cm$^{-1}$.

(4) Polymorphs (IV)

Peaks in the powder X-ray diffraction pattern are:

| Diffraction angles (2θ, °) | Intensity (I/I$_0$) |
| --- | --- |
| 6.24 | 15 |
| 9.66 | 12 |
| 11.04 | 22 |
| 12.12 | 24 |
| 12.54 | 67 |
| 12.76 | 61 |
| 13.98 | 27 |
| 14.42 | 15 |
| 14.88 | 11 |
| 16.34 | 12 |
| 17.46 | 100 |
| 18.12 | 25 |
| 18.60 | 32 |
| 19.06 | 15 |
| 19.98 | 74 |
| 20.42 | 41 |
| 20.62 | 34 |
| 21.30 | 48 |
| 21.80 | 63 |
| 22.58 | 78 |
| 23.04 | 46 |
| 24.00 | 32 |
| 24.54 | 49 |
| 25.14 | 90 |
| 25.36 | 99 |
| 26.06 | 34 |
| 28.10 | 41 |
| 28.58 | 39 |
| 29.30 | 31 |
| 29.44 | 28. |

Wave numbers (cm$^{-1}$) of infrared absorption spectra in potassium bromide are:
401, 431, 459, 467, 490, 506, 518, 561, 586, 606, 631, 651, 709, 758, 766, 857, 944, 1009, 1041, 1106, 1119, 1132, 1213, 1225, 1265, 1304, 1318, 1429, 1458, 1470, 1500, 1589, 1605, 1630, 1647, 1683, 2562, 2577, 2608, 2634, 2689, 2717, 2836, 2924, 2949, 2989, 3007, 3032, 3061, 3322, 3376, 3422 cm$^{-1}$.

Additional Analysis Data of Polymorphs (I) to (V) are Represented as Following.

(1) Polymorphs (I)

Peaks in the powder X-ray diffraction pattern are:

| Diffraction angles (2θ, °) | Intensity (I/I$_0$) |
| --- | --- |
| 9.82 | 13 |
| 10.48 | 18 |
| 12.52 | 93 |
| 13.02 | 69 |
| 13.52 | 34 |
| 13.74 | 37 |
| 14.78 | 31 |
| 16.00 | 45 |
| 16.76 | 37 |
| 17.46 | 34 |
| 19.18 | 26 |
| 19.66 | 32 |
| 21.04 | 100 |
| 21.16 | 82 |
| 22.92 | 52 |
| 23.82 | 72 |
| 24.14 | 32. |

Wave numbers (cm$^{-1}$) of infrared absorption spectra in potassium bromide are:
562.7, 603.2, 700.4, 749.6, 798.1, 859.2, 896.0, 921.3, 946.3, 971.8, 1038.0, 1119.3, 1216.8, 1266.0, 1315.4, 1367.7, 1454.1, 1501.5, 1537.8, 1555.9, 1590.7, 1643.7, 1681.9, 2350.9, 2534.0, 2922.1, 3381.8, 3585.2 cm$^{-1}$.

(2) Polymorphs (II)

Peaks in the powder X-ray diffraction pattern are:

| Diffraction angles (2θ, °) | Intensity (I/I$_0$) |
|---|---|
| 10.10 | 76 |
| 12.64 | 14 |
| 15.74 | 85 |
| 15.82 | 86 |
| 16.20 | 100 |
| 16.46 | 87 |
| 17.40 | 50 |
| 17.50 | 48 |
| 17.88 | 31 |
| 18.36 | 28 |
| 18.58 | 51 |
| 18.66 | 46 |
| 19.48 | 42 |
| 20.18 | 81 |
| 20.80 | 36 |
| 22.26 | 45 |
| 23.38 | 86 |
| 23.52 | 59 |
| 24.06 | 34 |
| 24.32 | 55 |
| 25.14 | 44 |
| 25.44 | 50 |
| 25.72 | 39 |
| 25.96 | 35 |
| 26.14 | 25 |
| 28.06 | 25 |
| 28.20 | 34 |
| 28.38 | 34. |

Wave numbers (cm$^{-1}$) of infrared absorption spectra in potassium bromide are:
560.1, 698.9, 749.1, 846.2, 947.6, 1036.1, 1119.3, 1222.7, 1266.4, 1318.7, 1364.1, 1458.3, 1500.9, 1522.3, 1534.0, 1542.6, 1560.2, 1570.3, 1592.0, 1637.0, 1647.9, 1654.4, 1689.5, 1718.3, 1734.7, 1751.7, 1773.9, 1793.8, 1830.7, 1846.0, 1870.1, 2345.1, 2489.9, 2927.9, 3448.1 cm$^{-1}$.

(3) Polymorphs (III)

Peaks in the powder X-ray diffraction pattern are:

| Diffraction angles (2θ, °) | Intensity (I/I$_0$) |
|---|---|
| 6.48 | 21 |
| 9.84 | 7 |
| 12.96 | 19 |
| 14.94 | 45 |
| 15.20 | 13 |
| 16.44 | 31 |
| 18.04 | 20 |
| 18.46 | 55 |
| 19.44 | 17 |
| 20.02 | 30 |
| 20.86 | 20 |
| 21.02 | 13 |
| 21.58 | 100 |
| 22.22 | 23 |
| 22.90 | 15 |
| 23.92 | 13 |
| 24.64 | 15 |
| 25.92 | 40 |
| 26.18 | 17 |
| 27.14 | 21 |
| 28.14 | 37 |
| 28.56 | 11 |
| 29.94 | 12. |

Wave numbers (cm$^{-1}$) of infrared absorption spectrum in potassium bromide are:
558.3, 641.1, 702.4, 748.5, 765.0, 786.1, 807.3, 850.8, 872.0, 926.8, 974.9, 1034.1, 1071.5, 1111.6, 1190.1, 1216.6, 1265.4, 1291.9, 1312.9, 1364.4, 1420.2, 1438.1, 1458.8, 1499.1, 1522.2, 1542.6, 1560.1, 1570.2, 1589.1, 1638.8, 1647.8, 1654.3, 1697.3, 1718.1, 1734.5, 1751.4, 1773.7, 1793.5, 1845.8, 2345.3, 2461.6, 2924.2, 3447.9 cm$^{-1}$.

(4) Polymorphs (IV)

Peaks in the powder X-ray diffraction pattern are:

| Diffraction angles (θ, °) | Intensity (I/I$_0$) |
|---|---|
| 9.64 | 11 |
| 10.92 | 11 |
| 12.46 | 63 |
| 12.72 | 17 |
| 13.86 | 27 |
| 14.42 | 12 |
| 17.36 | 100 |
| 18.54 | 39 |
| 19.90 | 37 |
| 21.18 | 35 |
| 21.74 | 39 |
| 22.48 | 60 |
| 22.96 | 36 |
| 24.10 | 17 |
| 25.28 | 70 |
| 28.00 | 27 |
| 28.50 | 27. |

Wave numbers (cm$^{-1}$) of infrared absorption spectra in potassium bromide are:
561.5, 709.0, 766.2, 786.3, 804.9, 857.0, 944.3, 979.3, 1041.5, 1118.7, 1264.6, 1318.7, 1364.1, 1458.1, 1499.2, 1542.5, 1560.1, 1588.1, 1636.6, 1647.8, 1654.3, 1684.3, 1718.2, 1734.4, 1751.4, 1773.7, 1793.5, 1830.5, 1845.8, 1870.1, 2344.8, 2369.3, 2719.2, 2922.9, 3324.0 cm$^{-1}$.

(5) Polymorphs (V)

| Diffraction angles (2θ, °) | Intensity (I/I$_0$) |
|---|---|
| 6.58 | 7 |
| 6.86 | 27 |
| 10.12 | 32 |
| 12.54 | 33 |
| 12.90 | 43 |
| 13.64 | 64 |
| 15.58 | 27 |
| 17.22 | 69 |
| 18.44 | 72 |
| 18.96 | 19 |
| 19.30 | 25 |
| 19.64 | 19 |
| 19.74 | 25 |
| 20.30 | 19 |
| 20.46 | 17 |
| 21.10 | 15 |
| 21.96 | 100 |
| 22.24 | 32 |
| 24.22 | 63 |
| 24.66 | 96 |
| 25.36 | 60 |
| 26.14 | 15 |
| 26.82 | 44 |
| 27.52 | 24 |
| 27.96 | 15 |
| 28.20 | 49 |
| 29.58 | 13 |
| 29.66 | 17 |
| 29.76 | 17. |

Wave numbers (cm$^{-1}$) of infrared absorption spectra in potassium bromide are:
506.5, 559.7, 594.4, 698.0, 740.8, 805.1, 861.9, 948.5, 972.1, 1039.9, 1120.8, 1220.7, 1264.8, 1314.6, 1364.1, 1458.0, 1499.5, 1542.5, 1560.2, 1592.1, 1692.9, 2500.1, 2924.2, 2998.9, 3422.1 cm$^{-1}$.

Melting points of the novel Polymorphs (I) to (V) disclosed in the present invention are different from that of example 4 in U.S. Pat. No. 4,895,841.

A melting point in U.S. Pat. No. 4,895,841 is 211–212° C. (decomposition).

| | |
|---|---|
| Melting point of the polymorph (I): (decomposition), | 225–226° C. |
| Melting point of the polymorph (II): (decomposition), | 224–226° C. |
| Melting point of the polymorph (III): (decomposition), | 229–231° C. |
| Melting point of the polymorph (IV): (decomposition), | 226–228° C. |
| Melting point of the polymorph (V): (decomposition), | 218–220° C. |
| [Melting point of the amorphous form: (decomposition)]. | 220–222° C. |

Furthermore, the thermogravimetric and differential thermal analysis (TG-DTA) of the present polymorphs measured under the following condition show different patterns from the prior art. It is noted accordingly that their crystalline forms are completely different from the prior art.

Method and Condition of the Thermogravimetric and Differential Thermal Analysis (TG-DTA)

About 3 to 6 mg of Samples were taken and subjected to thermal analysis under the following condition.

| | |
|---|---|
| Reference | empty |
| Scan speed | 5° C./min. |
| Sampling | 0.7 sec. |
| Upper limit | 300° C. |
| Lower limit | Room temperature. |

Detailed processes for preparing the novel polymorphs are as follows. In these processes, "Donepezil" means a free base of the Donepezil hydrochloride, i.e., 1-benzyl-4-[(5,6-dimethoxy-1-indanon)-2-yl]methylpiperidine.
(1) Processes for Preparing the Polymorph (I) are:
(1-1) Recrystalization of Donepezil hydrochloride from methanol,
(1-2) Dissolving Donepezil hydrochloride in methanol, followed by addition of diethyl ether or diisopropyl ether,
(1-3) Dissolving Donepezil in methanol, followed by addition of hydrochloric acid or hydrogen chloride,
(1-4) Dissolving Donepezil in ethanol, followed by addition of diisopropyl ether, and hydrochloric acid or hydrogen chloride successively; or
(1-5) Dissolving Donepezil in ethanol, followed by addition of hydrochloric acid or hydrogen chloride, and diisopropyl ether successively, then filtration of the crystals immediately after separation.
Process (1-5) is preferred. This process is illustrated in Example 7.
(2) Processes for Preparing the Polymorph (II) are:
(2-1) Dissolving Donepezil hydrochloride in ethanol, followed by addition of diethyl ether or diisopropyl ether,
(2-2) Dissolving Donepezil hydrochloride in ethanol, followed by addition of diisopropyl ether, then filtration of the crystals after 10 to 30 minutes from the separation,
(2-3) Dissolving Donepezil and hydrochloric acid or hydrogen chloride in ethanol, followed by addition of diethyl ether,
(2-4) Dissolving Donepezil in ethanol, followed by addition of hydrochloric acid or hydrogen chloride, then concentration,
(2-5) Dissolving Donepezil in ethanol, followed by addition of hydrochloric acid or hydrogen chloride, and diisopropyl ether successively; or
(2-6) Dissolving Donepezil in ethanol, followed by addition of hydrochloric acid or hydrogen chloride, and diisopropyl ether successively, then filtration of the crystals after 10 to 60 minutes, preferably 10 to 30 minutes from the separation.
Process (2-6) is preferred. This process is illustrated in Example 14.
(3) Processes for Preparing the Polymorph (III) are:
(3-1) Dissolving Donepezil hydrochloride in ethanol, followed by addition of diethyl ether,
(3-2) Dissolving Donepezil hydrochloride in dichloromethane, followed by addition of n-hexane,
(3-3) Dissolving Donepezil in acetone, followed by addition of hydrochloric acid or hydrogen chloride,
(3-4) Dissolving Donepezil in ethyl acetate, followed by addition of hydrochloric acid or hydrogen chloride,
(3-5) Dissolving Donepezil in ethanol, followed by addition of hydrochloric acid or hydrogen chloride, then addition of at least one solvent selected from diethyl ether, diisopropyl ether and n-hexane,
(3-6) According to a process (3-5) wherein the selected solvent is diisopropyl ether, filtration of the crystals after 1 hour, preferably 2 hours, more preferably 6 hours from the separation; or
(3-7) Heating of the polymorph (I) or (II).
Processes (3-5) and (3-6) are preferred. These processes are illustrated, respectively, in Examples 23 and 18.
(4) A Process for Preparing the Polymorph (IV) is:
(4-1) Humidification of the polymorph (II).
Process (4-1) is illustrated in Example 24.

The aforementioned processes (1-5), (2-6) and (3-6) comprise dissolving Donepezil in ethanol, followed by addition of hydrochloric acid or hydrogen chloride, and then adding diisopropyl ether. Anyone of these processes can produce polymorph (I), (II) or (III) by controlling an interval in time taken from recrystallization to isolation of crystals by filtration. These time lag may differ by the crystallization conditions, such as temperature, stirring velocity and a volume of a solvent. The following may be usually used.
(1) Filtration of the crystals immediately after separation affords the polymorph (I).
(2) Filtration of the crystals after 10 to 60 minutes, preferably 10 to 30 minutes from the separation affords the polymorph (II).
(3) Filtration of the crystals after 1 hour, preferably 2 hours, more preferably 6 hours from the separation affords the polymorph (III).

Further Detailed processes for preparing the novel polymorphs are as follows.
(1) Processes for Preparing the Polymorph (I) are:
(1-6) Dissolving Donepezil in methanol, followed by addition of hydrochloric acid or hydrogen chloride,
(1-7) Dissolving Donepezil in methanol, followed by addition of hydrochloric acid or hydrogen chloride and addition of tert-butyl methyl ether, diisopropyl ether or ethyl acetate successively,
(1-8) Dissolving Donepezil in ethanol, tetrahydrofuran or acetonitrile, followed by addition of hydrochloric acid or hydrogen chloride,
(1-9) Dissolving Donepezil hydrochloride in methanol, followed by addition of tert-butyl methyl ether, ethyl acetate or n-hexane,
(1-10) Recrystalization of Donepezil hydrochloride from ethanol; or (1-11) Dissolving Donepezil hydrochloride in ethanol, followed by addition of tert-butyl methyl ether.

Process (1-7) is preferred. This process is illustrated in Example 30, 31 and 32.

Process (1-9) is also preferred. This process is illustrated in Example 39, 40 and 41.

(2) Processes for preparing the polymorph (II) are:
(2-7) Dissolving Donepezil in ethanol, followed by addition of hydrochloric acid or hydrogen chloride and addition of tert-butyl methyl ether successively,
(2-8) Dissolving Donepezil in isopropyl alcohol, acetone or tetrahydrofran, followed by addition of hydrochloric acid or hydrogen chloride,
(2-9) Dissolving Donepezil in methylene chloride, followed by addition of hydrochloric acid or hydrogen chloride and addition of diisopropyl other successively,
(2-10) Dissolving Donepezil hydrochloride in ethanol, followed by addition of tert-butyl methyl ether or diisopropyl ether and stirring blow 10° C.,
(2-11) Dissolving Donepezil hydrochloride in methylene chloride, followed by addition of tert-butyl methyl ether or diisopropyl ether; or
(2-12) Heating the polymorph (I) or amorphous form of Donepezil hydrochloride.

Process (2-7) is preferred. This process is illustrated in Example 45.

Process (2-10) is also preferred. This process is illustrated in Example 52, 53 and 54.

(3) Processes for Preparing the Polymorph (III) are:
(3-8) Dissolving Donepezil in methanol, followed by addition of hydrochloric acid or hydrogen chloride and addition of acetone successively,
(3-9) Dissolving Donepezil in ethanol, followed by addition of hydrochloric acid or hydrogen chloride and addition of tert-butyl methyl other successively,
(3-10) Dissolving Donepezil in acetonitrile, acetone, a mixture of acetone and water, tetrahydrofuran or N,N-dimethylformamide, followed by addition of hydrochloric acid or hydrogen chloride,
(3-11) Dissolving Donepezil in ethyl acetate, followed by addition of hydrochloric acid or hydrogen chloride and addition of tert-butyl methyl other successively,
(3-12) Dissolving Donepezil in dimethylsulfoxide, followed by addition of hydrochloric acid or hydrogen chloride and addition of tert-butyl methyl other successively,
(3-13) Disolving Donepezil in toluene, followed by addition of hydrochloric acid or hydrogen chloride,
(3-14) Recrystalization of Donepezil hydrochloride from methanol not lower than 10° C.,
(3-15) Dissolving Donepezil hydrochloride in methanol, followed by addition of tert-butyl methyl ether or acetonitrile,
(3-16) Dissolving Donepezil hydrochloride in ethanol, followed by addition of tert-butyl methyl ether or acetonitrile and stirring not lower than 10° C.,
(3-17) Dissolving Donepezil hydrochloride in N,N-dimethylformamide or dimethylsulfoxide, followed by addition of tert-butyl methyl ether,
(3-18) Recrystalization of Donepezil hydrochloride from isopropyl alcohol,
(3-19) Conversion of polymorph (I), (II), (IV), (V) or amorphous form of Donepezil hydrochloride in solvent; or
(3-20) According to a process (3-19) wherein the solvent is selected from methanol, ethanol, ethyl acetate or acetone.

Process (3-11) is preferred. This process is illustrated in Examples 59.

Process (3-16) is also preferred. This process is illustrated in Examples 72.

Process (3-19) is also preferred. This process is illustrated in Examples 76 to 95.

(4) A Process for Preparing the Polymorph (IV) are:
(4-2) Dissolving Donepezil in hydrochloric acid, followed by filtration of the separated crystals,
(4-3) Dissolving Donepezil in hydrochloric acid, followed by addition of tetrahydrofuran,
(4-4) Dissolving Donepezil in a mixture of water and tetrahydrofuran, followed by addition of hydrochloric acid or hydrogen chloride,
(4-5) Dissolving Donepezil in methanol, toluene or n-hexane, followed by addition of hydrochloric acid,
(4-6) Dissolving Donepezil in a mixture of methanol and hydrochloric acid,
(4-7) Dissolving Donepezil in water, followed by addition of hydrochloric acid or hydrogen chloride,
(4-8) Recrystalization of Donepezil hydrochloride from water,
(4-9) Humidification of the polymorph (II) of Donepezil hydrochloride; or
(4-10) Humidification of the amorphous form of Donepezil hydrochloride.

Process (4-4) is preferred. This process is illustrated in Example 101.

Process (4-8) is also preferred. This process is illustrated in Example 106.

(5) A Process for Preparing the Polymorph (V) is:
(5-1) Heating the polymorph (IV) of Donepezil hydrochloride.

Process (5-1) is illustrated in Example 109.

In the aforementioned process (3-6) for obtaining the polymorph (III), comprising from dissolving Donepezil in ethanol, followed by addition of hydrochloric acid or hydrogen chloride, and then adding diisopropyl ether, the preferred crystallization time depends on stirring velocity, volume of solvent e.t.c. However, higher temperature shortens the crystallization time. These changes are illustrated in Example 96 to 98.

The invention provides a method for treating a disease accompanied by acetylcholinesterase activity by administering to a human patient a pharmacologically effective amount of the Donepezil hydrochloride in the form of polymorph as above for inhibiting the acetylcholinesterase activity.

The invention further provides a therapeutical composition which comprises a pharmacologically effective amount of Donepezil hydrochloride in the form of polymorph as above and a pharmacologically acceptable carrier.

The compound in the form of polymorph of the present invention is effective for treatment, prevention, remission, improvement, etc. of various kinds of senile dementia, particularly senile dementia of the Alzheimer type; cerebrovascular diseases accompanying cerebral apoplexy, e.g. cerebral hemorrhage or cerebral infarcts, cerebral arteriosclerosis, head injury, etc.; and aprosexia, disturbance of speech, hypobulia, emotional changes, attention deficit/hyperactivity disorder, recent memory disturbance, hallucinatory-paranoid syndrome, behavioral changes, etc. accompanying encephalitis, cerebral palsy, etc.

Further, the compound in the form of polymorph of the present invention has a strong and highly selective acetylcholinesterase action, which renders the compound of the present invention useful also as a pharmaceutical based on this kind of action.

Specifically, the compound in the form of polymorph of the present invention is effective for, for example, Huntington's chorea, Pick's disease and delayed ataxia or tardive dyskinesia other than senile dementia of the Alzheimer type.

When the compound in the form of polymorph of the present invention is used as a pharmaceutical for these diseases, it may be orally or parenterally administered. In general, it is parenterally administered in the form of injections, such as intravenous, subcutaneous, and intramuscular injections, suppositories, or sublingual tablets. The dose will remarkably vary depending upon the symptom; age, sex, weight, and sensitivity of patients; method of administration; time and intervals of administration and properties, dispensing, and kind of pharmaceutical preparations; kind of effective ingredients, etc., so that there is no particular limitation with respect to the dose. Normally the compound may be administered in a dose of about 1.0 to 300 mg, preferably 1 to 100 mg, per day per adult, ordinarily in one to four portions.

Pharmaceutical preparations in the dosage form of, e.g., injections, suppositories, sublingual tablets, tablets, and capsules are prepared according to a method which is commonly accepted in the art.

In preparing injections, the effective ingredient is blended, if necessary, with a pH modifier, a buffer, a suspending agent, a solubilizing agent, a stabilizer, a tonicity agent, a preservative, etc., followed by preparation of an intravenous, subcutaneous, or intramuscular injection according to an ordinary method. In this case, if necessary, it is possible to lyophilize these preparations according to an ordinary method.

Examples of the suspending agents include methylcellulose, Polysorbate 80, hydroxyethylcellulose, acacia, powdered tragacanth, sodium carboxymethylcellulose, and polyoxyethylene sorbitan monolaurate.

Examples of the solubility agent include polyoxyethylene hydrogenated castor oil, Polysorbate 80, nicotinamide, polyoxyethylene sorbitan monolaurate, Macrogol, and an ethyl ester of castor oil fatty acid.

Examples of the stabilizer include sodium sulfite, sodium metasulfite and ether, and examples of the preservative include methyl p-hydroxybenzoate, ethyl p-hydroxybenzoate, sorbic acid, phenol, cresol, and chlorocresol.

Figure 1:
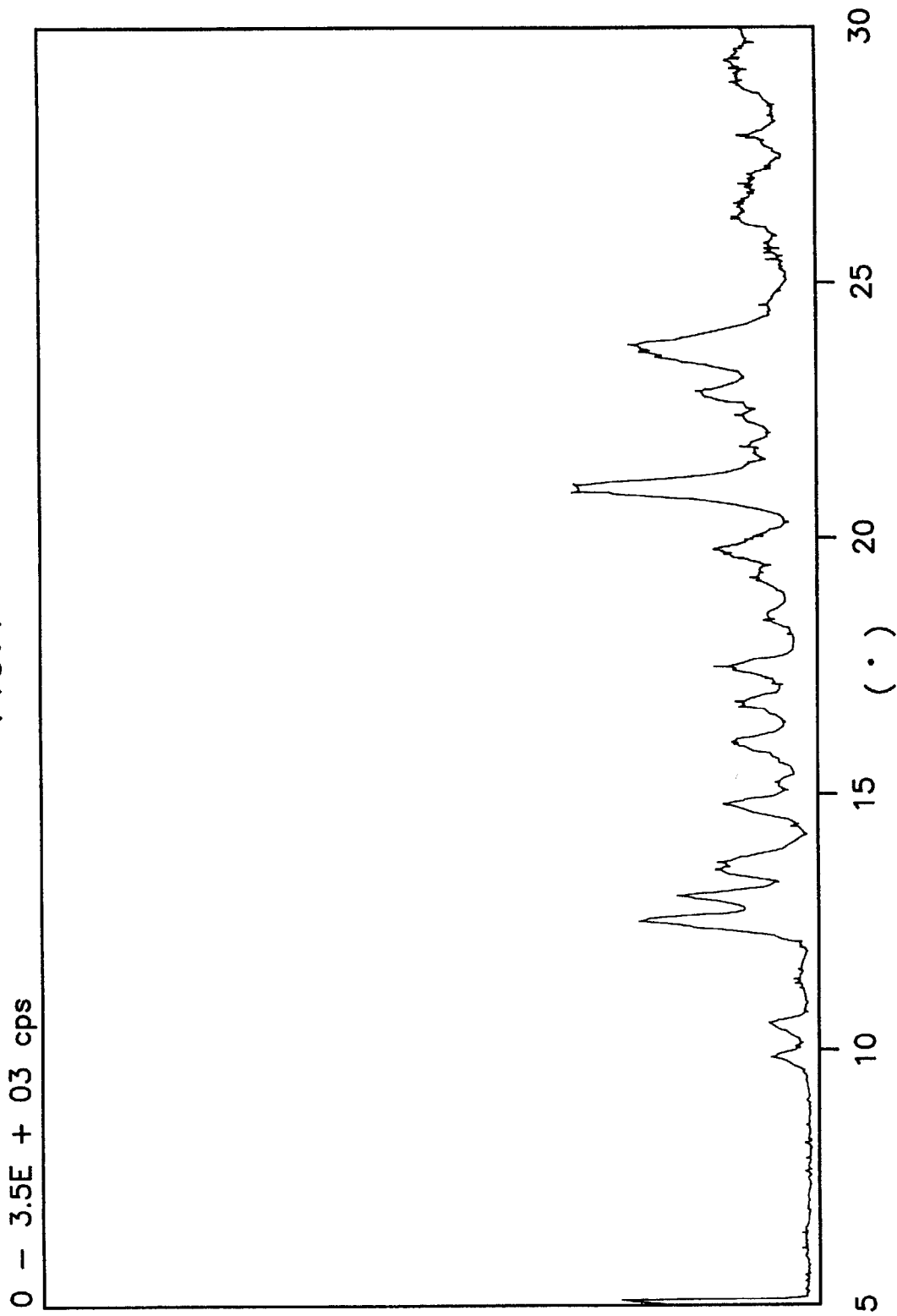
FIG. 1 is powder X-ray diffraction pattern of the polymorph (I).
Figure 2:
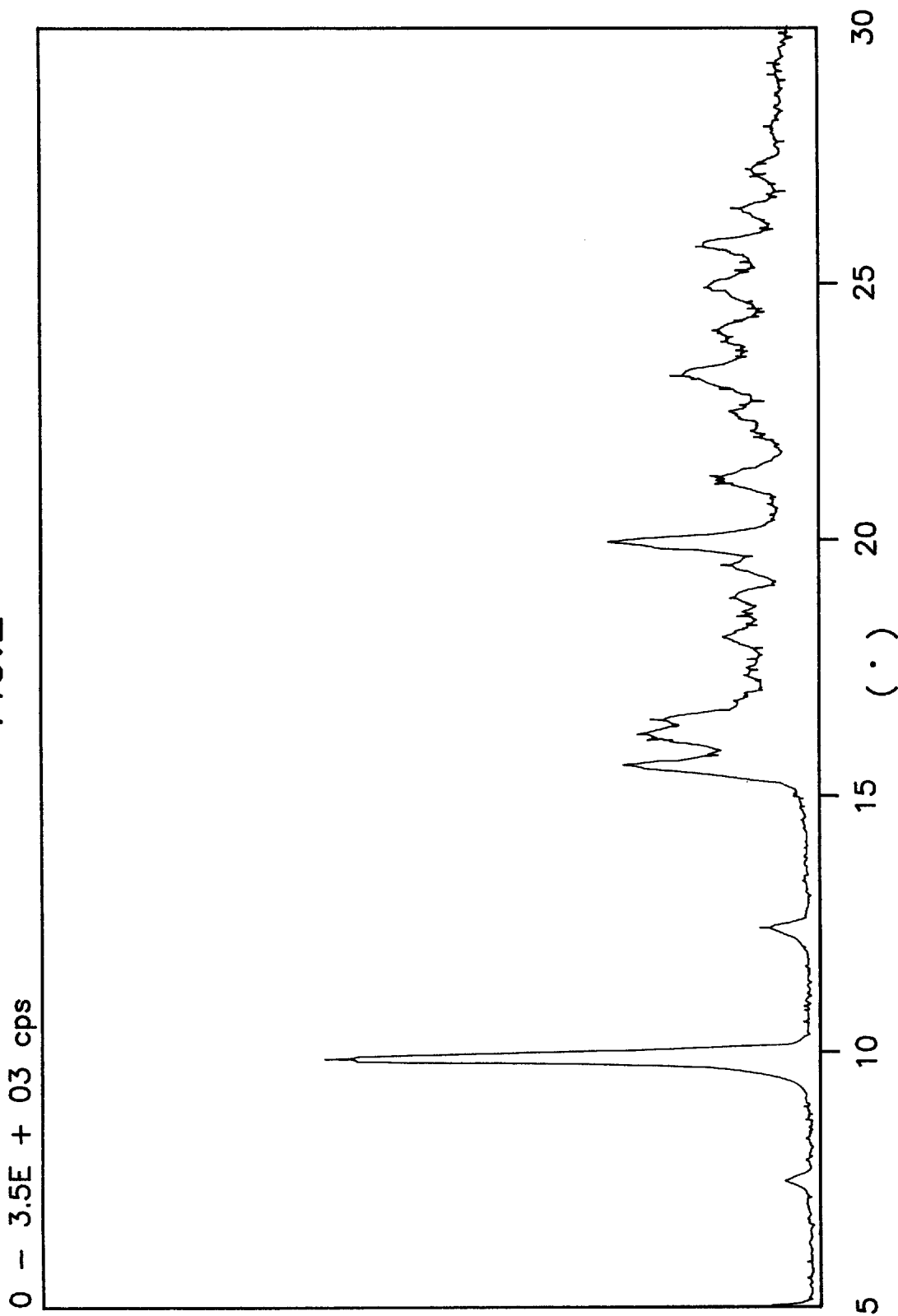
FIG. 2 is powder X-ray diffraction pattern of the polymorph (II).
Figure 3:
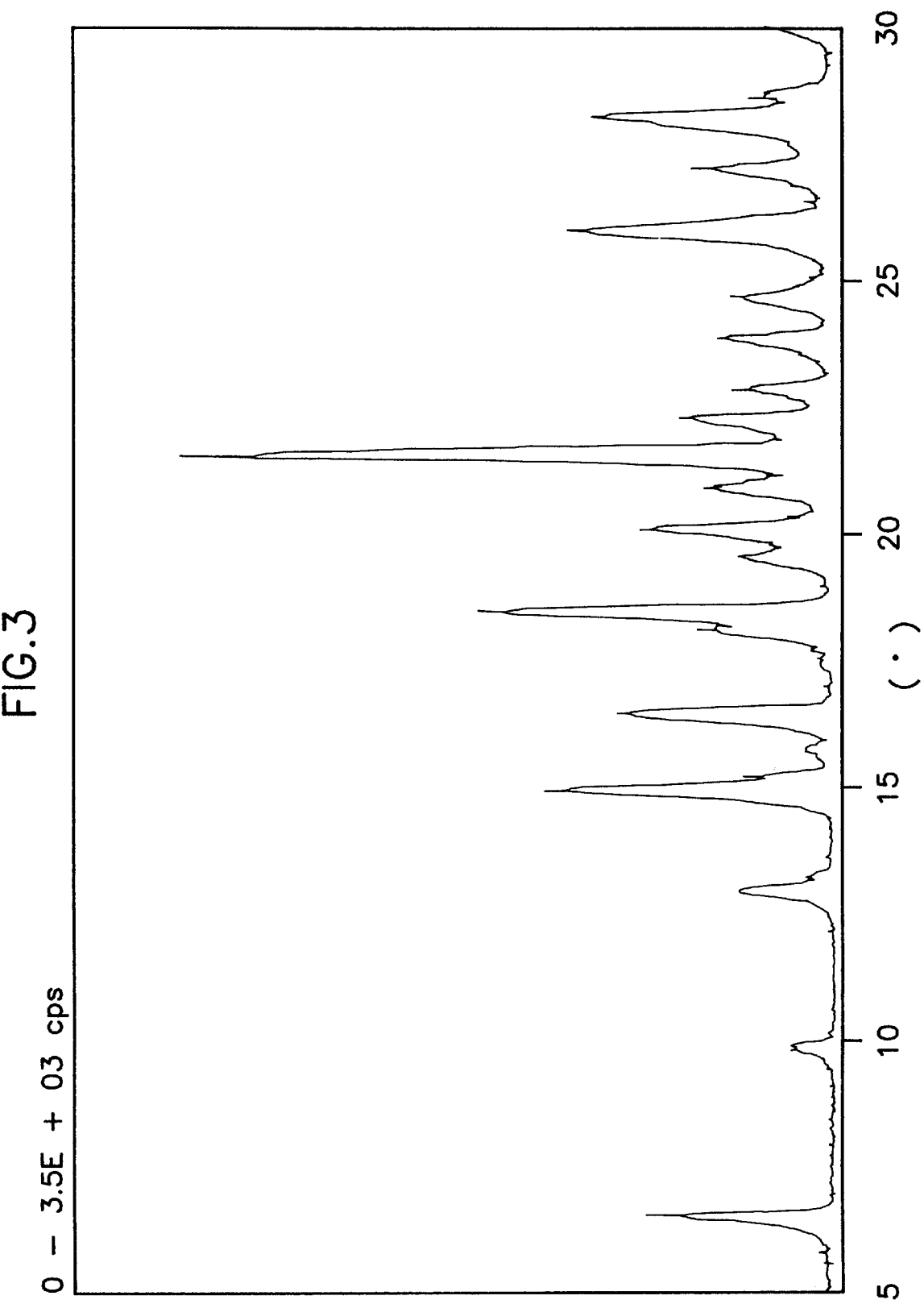
FIG. 3 is powder X-ray diffraction pattern of the polymorph (III).
Figure 4:
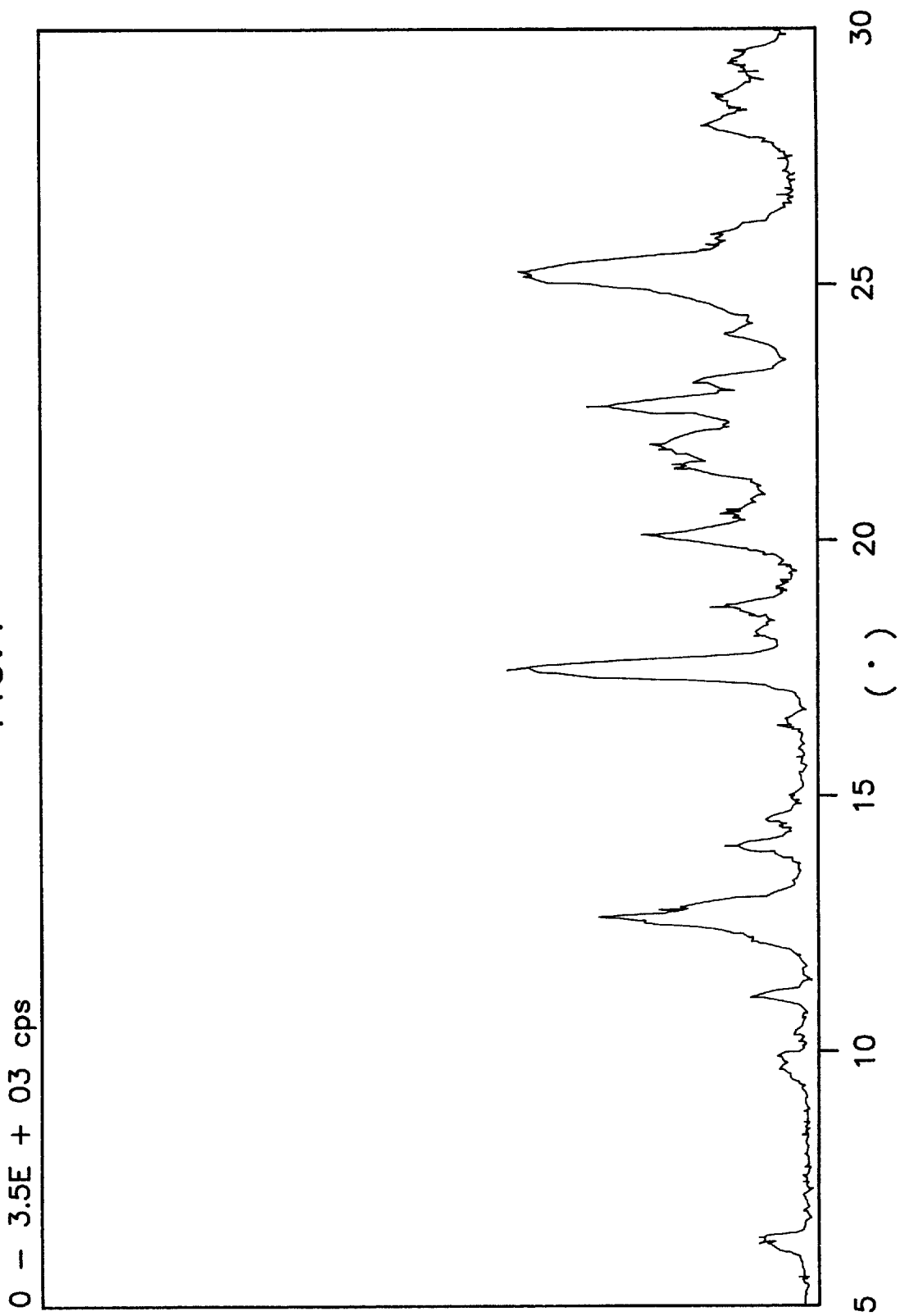
FIG. 4 is powder X-ray diffraction pattern of the polymorph (IV).
Figure 5:
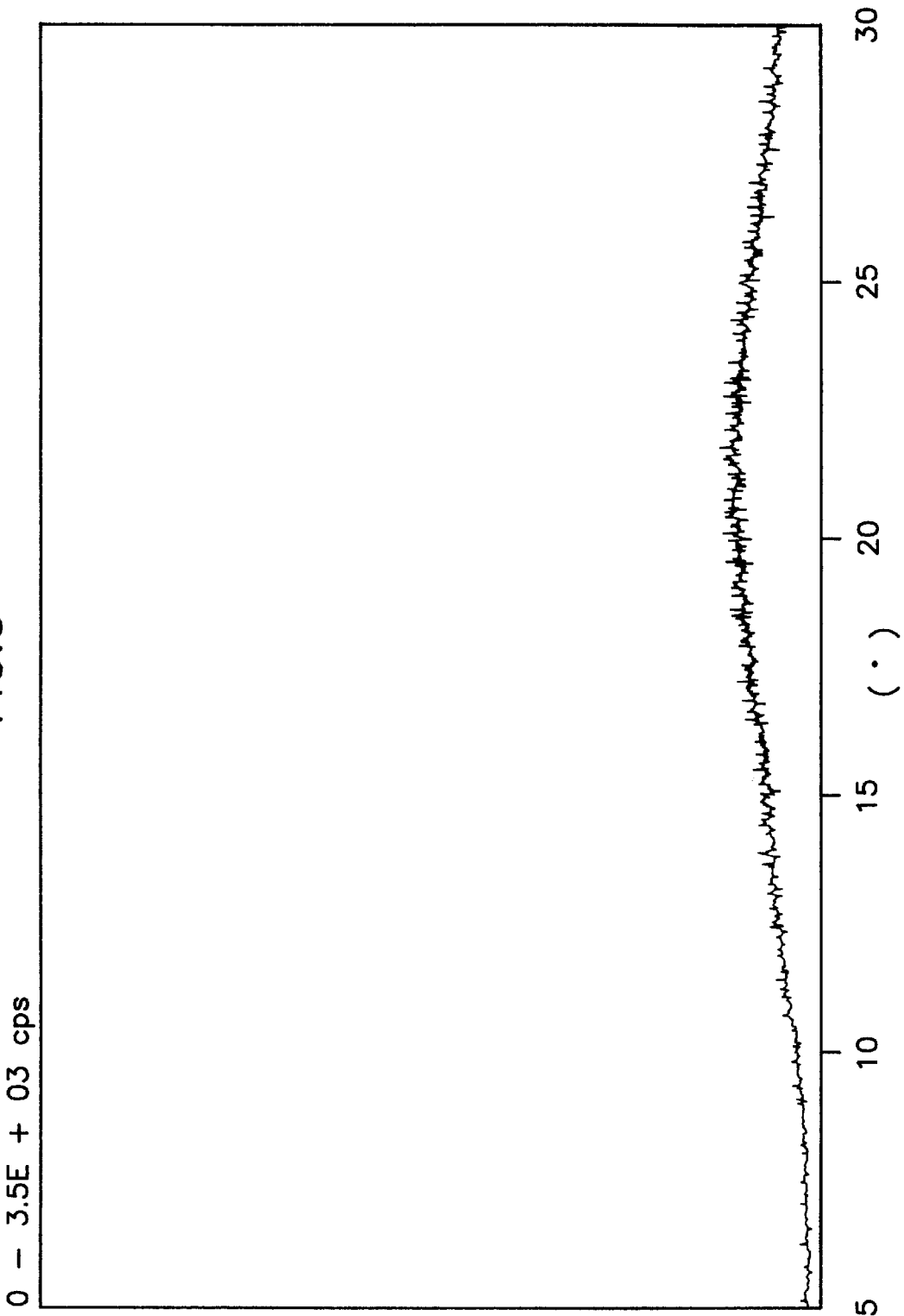
FIG. 5 is powder X-ray diffraction pattern of the Amorphous form.
Figure 6:
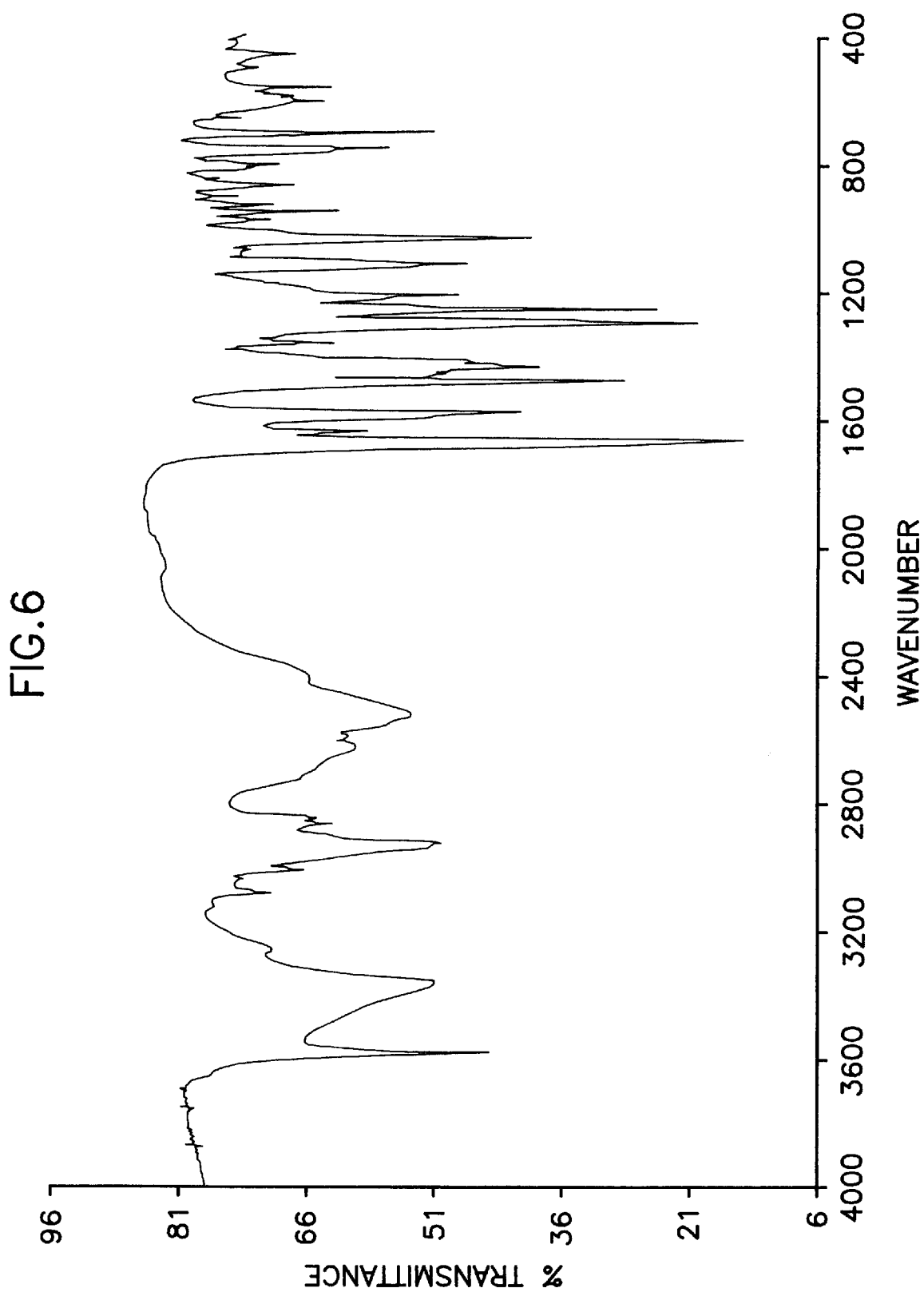
FIG. 6 is infrared absorption in potassium bromide of the polymorph (I).
Figure 7:
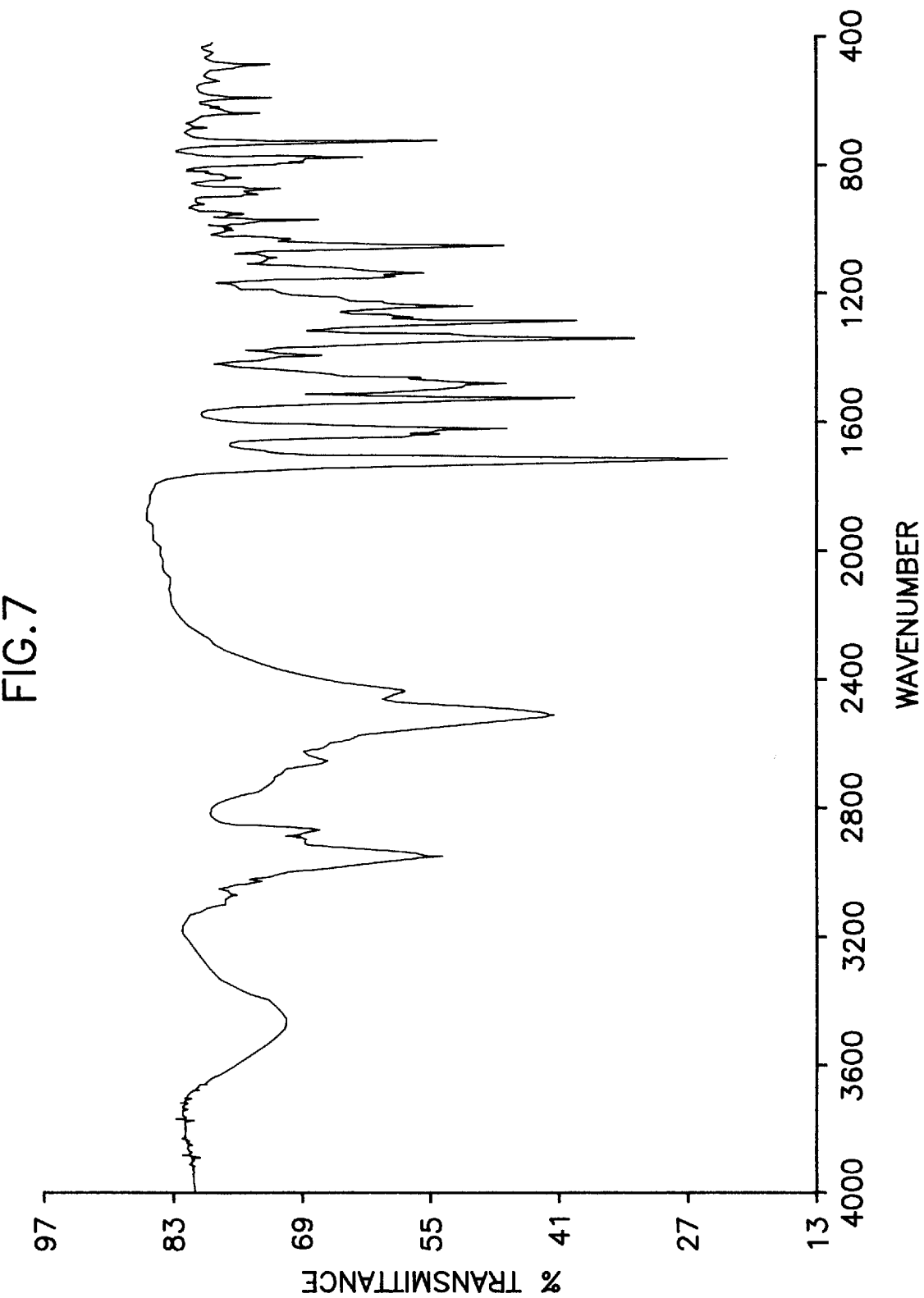
FIG. 7 is infrared absorption in potassium bromide of the polymorph (II).
Figure 8:
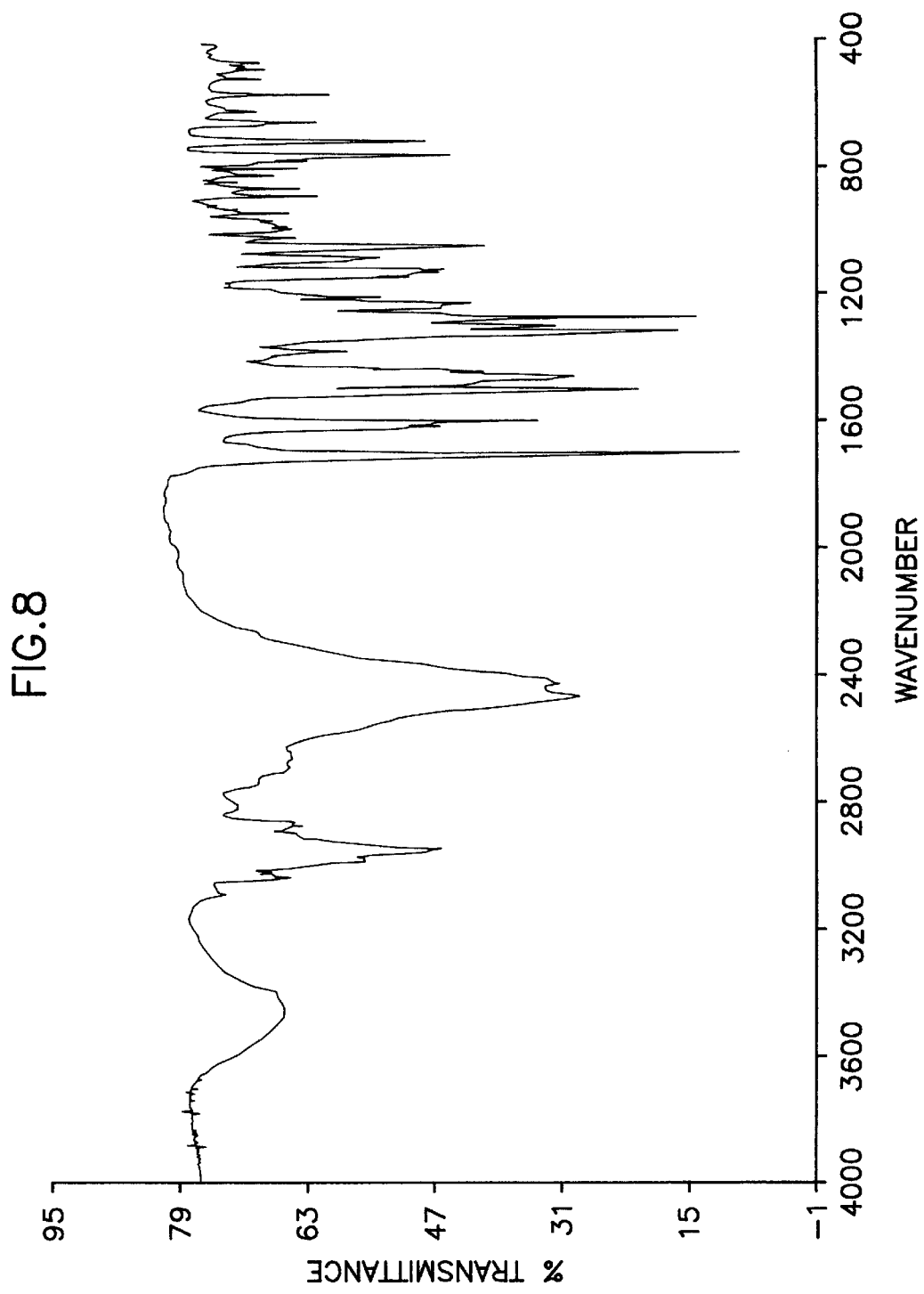
FIG. 8 is infrared absorption in potassium bromide of the polymorph (III).
Figure 9:
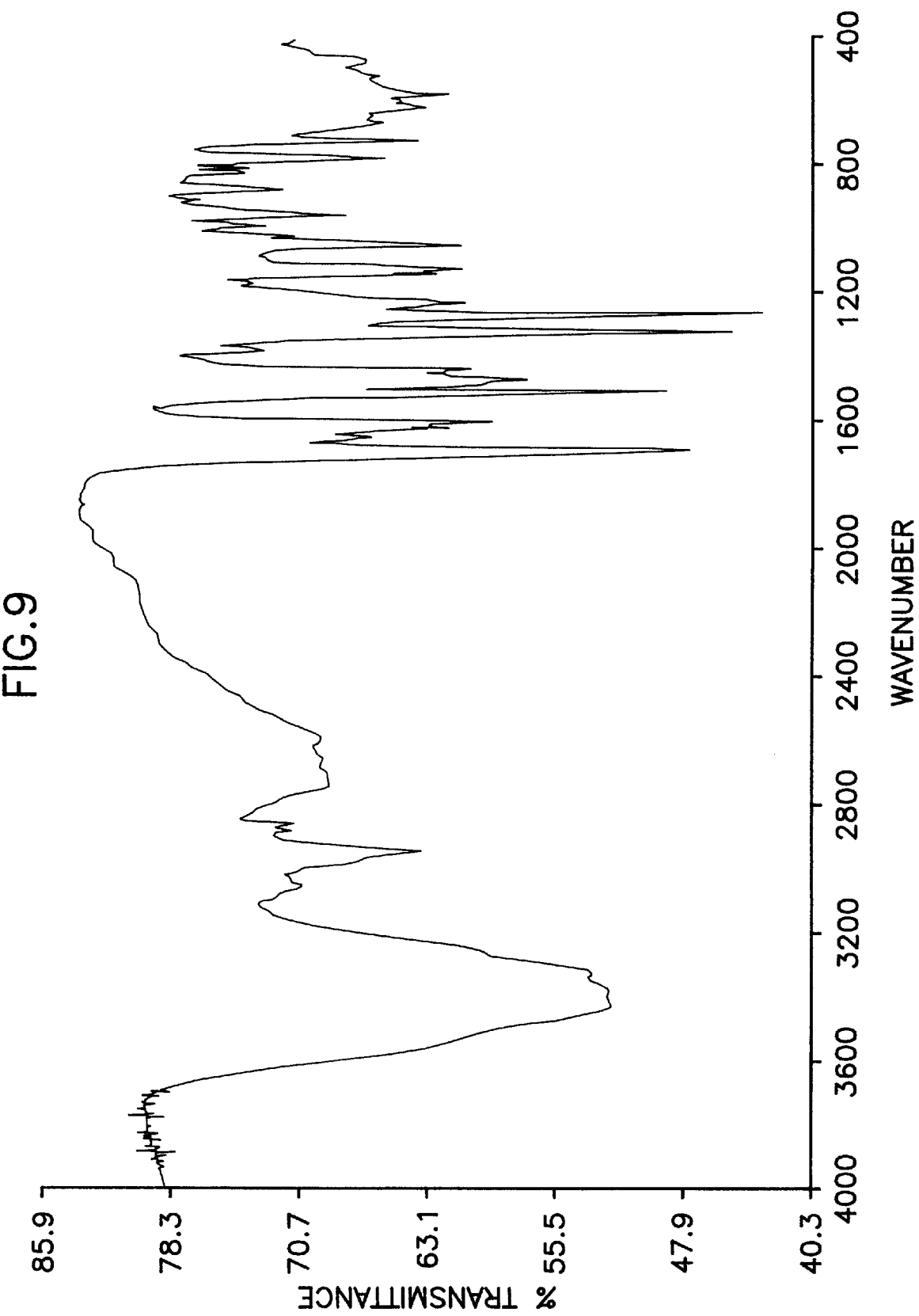
FIG. 9 is infrared absorption in potassium bromide of the polymorph (IV).
Figure 10:
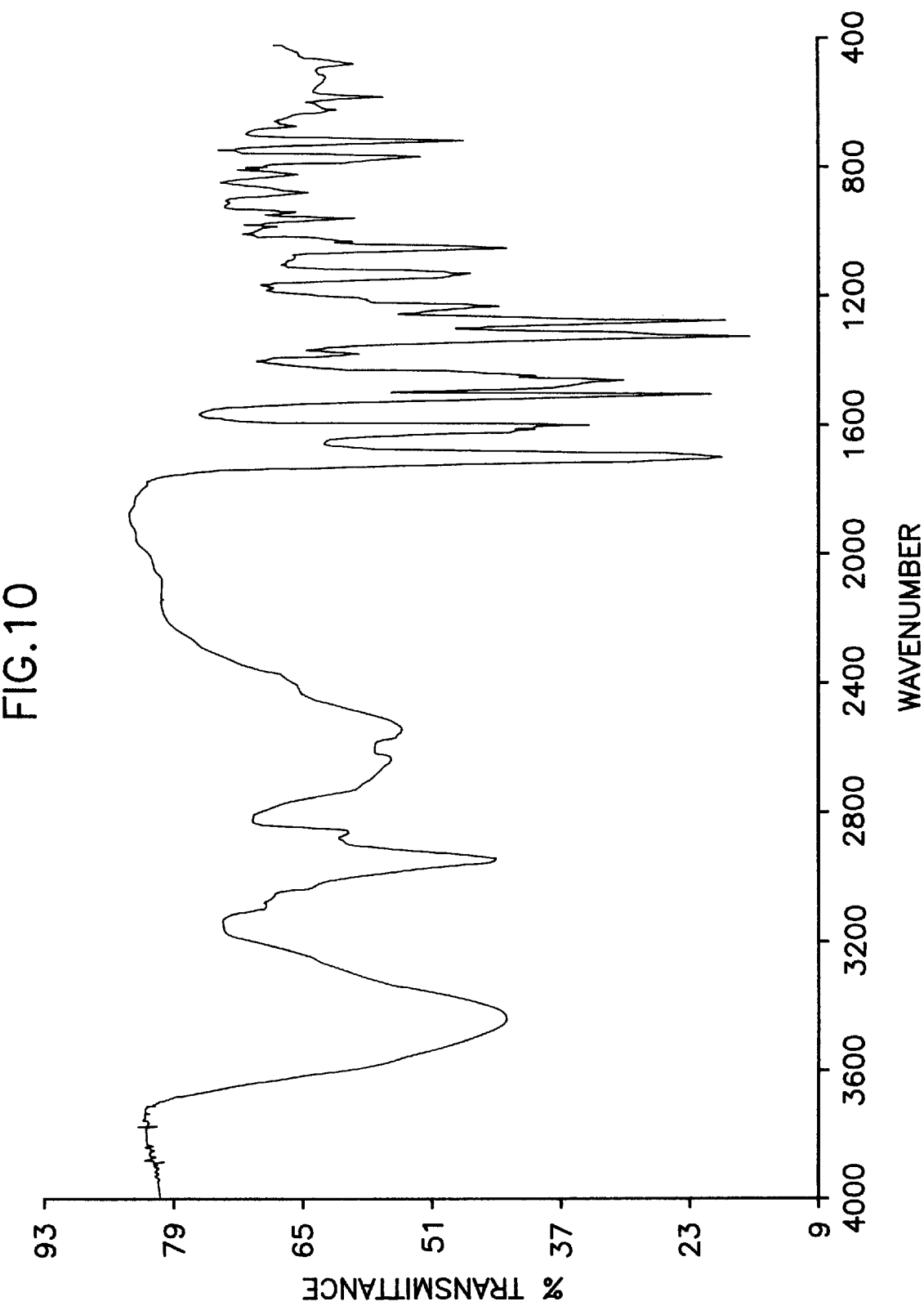
FIG. 10 is infrared absorption in potassium bromide of the amorphous form.
Figure 11:
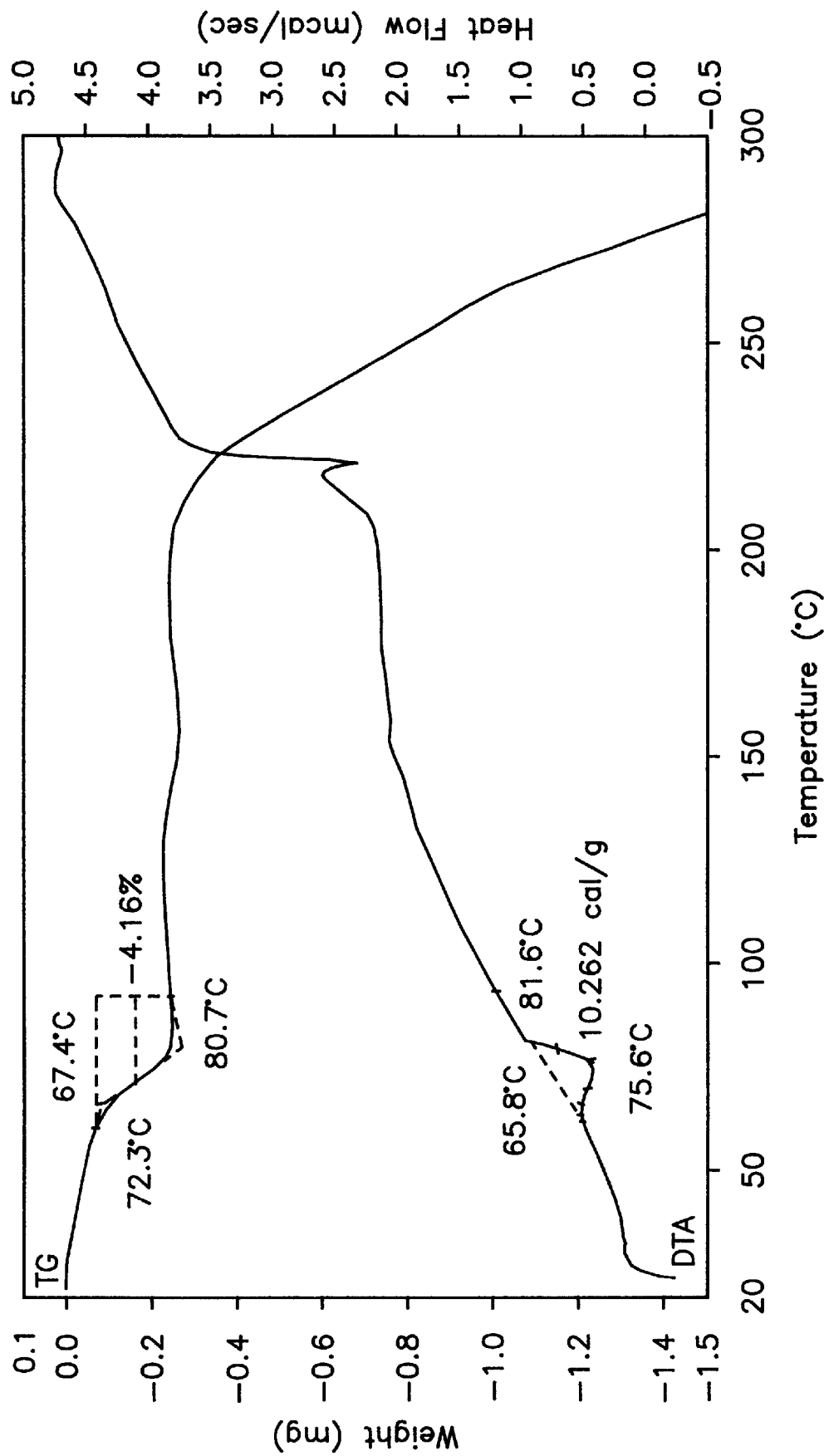
FIG. 11 is thermogravimetric and differential thermal analysis (TG-DTA) of the polymorph (I).
Figure 12:
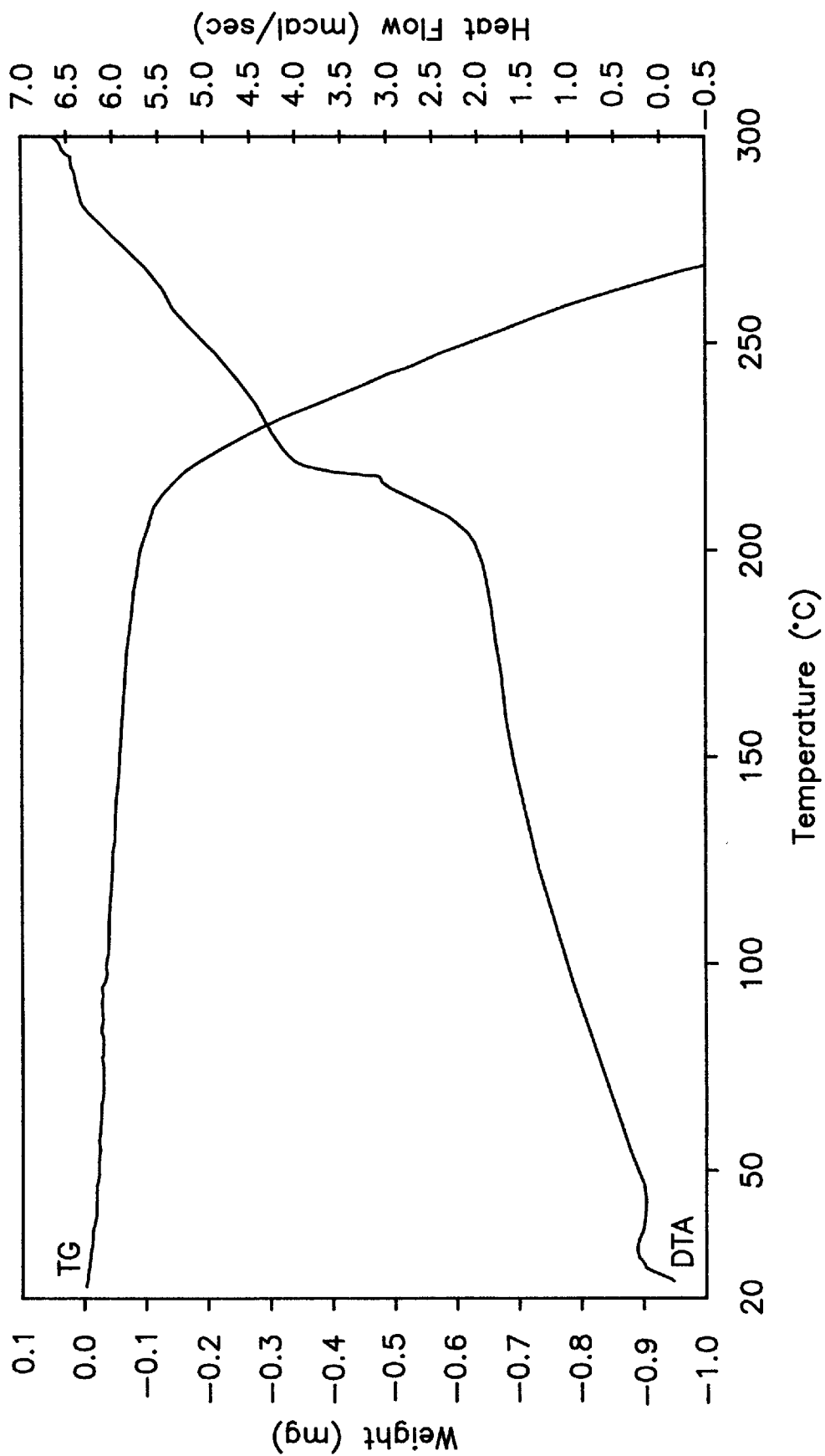
FIG. 12 is thermogravimetric and differential thermal analysis (TG-DTA) of the polymorph (II).
Figure 13:
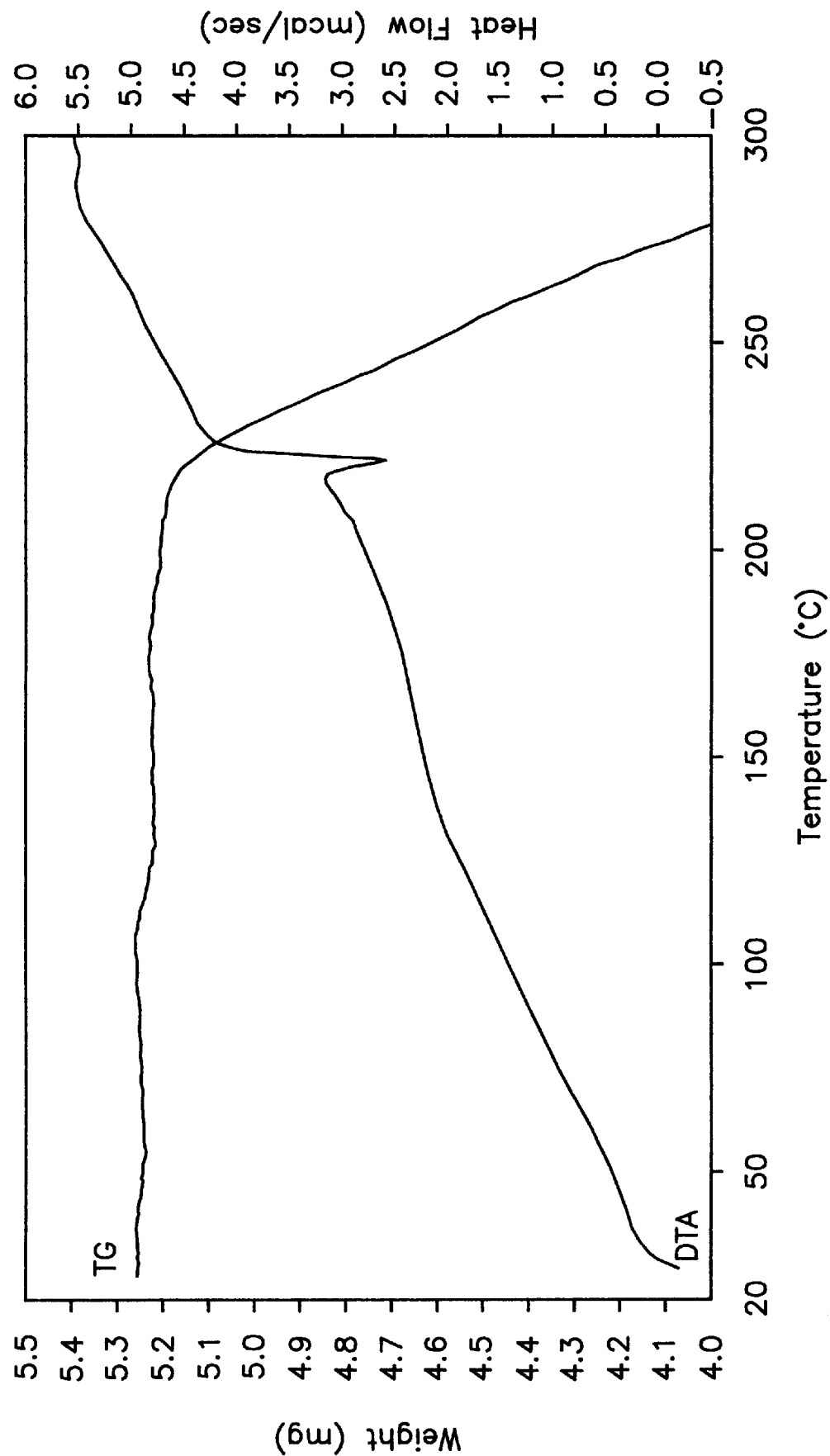
FIG. 13 is thermogravimetric and differential thermal analysis (TG-DTA) of the polymorph (III).
Figure 14:
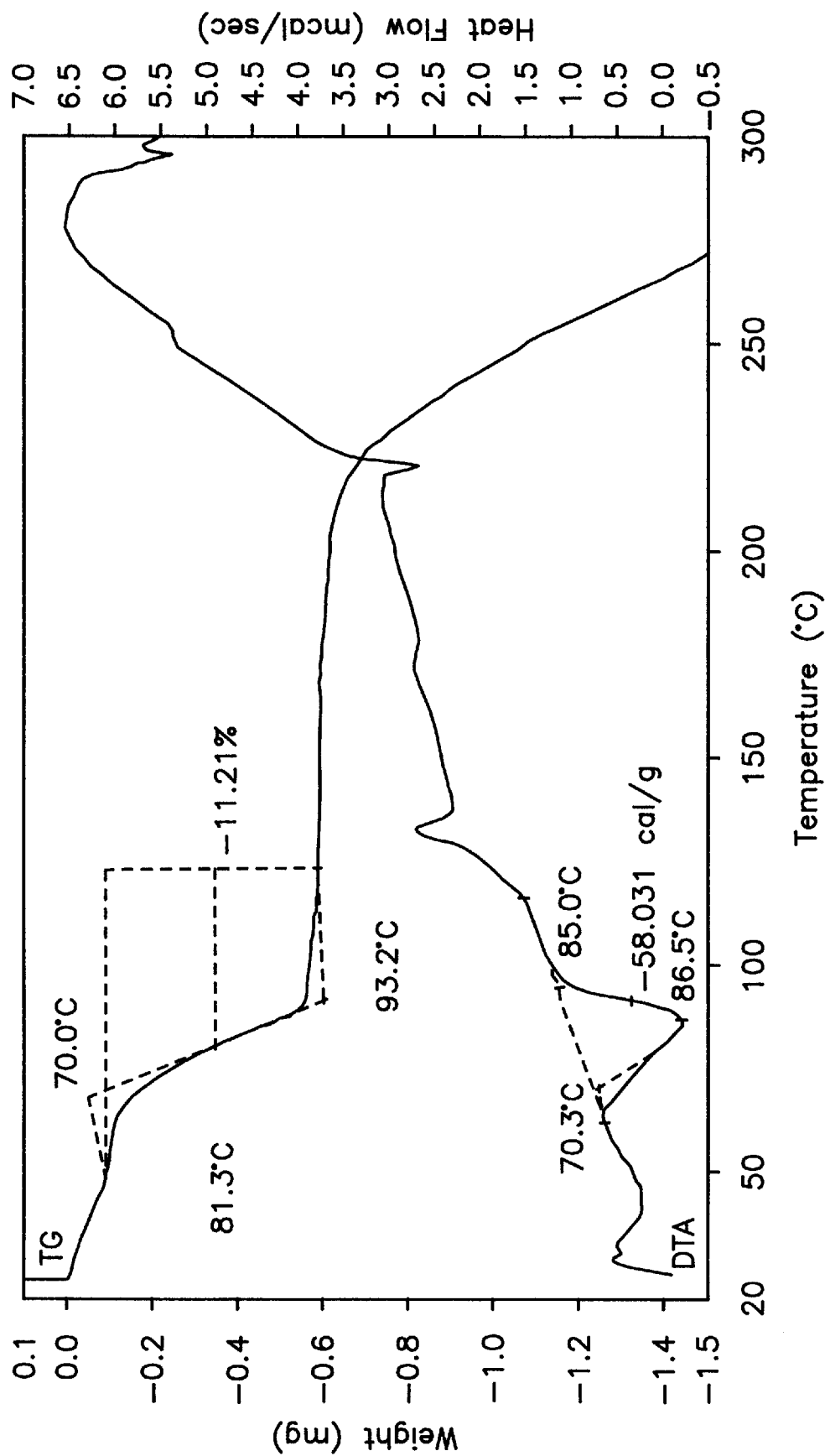
FIG. 14 is thermogravimetric and differential thermal analysis (TG-DTA) of the polymorph (IV).
Figure 15:
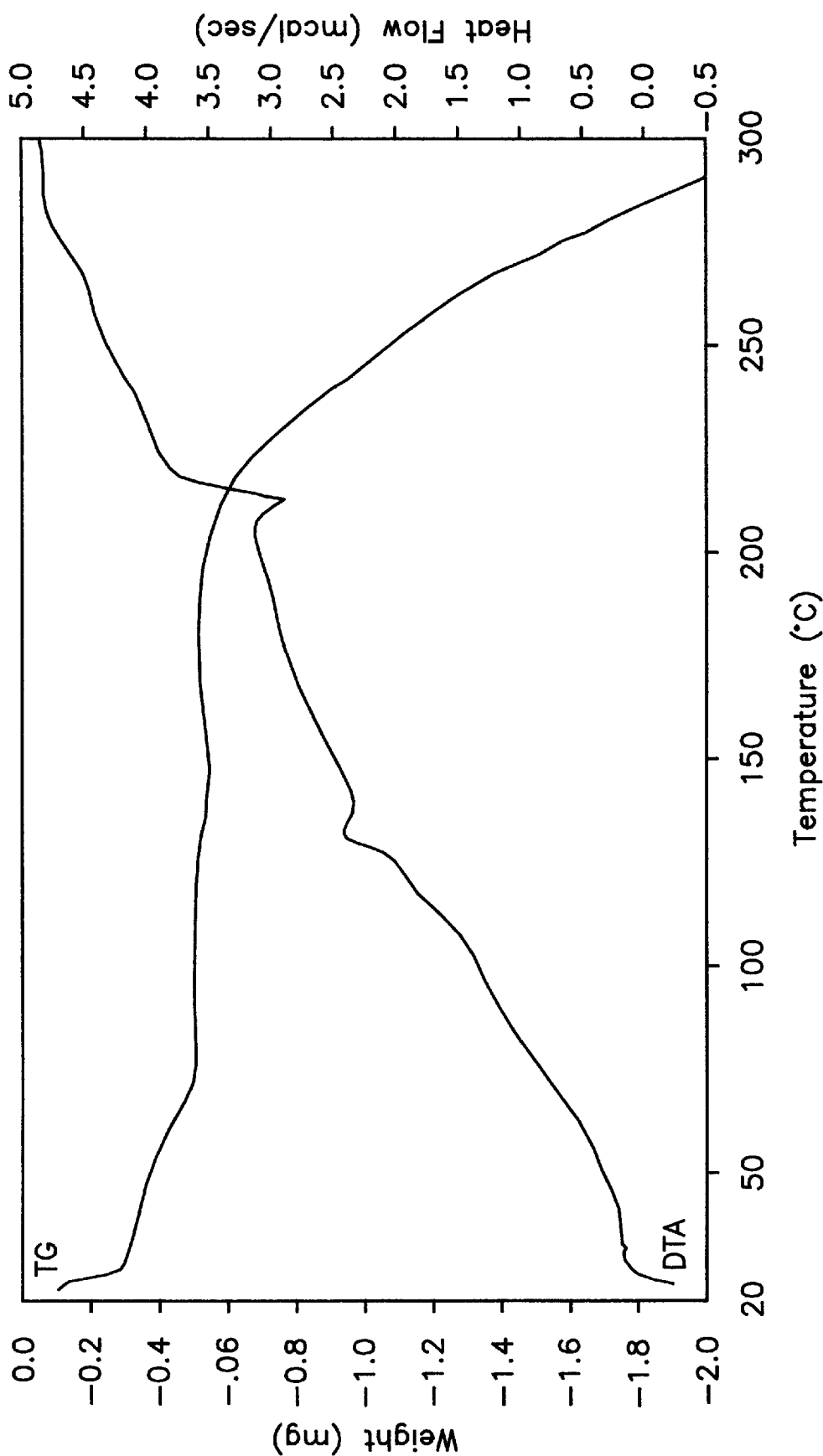
FIG. 15 is thermogravimetric and differential thermal analysis (TG-DTA) of the amorphous form.

The products shown in FIGS. 1 to 15 were again confirmed experimentally to obtain a more clear chart.

EXAMPLES

The present invention will now be described in more detail with reference to the following Examples. It is needless to say that the technical scope of the present invention is not limited to these Examples.

Examples 1 to 8 relates to processes for preparing a polymorph (I).

Examples 9 to 15, processes for preparing a polymorph (II).

Examples 16 to 27, processes for preparing a polymorph (III).

Examples 28, process for preparing a polymorph (IV).

Reference Examples 1, process for preparing a amorphous form of Donepezil hydrochloride.

Example 1

Polymorph (I) of Donepezil Hydrochloride

One gram of Donepezil hydrochloride was dissolved in 5 ml of methanol. Adding 10 ml of diisopropyl ether and stirring the mixture in a bath containing ice-water, filtration of the separated crystal and drying under atmosphere afforded 0.9 g of the title compound.

Example 2

Polymorph (I) of Donepezil Hydrochloride

One gram of Donepezil hydrochloride was dissolved in 5 ml of methanol under heating. After cooling to room temperature, 10 ml of isopropyl ether was added. Stirring was continued for 30 minutes at room temperature, then filtration of the separated crystal and drying under atmosphere afforded 0.9 g of the title compound.

Example 3

Polymorph (I) of Donepezil Hydrochloride

One gram of Donepezil hydrochloride was dissolved in 5 ml of methanol under heating. After initiation of cooling the solution, it started to separate crystal at 15° C. of the inner temperature. After 10 minutes, 10 ml of isopropyl ether was added. Stirring was continued for 1 hour at room temperature, then filtration of the separated crystal and drying under atmosphere afforded 0.9 g of the title compound.

Example 4

Polymorph (I) of Donepezil Hydrochloride 5 g of Donepezil hydrochloride was dissolved in 25 ml of methanol under heating, followed by cooling the mixture in a bath containing ice water. Filtration of the separated crystal and drying under atmosphere afforded 4.6 g of the title compound.

Example 5

Polymorph (I) of Donepezil Hydrochloride 0.3 g of Donepezil was dissolved in 1.5 ml of methanol, followed by addition of 0.97 ml of 10%-hydrochloric acid in methanol mixture. Filtration of the separated crystal and drying under atmosphere afforded 0.2 g of the title compound.

Example 6

Polymorph (I) of Donepezil Hydrochloride 0.3 g of Donepezil was dissolved in 3 ml of ethanol under heating, followed by addition of 3 ml of diisopropyl ether and 0.79 ml of 10%-hydrochloric acid in methanol mixture. Filtration of the separated crystal and drying under atmosphere afforded 0.2 g of the title compound.

Example 7

Polymorph (I) of Donepezil Hydrochloride 10 g of Donepezil was dissolved in 100 ml of ethanol under heating. Under stirring, a mixture of concentrated hydrochloric acid (3.1 g) and ethanol (28 ml) was added hereinto, 7; followed by addition of 150 ml of diisopropyl ether. Filtration of the crystals after 10 seconds from the separation and drying under atmosphere afforded 9.36g of the title compound with a yield of 85.4%, a water content of 5.17% and melting point of 225–226° C. (Decomposition).

Example 8

Polymorph (I) of Donepezil Hydrochloride 10 g of Donepezil hydrochloride was dissolved in 50 ml of methanol under heating. Under stirring in a bath containing ice water, 600 ml of diethyl ether was added. Stirring was continued for 1 hour in the same condition, then filtration of the crystals and drying under atmosphere afforded 10.0 g of the title compound.

Example 9

Polymorph (II) of Donepezil Hydrochloride 13.7 g of Donepezil and 4.4ml of hydrochloric acid were dissolved in 100 ml of ethanol under heating. Under stirring at room temperature, 200 ml of diisopropyl ether was added. Filtration of the crystals and drying under vacuum afforded 11.2 g of the title compound.

Example 10

Polymorph (II) of Donepezil Hydrochloride 50 g of Donepezil was dissolved in 200 ml of ethanol under heating. After cooling to room temperature, 27.3 g of 18%-hydrogen chloride in ethanol solution was added. After setting calmly for 1 hour, the mixture was concentrated under vacuum, then drying the obtained crystal under atmosphere afforded 55.0 g of the title compound.

Example 11

Polymorph (II) of Donepezil Hydrochloride 0.5 g of Donepezil was dissolved in 5 ml of ethanol under heating. Under stirring at room temperature, 1.31 ml of 10%-concentrated hydrochloric acid in ethanol was added, followed by addition of 5 ml of diisopropyl ether. Filtration of the crystals after 10 minutes from the separation and drying under atmosphere afforded 0.4 g of the title compound.

Example 12

Polymorph (II) of Donepezil Hydrochloride 5.6 g of Donepezil hydrochloride was dissolved in 30 ml of ethanol, followed by addition of 100 ml of diisopropyl ether. The mixture was cooled in a bath containing ice water. Then filtration of the crystals and drying at 50° C. for three days afforded 4.9 g of the title compound.

Example 13

Polymorph (II) of Donepezil Hydrochloride 23.3 g of Donepezil hydrochloride was dissolved in 250 ml of ethanol under heating. Under stirring in a bath containing ice water, 600 ml of diethyl ether was added. After setting calmly for 3 hours, filtration of the crystals and drying at 85° C. for 22 hours afforded 22.7 g of the title compound.

Example 14

Polymorph (II) of Donepezil Hydrochloride 10 g of Donepezil was dissolved in 100 ml of ethanol under heating. Under stirring, 150 ml of a mixture of concentrated hydrochloric acid (3.1 g) and ethanol (28 ml) was added, followed by addition of 150 ml of diisopropyl ether. Filtration of the crystals after 15 minutes from the separation and drying under atmosphere afforded 9.0 g of the title compound with a yield of 82.1% and melting point of 224–226° C. (Decomposition).

Example 15

Polymorph (II) of Donepezil Hydrochloride 40.0 g of Donepezil hydrochloride was dissolved in 700 ml of ethanol under heating. Under cooling in a bath containing ice water, 500 ml of diisopropyl ether was added, and crystallization was done by rubbing the flask wall with spatula. Then filtration of the crystals and drying at 50° C. for 12 hours afforded 31.4 g of the title compound.

Example 16

Polymorph (III) of Donepezil Hydrochloride 161 g of Donepezil hydrochloride was dissolved in 2,000 ml of ethanol under heating. After cooling to room temperature, 5,000 ml of diethyl ether was added under stirring. Then filtration of the crystals and drying at 35° C. for 12 hours afforded 120 g of the title compound with a yield of 74.5% and a water content of 0.15%.

Example 17

Polymorph (III) of Donepezil Hydrochloride 308 g of Donepezil was dissolved in 700 ml of ethanol. Under stirring, 230 ml of 10%-hydrogen chloride in ethanol solution and 5000 ml of diethyl ether were added successively. Filtration of the crystals and drying at 50° C. for 1 hour, then at 60° C. for 30 minutes, then at 85° C. for 12 hours afforded 269 g of the title compound.

Example 18

Polymorph (III) of Donepezil Hydrochloride 59 g of Donepezil was dissolved in 590 ml of ethanol. Under cooling in a bath containing ice water, 17.8 g of concentrated hydrochloric acid and 885 ml of diisopropyl ether were added successively. After stirring over night at room temperature, filtration of the crystals and drying at 55° C. for 22 hours afforded 62 g of the title compound.

Example 19

Polymorph (III) of Donepezil Hydrochloride 5 g of Donepezil hydrochloride was dissolved in 100 ml of ethanol under heating. After cooling to room temperature, 100 ml of n-hexane was added hereinto under stirring, followed by cooling in a bath containing ice water. Stirring was continued for 1 hour. Filtration of the crystals and drying at room temperature afforded 4 g of the title compound.

Example 20

Polymorph (III) of Donepezil Hydrochloride

One gram of Donepezil hydrochloride was dissolved in 15 ml of dichloromethane under heating. After cooling to room temperature, 15 ml of n-hexane was added hereinto under stirring, followed by cooling in a bath containing ice water. Stirring was continued for 1 hour. Filtration of the crystals and drying at room temperature afforded 0.9 g of the title compound.

Example 21

Polymorph (III) of Donepezil Hydrochloride 0.5 g of Donepezil was dissolved in 10 ml of acetone under heating. Under stirring at room temperature, 0.13 ml of concentrated hydrochloric acid was added hereinto. Stirring was continued for 30 minutes. Filtration of the crystals and drying at 85° C. for 16 hours afforded 0.5 g of the title compound.

Example 22

Polymorph (III) of Donepezil Hydrochloride 0.3 g of Donepezil was dissolved in 3 ml of ethyl acetate under heating. Under stirring at room temperature, 0.79 ml of 10%-hydrogen chloride in ethanol solution was added. Filtration of the crystals and drying at 85° C. for 3 hours, then at 70° C. for 16 hours afforded 0.3g of the title compound.

Example 23

Polymorph (III) of Donepezil Hydrochloride 10 g of Donepezil was dissolved in 100 ml of ethanol under heating. Under stirring, a mixture of 3.1 g of concentrated hydrochloric acid and 28 ml of ethanol and then 150 ml of diisopropyl ether were added successively. Stirring was continued for 1 hour from the separation of crystals. Filtration of the crystals and drying at room temperature afforded 9.86 g of the title compound with a yield of 90%, a water content of 0.26% and melting point of 229–231° C. (Decomposition).

Example 24

Polymorph (III) of Donepezil Hydrochloride 5.0 g of The polymorph (I) of Donepezil hydrochloride was spread on a laboratory dish (Schale) and was allowed to stand for 7 days under ventilation of air at 85° C. 4.9 g of the title compound was obtained.

Example 25

Polymorph (III) of Donepezil Hydrochloride 5.0 g of the polymorph (I) of Donepezil hydrochloride was spread on a laboratory dish (Schale) and was allowed to stand for 2 days under ventilation of air at 85° C., then for 3 days under ventilation of air at 105° C. 4.8 g of the title compound was obtained.

Example 26

Polymorph (III) of Donepezil Hydrochloride 5.0 g of The polymorph (I) of Donepezil hydrochloride was spread on a laboratory dish (Schale) and was allowed to stand for 5 days under ventilation of air at 85° C. 4.9 g of the title compound was obtained.

Example 27

Polymorph (III) of Donepezil Hydrochloride 5.0 g of the polymorph (I) of Donepezil hydrochloride was spread on a laboratory dish (Schale) and was allowed to stand for 3 days under ventilation of air at 105° C. 4.9 g of the title compound was obtained.

Example 28

Polymorph (IV) of Donepezil Hydrochloride 15.0 g of the polymorph (II) of Donepezil hydrochloride was spread on a laboratory dish (Schale) and was continued to stand for 2 weeks under atmosphere having a relative humidity of 100%. 14.8 g of the title compound was obtained with melting point of 226–228° C. (Decomposition).

Reference Examples 1

Amorphous Form of Donepezil Hydrochloride 15.0 g of Donepezil hydrochloride was dissolved in 300 ml of water. The solution was frozen in a bath containing dry ice and acetone and freezing-dried (lyophilizated) for 4 days at −82° C. 14.8 g of the title compound was obtained.

The present invention will be futhermore described in detail with reference to the following Examples.

Examples 29 to 44, processes for preparing a polymorph (I).

Examples 45 to 57, processes for preparing a polymorph (II).

Examples 58 to 98, process for preparing a polymorph (III).

Examples 99 to 108 relates to processes for preparing a polymorph (IV).

Example 109, process for preparing a polymorph (V).

Example 29

Polymorph (I) of Donepezil Hydrochloride 1.0 g of Donepezil was dissolved in 4 ml of methanol under heating at 40° C. The solution was cooled in an iced water bath. 0.31 g of Concentrated hydrochloric acid in 1 ml of methanol was added hereinto at 10° C. inner temperature. It continued stirring for 90 minutes in an iced water bath. Filtration of the separated crystals followed by drying afforded 0.43 g of the title compound. (water content: 5.33%)

Example 30

Polymorph (I) of Donepezil Hydrochloride 1.0 g of Donepezil was dissolved in 4 ml of methanol under heating at 40° C. The solution was cooled in an iced water bath. 0.31 g of Concentrated hydrochloric acid in 1 ml of methanol was added hereinto. After 5 minutes, 30 ml of tert-butyl methyl ether (hereinafter, abbreviated as TBME) was added at 3° C. inner temperature. It continued stirring for 30 minutes in an iced water bath. Filtration of the separated crystals followed by drying afforded 1.10 g of the title compound. (water content: 5.60%)

Example 31

Polymorph (I) of Donepezil Hydrochloride 1.0 g of Donepezil was dissolved in 4 ml of methanol under heating at 40° C. The solution was cooled in an iced water bath. 0.31 g of Concentrated hydrochloric acid in 1 ml of methanol was added hereinto. After 5 minutes, 30 ml of diisopropyl ether (hereinafter, abbreviated as IPE) was added at 3° C. inner temperature. It continued stirring for 30 minutes in an iced water bath. Filtration of the separated crystals followed by drying afforded 1.13 g of the title compound. (water content: 5.50%)

Example 32

Polymorph (I) of Donepezil Hydrochloride 1.0 g of Donepezil was dissolved in 4 ml of methanol under heating at 40° C. The solution was cooled in an iced water bath. 0.31 g of Concentrated hydrochloric acid in 1 ml of methanol was added hereinto at 12° C. inner temperature. After 7 minutes, 30 ml of ethyl acetate was added at 3°C. inner temperature successively. It continued stirring for 30 minutes in an iced water bath. Filtration of the separated crystals followed by drying afforded 0.71 g of the title compound. (water content: 5.22%)

Example 33

Polymorph (I) of Donepezil Hydrochloride 1.0 g of Donepezil was dissolved in 4 ml of ethanol under heating at 40° C. The solution was cooled in an iced water bath. After cooling for 5 minutes, 0.31 g of concentrated hydrochloric acid in 1 ml of ethanol was added hereinto. It continued stirring for 30 minutes in an iced water bath. A small portion of the polymorph (I) of Donepezil hydrochloride was added hereinto. It continued stirring for further 30 minutes in an iced water bath. Filtration of the separated crystals followed by drying afforded 0.70 g of the title compound. (water content: 5.33%)

Example 34

Polymorph (I) of Donepezil Hydrochloride 1.0 g of Donepezil was dissolved in 4 ml of tetrahydrofuran (hereinafter, abbreviated as THF) at 24° C. The solution was cooled in an iced water bath. 0.31 g of Concentrated hydrochloric acid in 1 ml of THF was added hereinto. It continued stirring for 40 minutes in an iced water bath. Filtration of the separated crystals followed by drying afforded 1.00 g of the title compound. (water content: 5.67%)

Example 35

Polymorph (I) of Donepezil Hydrochloride 1.0 g of Donepezil was dissolved in 9 ml of acetonitrile under heating at 40° C. The solution was cooled in an iced water bath. After cooling for 2 minutes, 0.31 g of concentrated hydrochloric acid in 1 ml of acetonitrile was added hereinto. It continued stirring for 50 minutes in an iced water bath. Filtration of the separated crystals followed by drying afforded 0.63 g of the title compound. (water content: 5.59%)

Example 36

Polymorph (I) of Donepezil Hydrochloride 4.0 g of Donepezil was dissolved in 20 ml of methanol under heating at 40° C. The solution was cooled in an iced water bath. Hydrogen chloride gas was blown hereinto at 3° C. inner temperature, until the atmosphere turns acidic. It continued stirring for 20 minutes in an iced water bath. Filtration of the separated crystals followed by drying afforded 3.40 g of the title compound. (water content: 5.19%)

Example 37

Polymorph (I) of Donepezil Hydrochloride 10.0 g of Donepezil hydrochloride was dissolved in 60 ml of methanol under reflux. Heating was ceased. 120 ml of IPE was added hereinto at 60° C. inner temperature. It continued stirring for 20 minutes in an iced water bath. Filtration of the separated crystals followed by drying afforded 9.80 g of the title compound. (water content: 5.87%)

Example 38

Polymorph (I) of Donepezil Hydrochloride 3.0 g of Donepezil hydrochloride was dissolved in 18 ml of methanol under reflux. Heating was ceased. 36 ml of IPE was added hereinto at 54° C. inner temperature. It continued stirring for 20 minutes in an iced water bath. Filtration of the separated crystals followed by drying afforded 2.95 g of the title compound. (water content: 5.55%)

Elementary Analysis:

|  | C | H | N | Cl |
|---|---|---|---|---|
| found (%) | 65.55 | 7.53 | 3.05 | 8.16 |

Example 39

Polymorph (I) of Donepezil Hydrochloride 1.0 g of Donepezil hydrochloride was dissolved in 5 ml of methanol under reflux. The solution was cooled in an iced water bath. 30 ml of TBME was added hereinto at 3° C. inner temperature. It continued stirring for 30 minutes in an iced water bath. Filtration of the separated crystals followed by drying afforded 1.00 g of the title compound. (water content: 5.40%)

Example 40

Polymorph (I) of Donepezil Hydrochloride 1.0 g of Donepezil hydrochloride was dissolved in 5 ml of methanol under reflux. The solution was cooled in an iced water bath. After cooling for 2 minutes, it started to separate crystals. 1 Minutes passed from the initiation of separation, 30 ml of ethyl acetate was added hereinto. It continued stirring for 30 minutes in an iced water bath. Filtration of the separated crystals followed by drying afforded 1.00 g of the title compound. (water content: 5.60%)

Example 41

Polymorph (I) of Donepezil Hydrochloride 1.0 g of Donepezil hydrochloride was dissolved in 5 ml of methanol under reflux. The solution was cooled in an iced water bath. 30 ml of n-hexane was added hereinto at 3° C. inner temperature. It continued stirring for 70 minutes in an iced water bath. Filtration of the separated crystals followed by drying afforded 0.89 g of the title compound. (water content: 5.66%)

Example 42

Polymorph (I) of Donepezil Hydrochloride 1.0 g of Donepezil hydrochloride was dissolved in 20 ml of ethanol under reflux. The solution was cooled in an iced waterbath. It continued stirring for70 minutes in an iced water bath. Filtration of the separated crystals followed by drying afforded 0.48 g of the title compound. (water content: 5.72%)

Example 43

Polymorph (I) of Donepezil Hydrochloride 1.0 g of Donepezil hydrochloride was dissolved in 25 ml of ethanol under reflux. The solution was cooled in an iced water bath. 50 ml of IPE was added at 30° C. inner temperature. It continued stirring for 5 minutes in an iced water bath. Filtration of the separated crystals followed by drying afforded 0.86 g of the title compound. (water content: 5.32%)

Example 44

Polymorph (I) of Donepezil Hydrochloride 1.0 g of Donepezil hydrochloride was dissolved in 20 ml of ethanol under reflux. The solution was cooled in an iced water bath. 30 ml of TBME was added hereinto at 3° C. inner temperature. It continued stirring for 30 minutes in an iced water bath. Filtration of the separated crystals followed by drying afforded 1.00 g of the title compound. (water content: 5.33%)

Example 45

Polymorph (II) of Donepezil Hydrochloride 1.0 g of Donepezil was dissolved in 4 ml of ethanol under heating at 40° C. The solution was cooled in an iced water bath. After cooling for 4 minutes, 0.31 g of concentrated hydrochloric acid in 1 ml of ethanol was added hereinto. After 3 minutes, 30 ml of TBME was added hereinto. It continued stirring for 50 minutes in an iced water bath. Filtration of the separated crystals followed by drying afforded 1.08 g of the title compound. (water content: 1.78%)

Example 46

Polymorph (II) of Donepezil Hydrochloride 1.0 g of Donepezil was dissolved in 9 ml of isopropyl alcohol (hereinafter, abbreviated as IPA) under heating at 40° C. The solution was cooled in an iced water bath. 0.31 g of Concentrated hydrochloric acid in 1 ml of IPA was added hereinto. It continued stirring for 30 minutes in an iced water bath. Filtration of the separated crystals followed by drying afforded 0.87 g of the title compound. (water content: 1.10%)

Example 47

Polymorph (II) of Donepezil Hydrochloride 1.0 g of Donepezil was dissolved in 9 ml of acetone at 19° C. 0.31 g of Concentrated hydrochloric acid in 1 ml of acetone was added hereinto. It continued stirring for 5 minutes at room temperature. Filtration of the separated crystals followed by drying afforded 0.87 g of the title compound. (water content: 0.83%)

Example 48

Polymorph (II) of Donepezil Hydrochloride 1.0 g of Donepezil was dissolved in 9 ml of acetone at 24° C. 0.31 g of Concentrated hydrochloric acid in 1 ml of acetone was added hereinto. It continued stirring for 30 minutes in an iced water bath. Filtration of the separated crystals followed by drying afforded 0.92 g of the title compound. (water content: 0.61%)

Example 49

Polymorph (II) of Donepezil Hydrochloride 1.0 g of Donepezil was dissolved in 9 ml of THF at 24° C. 0.31 g of Concentrated hydrochloric acid in 1 ml of THF was added hereinto. It continued stirring for 30 minutes in an iced water bath. Filtration of the separated crystals followed by drying afforded 1.09 g of the title compound. (water content: 0.78%)

Example 50

Polymorph (II) of Donepezil Hydrochloride 3.0 g of Donepezil was dissolved in 30 ml of acetone at 21° C. Hydrogen chloride gas was blown hereinto at room temperature, until the atmosphere turns acidic. After stirring for 3 minutes, filtration of the separated crystals followed by drying afforded 2.80 g of the title compound. (water content: 2.78%)

Example 51

Polymorph (II) of Donepezil Hydrochloride 4.0 g of Donepezil was dissolved in 20 ml of methylene chloride at 18° C. The solution was cooled in an iced water bath. Hydrogen chloride gas was blown hereinto at 4° C. inner temperature, until the atmosphere turns acidic. Argon gas was blown hereinto. After stirring for 2 hours in an iced water bath, filtration of the separated crystals followed by drying afforded 4.09 g of the title compound. (water content: 0.81%)

Example 52

Polymorph (II) of Donepezil Hydrochloride 1.0 g of Donepezil hydrochloride was dissolved in 20 ml of ethanol under reflux. The solution was cooled in an iced water bath. 30 ml of TBME was added hereinto at 20° C. inner temperature. It continued stirring for 3 hours in an iced water bath. Filtration of the separated crystals followed by drying afforded 0.92 g of the title compound. (water content: 0.79%)

Example 53

Polymorph (II) of Donepezil Hydrochloride 1.0 g of Donepezil hydrochloride was dissolved in 20 ml of ethanol under reflux. The solution was cooled to room temperature in an iced water bath. 30 ml of TBME was added hereinto at 20 inner temperature. It continued stirring for 20 minutes at room temperature. Filtration of the separated crystals followed by drying afforded 0.80 g of the title compound. (water content: 0.52%)

Example 54

Polymorph (II) of Donepezil Hydrochloride 10.0 g of Donepezil hydrochloride was dissolved in 100 ml of ethanol under reflux. Under stirring, the solution was added into 200 ml of IPE cooled in an iced water bath. It continued stirring for 5 minutes. Filtration of the separated crystals followed by drying afforded 9.40 g of the title compound. (water content: 0.19%)

Elementary Analysis:

|           | C     | H    | N    | Cl   |
|-----------|-------|------|------|------|
| found (%) | 69.12 | 7.20 | 3.32 | 8.61 |

Example 55

Polymorph (II) of Donepezil Hydrochloride 1.0 g of Donepezil hydrochloride was dissolved in 20 ml of methylene chloride at 18° C. The solution was cooled in an iced water bath. 30 ml of TBME was added hereinto. After stirring for 3 minutes in an iced water bath, filtration of the separated crystals followed by drying afforded 0.88 g of the title compound. (water content: 2.33%)

Example 56

Polymorph (II) of Donepezil Hydrochloride 2.0 g of The polymorph (I) of Donepezil hydrochloride was spread on an laboratory dish (Schale) and was allowed to stand for 16 hours under reduced pressure at 80° C. 1.89 g of the title compound was obtained. (water content: 0.22%)

Example 57

Polymorph (II) of Donepezil Hydrochloride 2.0 g of The amorphous form of Donepezil hydrochloride was spread on an laboratory dish (Schale) and was allowed to stand for 16 hours under reduced pressure at 80° C. 1.98 g of the title compound was obtained. (water content: 1.15%)

Example 58

Polymorph (III) of Donepezil Hydrochloride 1.0 g of Donepezil was dissolved in 4 ml of methanol under heating at 40° C. The solution was cooled in an iced water bath. 0.31 g of Concentrated hydrochloric acid in 1 ml of methanol was added hereinto at 7° C. inner temperature. After 5 minutes stirring, 30 ml of acetone was added hereinto successively. It continued stirring for 1 hour in an iced water bath. Filtration of the separated crystals followed by drying afforded 0.44 g of the title compound. (water content: 0.11%)

Example 59

Polymorph (III) of Donepezil Hydrochloride 1.0 g of Donepezil was dissolved in 4 ml of ethanol under heating at 40° C. The solution was cooled to room temperature in an iced water bath. 0.31 g of Concentrated hydrochloric acid in 1 ml of ethanol was added hereinto. After 5 minutes, 30 ml of TBME was added hereinto at 22° C. inner temperature. It continued stirring over night at room temperature. Filtration of the separated crystals followed by drying afforded 1.09 g of the title compound. (water content: 0.19%)

Elementary Analysis:

|  | C | H | N | Cl |
|---|---|---|---|---|
| found (%) | 69.27 | 7.23 | 3.34 | 8.58 |

Example 60

Polymorph (III) of Donepezil Hydrochloride 1.0 g of Donepezil was dissolved in 9 ml of ethyl acetate under heating at 40° C. The solution was cooled in an iced water bath. 0.31 g of Concentrated hydrochloric acid in 1 ml of ethyl acetate was added hereinto. It continued stirring for 30 minutes at room temperature. Filtration of the separated crystals followed by drying afforded 1.08 g of the title compound. (water content: 0.21%)

Example 61

Polymorph (III) of Donepezil Hydrochloride 1.0 g of Donepezil was almost dissolved in 9 ml of acetonitrile at 21° C. The solution was cooled in an iced water bath. 0.31 g of Concentrated hydrochloric acid in 1 ml of acetonitrile was added hereinto. The solution became homogeneous. It continued stirring over night at room temperature. Filtration of the separated crystals followed by drying afforded 1.05 g of the title compound. (water content: 0.05%)

Example 62

Polymorph (III) of Donepezil Hydrochloride 1.0 g of Donepezil was dissolved in 9 ml of acetone under heating at 40° C. The solution was cooled to room temperature in an iced water bath. 0.31 g of Concentrated hydrochloric acid in 1 ml of acetone was added hereinto. It continued stirring over night at room temperature. Filtration of the separated crystals followed by drying afforded 1.08 g of the title compound. (water content: 0.03%)

Example 63

Polymorph (III) of Donepezil Hydrochloride 1.0 g of Donepezil was dissolved in the mixture comprising from 29 ml of acetone and 1 ml of ion exchange purified water under stirring at 20° C. The solution was cooled in an iced water bath. 0.31 g of Concentrated hydrochloric acid in 1 ml of acetone was added hereinto. After stirring for 30 minutes in an iced water bath, filtration of the separated crystals followed by drying afforded 0.83 g of the title compound. (water content: 0.56%)

Example 64

Polymorph (III) of Donepezil Hydrochloride 1.0 g of Donepezil was dissolved in 9 ml of THF at 24° C. 0.31 g of Concentrated hydrochloric acid in 1 ml of THF was added hereinto. It continued stirring for 30 minutes in an iced water bath. Filtration of the separated crystals followed by drying afforded 1.09 g of the title compound. (water content: 0.54%)

Example 65

Polymorph (III) of Donepezil Hydrochloride 1.0 g of Donepezil was dissolved in 4 ml of DMF under heating at 40° C. The solution was cooled in an iced water bath. 0.31 g of Concentrated hydrochloric acid in 1 ml of DMF was added hereinto. It continued stirring for 30 minutes in an iced water bath. Filtration of the separated crystals followed by drying afforded 1.08 g of the title compound. (water content: 0.72%)

Example 66

Polymprph (III) of Donepezil Hydrochloride 1.0 g of Donepezil was almost dissolved in 9 ml of DMSO at 20° C. 0.31 g of Concentrated hydrochloric acid in 1 ml of DMSO was added hereinto. After stirring for 1 hour at room temperature, 30 ml of TBME was added hereinto. It continued stirring over night at room temperature. Filtration of the separated crystals followed by drying afforded 0.97 g of the title compound. (water content: 0.25%)

Example 67

Polymorph (III) of Donepezil Hydrochloride 2.0 g of Donepezil was dissolved in 20 ml of ethanol under heating at 40° C. The solution was cooled to room temperature in an iced water bath. Hydrogen chloride gas was blown hereinto at 24° C. inner temperature, until the atmosphere turns acidic. After stirring for 10 minutes, 50 ml of TBME was added. It continued stirring over night at room temperature. Filtration of the separated crystals followed by drying afforded 2.11 g of the title compound. (water content: 0.07%)

Example 68

Polymorph (III) of Donepezil Hydrochloride 2.0 g of Donepezil was dissolved in 30 ml of toluene at 20° C. Hydrogen chloride gas was blown hereinto at room temperature, until the atmosphere turns acidic. Argon gas was blown hereinto. After stirring for 30 minutes, filtration of the separated crystals followed by drying afforded 2.21 g of the title compound. (water content: 0.65%)

Example 69

Polymorph (III) of Donepezil Hydrochloride 1.0 g of Donepezil hydrochloride was dissolved in 5 ml of methanol under reflux. Heating was ceased. After stirring over night at room temperature, it continued stirring 2 hours additionally in an iced water. Filtration of the separated crystals followed by drying afforded 0.90 g of the title compound. (water content: 0.05%)

Example 70

Polymorph (III) of Donepezil Hydrochloride 1.0 g of Donepezil hydrochloride was dissolved in 5 ml of methanol under reflux. The solution was cooled, then 30 ml of TBME was added hereinto at 40° C. inner temperature. It continued stirring for 3 hours at 40° C. The mixture was cooled in an iced water bath, and was kept for 45 minutes under stirring. Filtration of the separated crystals followed by drying afforded 0.94 g of the title compound. (water content: 0.13%)

Example 71

Polymorph (III) of Donepezil Hydrochloride 1.0 g of Donepezil hydrochloride was dissolved in 5 ml of methanol under reflux. The solution was cooled in an iced water bath. After 4 minutes, it started to separate crystals. 30 ml of Acetonitrile was added hereinto, then the crystal was dissolved immediately. After stirring over night at room temperature, filtration of the separated crystals followed by drying afforded 0.10 g of the title compound. (water content: 0.09%)

Example 72

Polymorph (III) of Donepezil Hydrochloride 1.0 g of Donepezil hydrochloride was dissolved in 20 ml of ethanol under reflux. The solution was cooled, then 30 ml of TBME was added hereinto at 40° C. inner temperature. It continued stirring for 3 hours at 40° C. The mixture was cooled in an iced water bath, and was kept for 20 minutes under stirring. Filtration of the separated crystals followed by drying afforded 0.97 g of the title compound. (water content: 0.14%)

Example 73

Polymorph (III) of Donepezil Hydrochloride 1.0 g of Donepezil hydrochloride was dissolved in 120 ml of IPA under reflux. Heating was ceased. It was kept under stirring over night at room temperature. It continued stirring for 1 hour in an iced water bath. Filtration of the separated crystals followed by drying afforded 0.92 g of the title compound. (water content: 0.21%)

Example 74

Polymorph (III) of Donepezil Hydrochloride 1.0 g of Donepezil hydrochloride was dissolved in 15 ml of N,N-dimethylformamide at 100° C. Heating was ceased, and the solution was kept over night under stirring. 30 ml of TBME was added hereinto at 20° C. inner temperature. The mixture was cooled in an iced water bath, and was kept for 3 hours under stirring. Filtration of the separated crystals followed by drying afforded 0.90 g of the title compound. (water content: 0.10%)

Example 75

Polymorph (III) of Donepezil Hydrochloride 1.0 g of Donepezil hydrochloride was dissolved in 15 ml of dimethylsulfoxide (hereinafter, abbreviated as DMSO) under heating at 80° C. The solution was cooled to room temperature in an iced water bath. 30 ml of TBME was added hereinto at 200 inner temperature. It continued stirring over night at room temperature. Filtration of the separated crystals followed by drying afforded 1.01 g of the title compound. (water content: 0.08%)

Example 76 to 95

Polymorph (III) of Donepezil Hydrochloride 1.0 g of the material shown in the below table was suspended in 10 ml of the solvent shown in the below table at room temperature. It continued stirring over night at room temperature. Filtration of the separated crystals followed by drying afforded the title compound.

| Example | Material | Solvent | Yield |
| --- | --- | --- | --- |
| 76 | polymorph (I) | methanol | 0.91 g |
| 77 | polymorph (I) | ethanol | 0.94 g |
| 78 | polymorph (I) | ethyl acetate | 0.93 g |
| 79 | polymorph (I) | acetone | 0.93 g |
| 80 | polymorph (II) | methanol | 0.93 g |
| 81 | polymorph (II) | ethanol | 0.95 g |
| 82 | polymorph (II) | ethyl acetate | 0.95 g |
| 83 | polymorph (II) | acetone | 0.94 g |
| 84 | polymorph (IV) | methanol | 0.92 g |
| 85 | polymorph (IV) | ethanol | 0.90 g |
| 86 | polymorph (IV) | ethyl acetate | 0.92 g |
| 87 | polymorph (IV) | acetone | 0.94 g |
| 88 | polymorph (V) | methanol | 0.96 g |
| 89 | polymorph (V) | ethanol | 0.93 g |
| 90 | polymorph (V) | ethyl acetate | 0.97 g |
| 91 | polymorph (V) | acetone | 0.92 g |
| 92 | amorphous form | methanol | 0.94 g |
| 93 | amorphous form | ethanol | 0.94 g |
| 94 | amorphous form | ethyl acetate | 0.92 g |
| 95 | amorphous form | acetone | 0.96 g |

Example 96

Polymorph (III) of Donepezil Hydrochloride 10.0 g of Donepezil was dissolved in 100 ml of ethanol under heating at 40° C. The solution was cooled to room temperature. 3.01 g of Concentrated hydrochloric acid was added hereinto at 20° C. inner temperature. The solution was set in an iced water bath. After 9 minutes stirring, 150 ml of isopropyl ether was added hereinto at 3° C. inner temperature. It continued stirring for 300 minutes in an iced water bath. Filtration of the separated crystals followed by drying afforded the title compound.

Example 97

Polymorph (III) of Donepezil Hydrochloride 10.0 g of Donepezil was dissolved in 100 ml of ethanol under heating at 40° C. The solution was cooled to room temperature. 3.01 g of Concentrated hydrochloric acid was added hereinto at 20° C. inner temperature. After 9 minutes stirring, 150 ml of isopropyl ether was added hereinto at 20° C. inner temperature. It continued stirring for 120 minutes at room temperature. Filtration of the separated crystals followed by drying afforded the title compound.

Example 98

Polymorph (III) of Donepezil Hydrochloride 10.0 g of Donepezil was dissolved in 100 ml of ethanol under heating at 40° C. The solution was cooled to room temperature. 3.01 g of Concentrated hydrochloric acid was added hereinto at 20° C. inner temperature. The solution was set in an oil bath, and was heated to 40° C. inner temperature. 150 ml of isopropyl ether was added hereinto at 40° C. inner temperature. It continued stirring for 20 minutes at 60° C. inner temperature. Filtration of the separated crystals followed by drying afforded the title compound.

Example 99

Polymorph (IV) of Donepezil Hydrochloride 2.0 g of Donepezil was dissolved in the mixture comprising from 0.65 g of concentrated hydrochloric acid and 10 ml of ion exchange purified water under stirring at 22° C. After stirring at room temperature for 1 hour, filtration of the separated crystals followed by drying afforded 1.80 g of the title compound. (water content: 11.00%)

Example 100

Polymorph (IV) of Donepezil Hydrochloride 1.0 g of Donepezil was dissolved in the mixture comprising from 0.31 g of concentrated hydrochloric acid and 4 ml of ion exchange purified water under stirring at 22° C. 100 ml of THF was added hereinto. It continued stirring for 30 minutes at room temperature. Filtration of the separated crystals followed by drying afforded 1.06 g of the title compound. (water content: 11.14%)

Example 101

Polymorph (IV) of Donepezil Hydrochloride 3.0 g of Donepezil was dissolved in the mixture comprising from 88 ml of THF and 3 ml of ion exchange purified water under stirring at 20° C. 0.93 g of Concentrated hydrochloric acid in 2 ml of THF was added hereinto. After stirring for 30 minutes in an iced water bath, filtration of the separated crystals followed by drying afforded 3.21 g of the title compound. (water content: 11.34%)

Elementary Analysis:

|  | C | H | N | Cl |
|---|---|---|---|---|
| found (%) | 61.30 | 7.76 | 2.86 | 7.68 |

Example 102

Polymorph (IV) of Donepezil Hydrochloride 1.0 g of Donepezil was dissolved in 9 ml of toluene at 22° C. 0.31 g of Concentrated hydrochloric acid in 1 ml of toluene was added hereinto. It continued stirring over night at room temperature. Filtration of the separated crystals followed by drying afforded 1.23 g of the title compound. (water content: 11.40%)

Example 103

Polymorph (IV) of Donepezil Hydrochloride 1.0 g of Donepezil was dissolved in 9 ml of n-hexane at 21° C. 0.31 g of Concentrated hydrochloric acid in 1 ml of n-hexane was added hereinto. It continued stirring over night at room temperature. Filtration of the separated crystals followed by drying afforded 1.623 g of the title compound. (water content: 11.24%)

Example 104

Polymorph (IV) of Donepezil Hydrochloride 1.0 g of Donepezil was dissolved in the mixture comprising from 1 ml of methanol, 3 ml of ion exchange purified water and 0.93 g of concentrated hydrochloric acid at 20° C. It continued stirring for 3 days at room temperature. Filtration of the separated crystals followed by drying afforded 0.83 g of the title compound. (water content: 11.04%)

Example 105

Polymorph (IV) of Donepezil Hydrochloride 2.0 g of Donepezil was suspended in 10 ml of ion exchange purified water. Hydrogen chloride gas was blown hereinto at 23° C. inner temperature, until it became homogeneous. After stirring for 2.5 hours at room temperature, filtration of the separated crystals followed by drying afforded 1.77 g of the title compound. (water content: 11.10%)

Example 106

Polymorph (IV) of Donepezil Hydrochloride 1.0 g of Donepezil hydrochloride was dissolved in 5 ml of ion exchange purified water under heating at 60° C. The solution was cooled to room temperature. After stirring over night at room temperature, filtration of the separated crystals followed by drying afforded 0.92 g of the title compound. (water content: 11.12%)

Example 107

Polymorph (IV) of Donepezil Hydrochloride 1.0 g of The polymorph (II) of Donepezil hydrochloride was spread on an laboratory dish (Schale) and was allowed to stand for 24 hours under atmosphere having an relative humidity of 90%. 1.15 of the Polymorph (IV) was obtained. (watercontent: 12.33%)

Example 108

Amorphous Form & Polymorph (IV) of Donepezil Hydrochloride 10.0 g of the polymorph (III) of Donepezil hydrochloride was spread on an laboratory dish (Schale, φ=250 mm), and was dissolved in 300 ml of ion exchange purified water at 21° C. This solution was moved into freeze-drying apparatus, and dried for 3 days to afford 9.90 g of amorphous form. This material was kept standing for 24 hours under atmosphere having an relative humidity of 90%. 11.20 g of the Polymorph (IV) was obtained. (water content: 11.21%)

Example 109

Polymorph (V) of Donepezil Hydrochloride 2.0 g of the polymorph (IV) of Donepezil hydrochloride was spread on an laboratory dish (Schale, φ=250 mm), and was allowed to stand for 16 hours under reduced pressure at 80° C. 1.75 g of the title compound was obtained. (water content: 0.28%)

Finally, the efficacy of the present invention in view of the stability or hygroscopicity will now be described in comparison with amorphous form of Donepezil hydrochloride. The invention provides advantageous results as follows:

(1) Stability Assay (Method for measurement)

10 mg of each of the polymorphs (I) to (IV) of Donepezil hydrochloride was taken as a couple of samples into tubes, respectively. They were stored under the following conditions and impurity's contents were measured periodically.

| Condition | Storage Period | | | |
|---|---|---|---|---|
| 80° C. | 1 week | 2 weeks | | |
| 60° C. | | 2 weeks | 1 month | |
| 40° C. | | | 1 month | 3 months |
| −20° C. | 1 week | 2 weeks | 1 month | 3 months |

(Method and Condition for Measurement of HPLC Purity)

10 ml of the following mobile phase for HPLC was added into each tube of the aforementioned samples. Then impurity's contents were measured for each sample under the following conditions.

The average was calculated from two results.

| Column (Solid phase) | Inertsil ODS-II (4.6 mm I.D. × 150 mm) |
|---|---|
| Mobile Phase | CH$_3$CN/water/70% HClO$_4$ |
| | (V/V/V = 300:700:1) |
| Detector | UV 271 nm |
| Flow rate | 1.0 ml/min. |
| Injection Volume | 5 ml |
| Column Temperature | room temperature |

Figure 16:
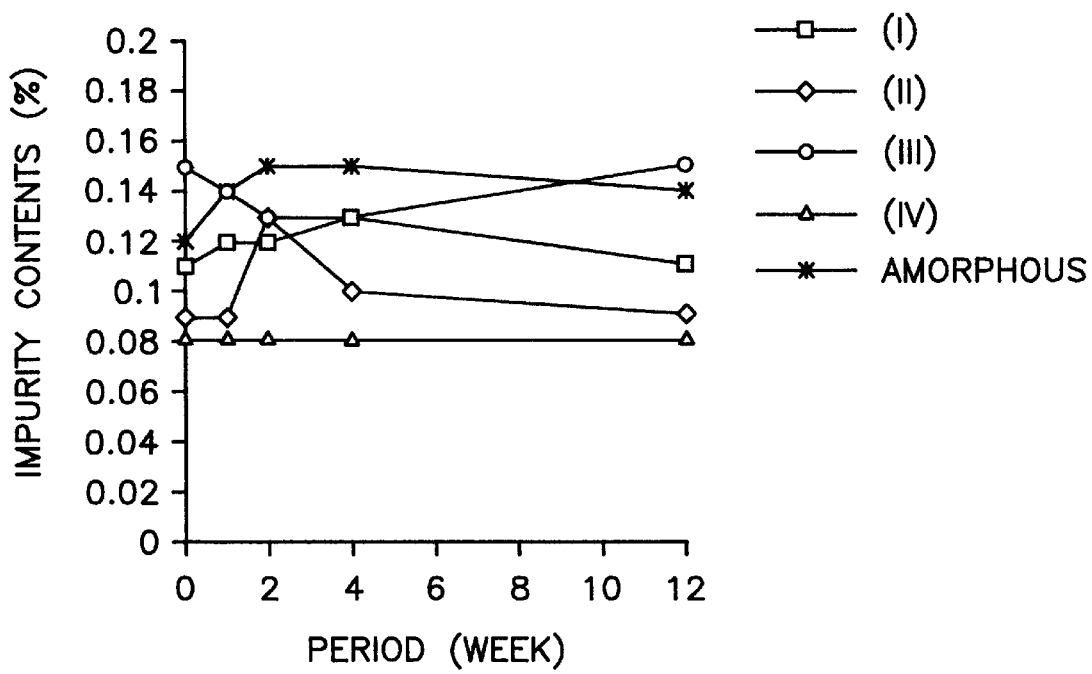
FIG. 16 is change of impurity contents for each polymorphs and amorphous form stored at −20° C.
Figure 17:
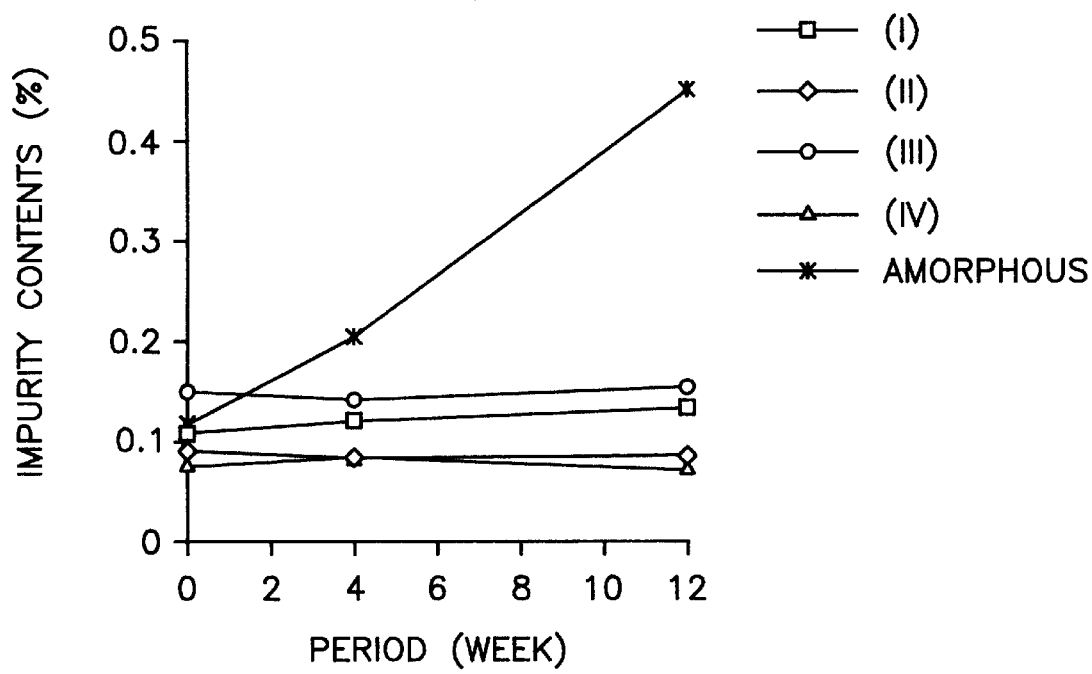
FIG. 17 is change of impurity contents for each polymorphs and amorphous form stored at 40° C.
Figure 18:
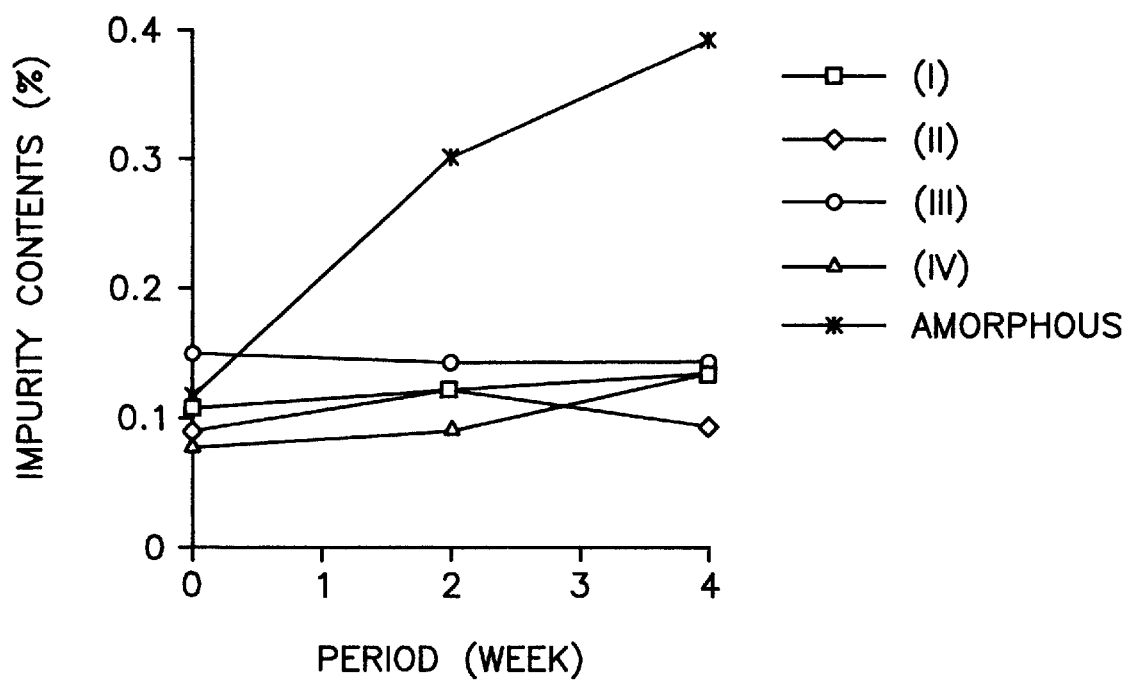
FIG. 18 is change of impurity contents for each polymorphs and amorphous form stored at 60° C.
Figure 19:
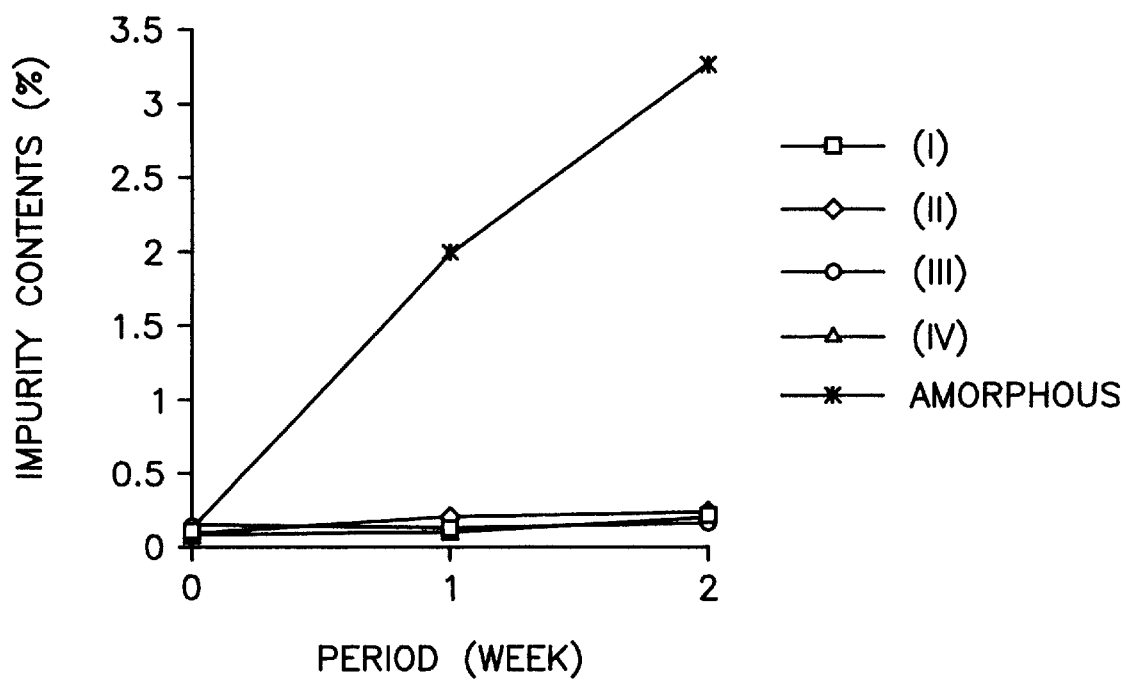
FIG. 19 is change of impurity contents for each polymorphs and amorphous form stored at 80° C.

Results;

| Impurity (%) | 0 | 1 week | 2 weeks | 1 month | 3 months |
|---|---|---|---|---|---|
| 1) Storage at −20° C. (refer to FIG. 16) | | | | | |
| Polymorph (I) | 0.11 | 0.12 | 0.12 | 0.13 | 0.11 |
| Polymorph (II) | 0.09 | 0.09 | 0.13 | 0.10 | 0.09 |
| Polymorph (III) | 0.15 | 0.14 | 0.13 | 0.13 | 0.15 |
| Polymorph (IV) | 0.08 | 0.08 | 0.08 | 0.08 | 0.08 |
| Amorphous | 0.12 | 0.14 | 0.15 | 0.15 | 0.14 |
| 2) Storage at 40° C. (refer to FIG. 17) | | | | | |
| Polymorph (I) | 0.11 | | | 0.12 | 0.13 |
| Polymorph (II) | 0.09 | | | 0.08 | 0.08 |
| Polymorph (III) | 0.15 | | | 0.14 | 0.15 |
| Polymorph (IV) | 0.08 | | | 0.08 | 0.07 |
| Amorphous | 0.12 | | | 0.20 | 0.45 |
| 3) Storage at 60° C. (refer to FIG. 18) | | | | | |
| Polymorph (I) | 0.11 | | | 0.12 | 0.13 |
| Polymorph (II) | 0.09 | | | 0.12 | 0.09 |
| Polymorph (III) | 0.15 | | | 0.14 | 0.14 |
| Polymorph (IV) | 0.08 | | | 0.09 | 0.13 |
| Amorphous | 0.12 | | | 0.30 | 0.39 |
| 4) Storage at 80° C. (refer to FIG. 19) | | | | | |
| Polymorph (I) | 0.11 | 0.12 | 0.19 | | |
| Polymorph (II) | 0.09 | 0.20 | 0.22 | | |
| Polymorph (III) | 0.15 | 0.14 | 0.14 | | |
| Polymorph (IV) | 0.08 | 0.09 | 0.19 | | |
| Amorphous | 0.12 | 2.02 | 3.29 | | |

It is evident from the above results that the polymorphs (I) to (IV) is superior in stability against heat to the amorphous form.

(2) Hygroscopicity Assay
(Method for measurement)

Polymorphs (I) to (IV) were stored under atmosphere having the following relative humidities at 25° C. Water contents were measured according to the general method (Karl Fischer Method) introduced by the Japanese Pharmacopoeia.

Figure 20:
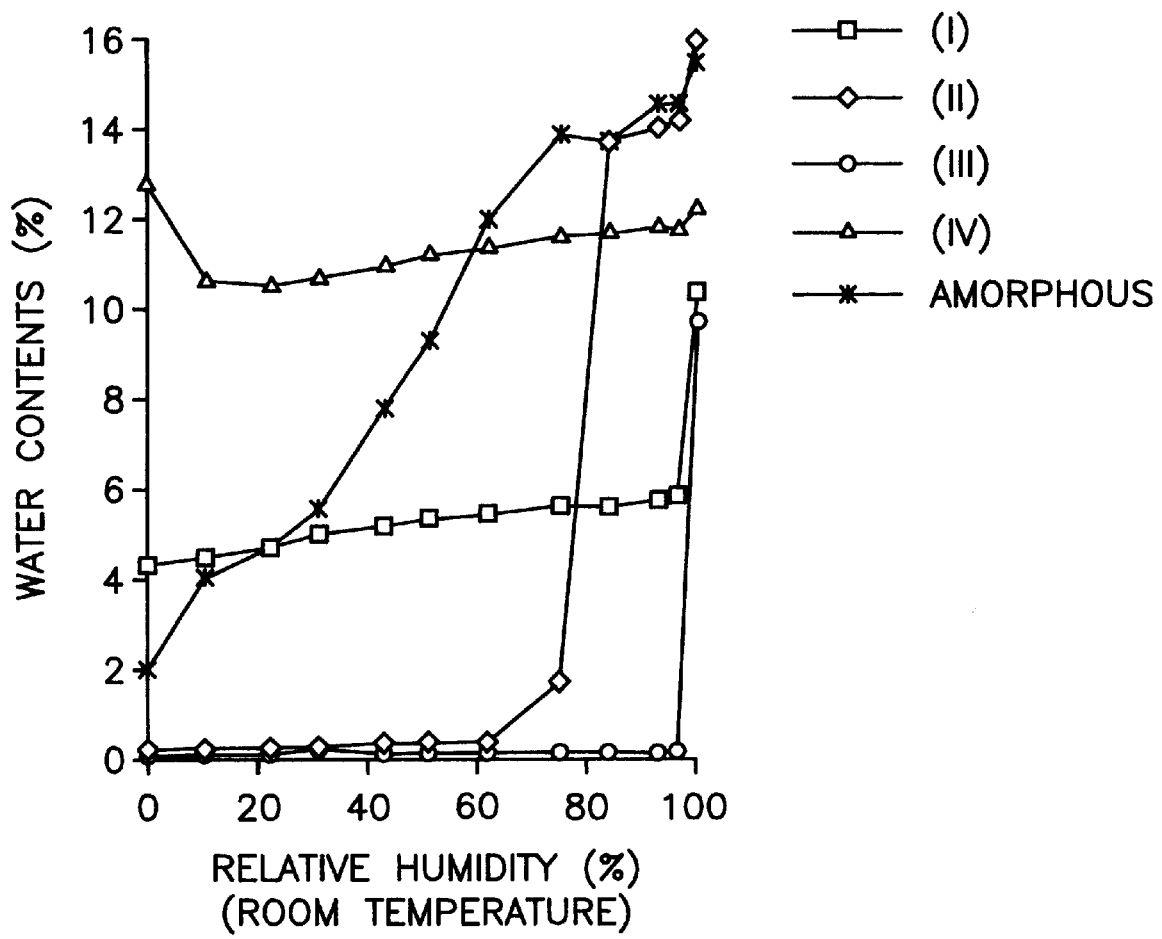
FIG. 20 is water contents for each polymorphs and amorphous form stored at 25° C. under various relative humidity condition.
Figure 21:
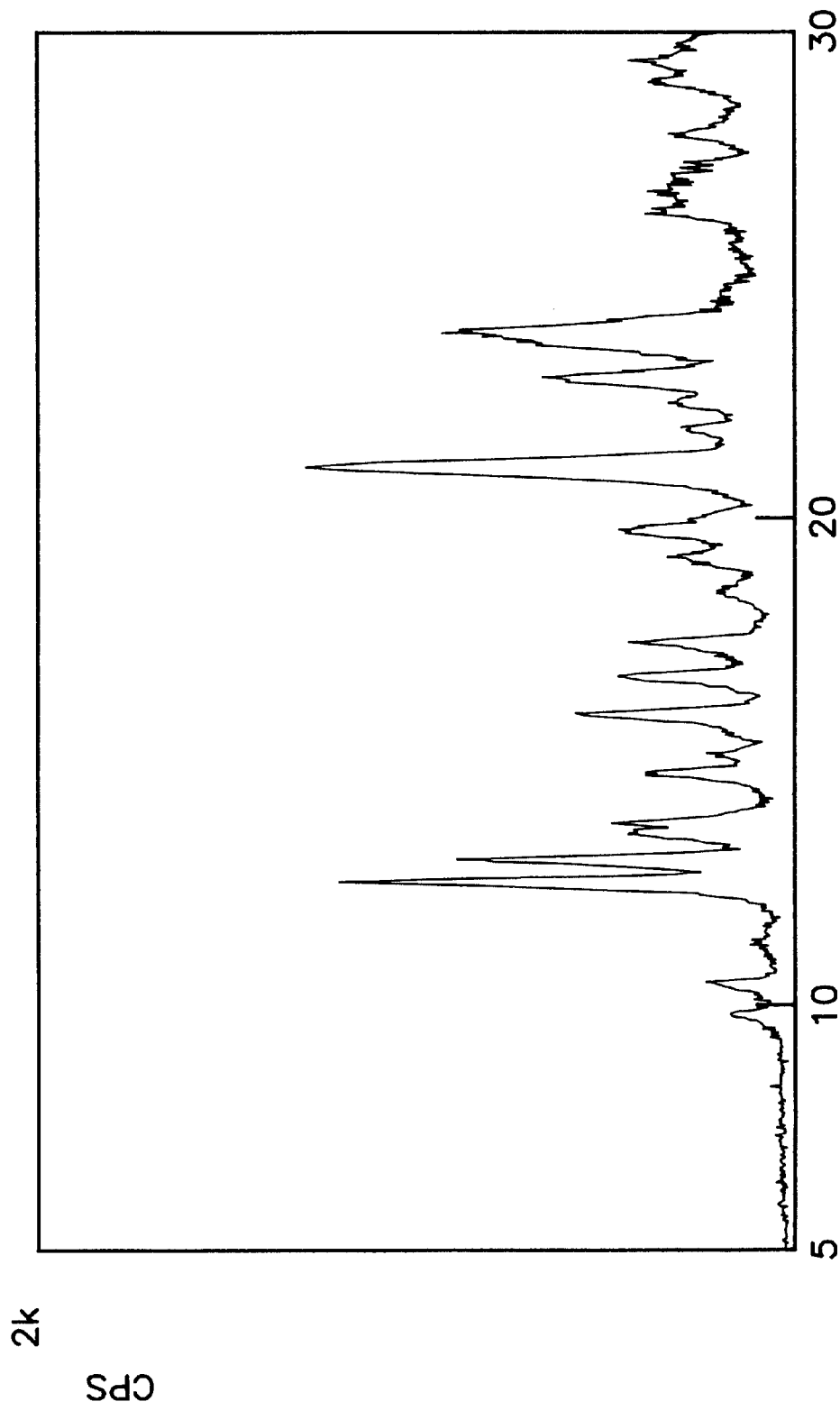
FIG. 21 is clear powder X-ray diffraction pattern of the polymorph
Figure 22:
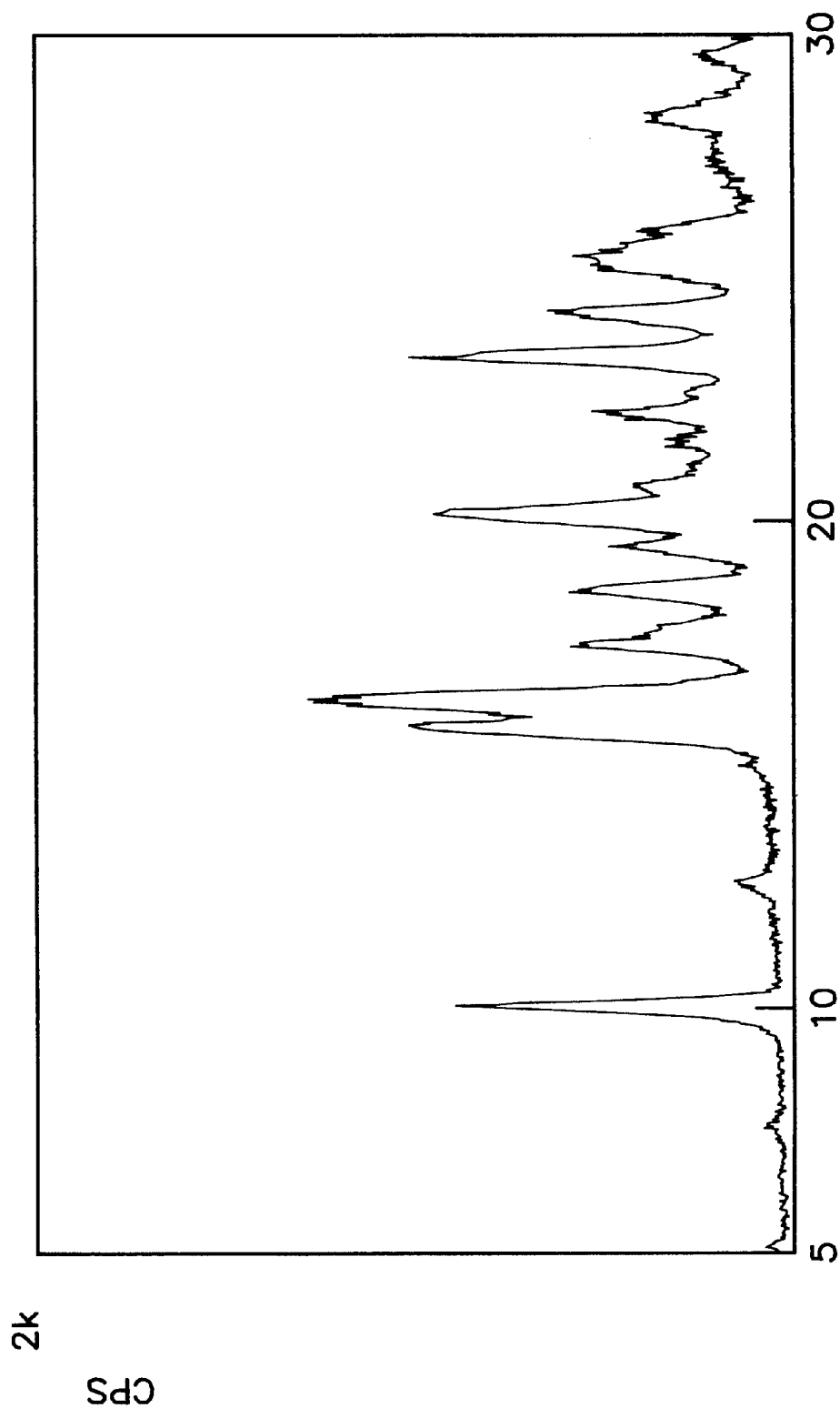
FIG. 22 is clear powder X-ray diffraction pattern of the polymorph
Figure 23:
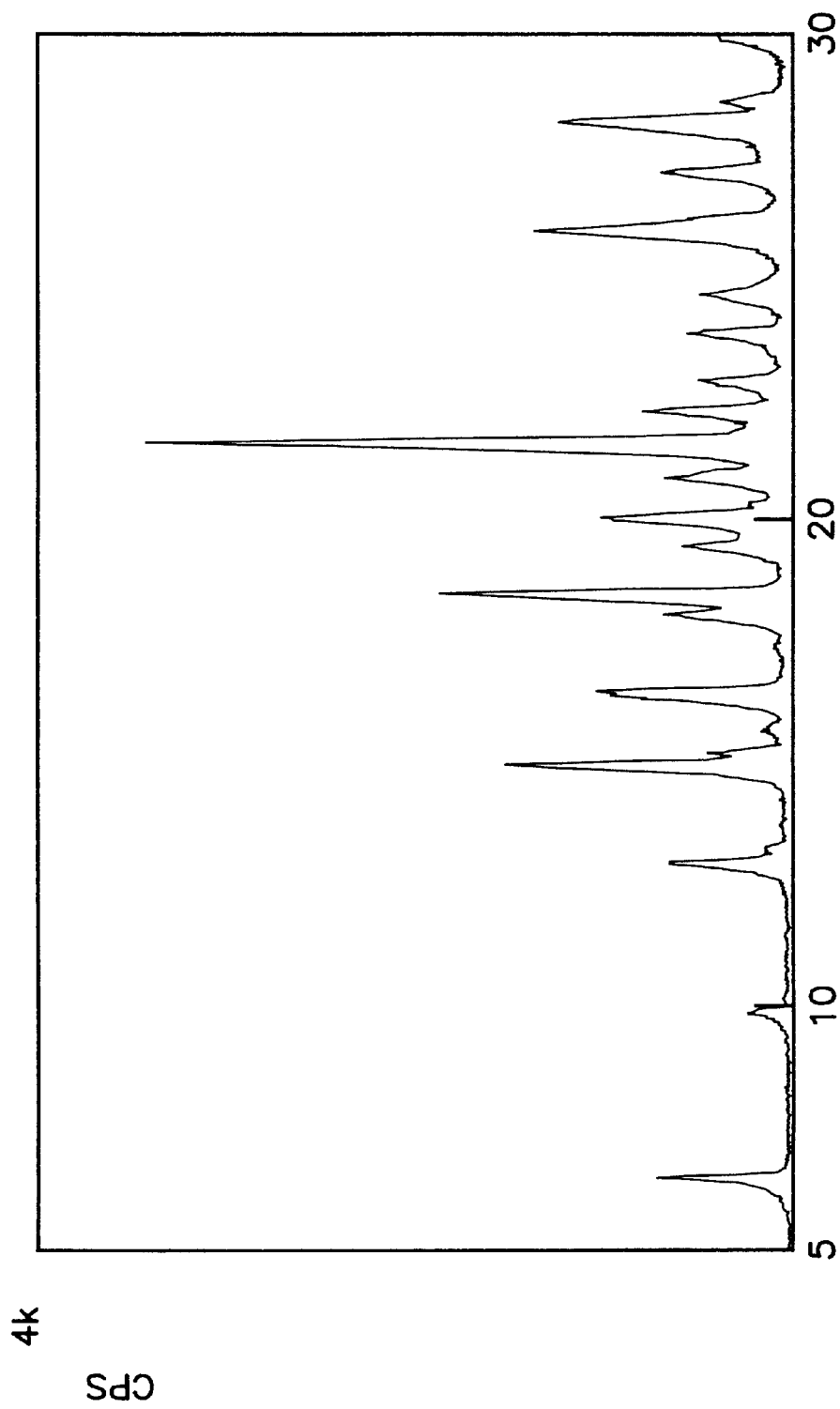
FIG. 23 is clear powder X-ray diffraction pattern of the polymorph
Figure 24:
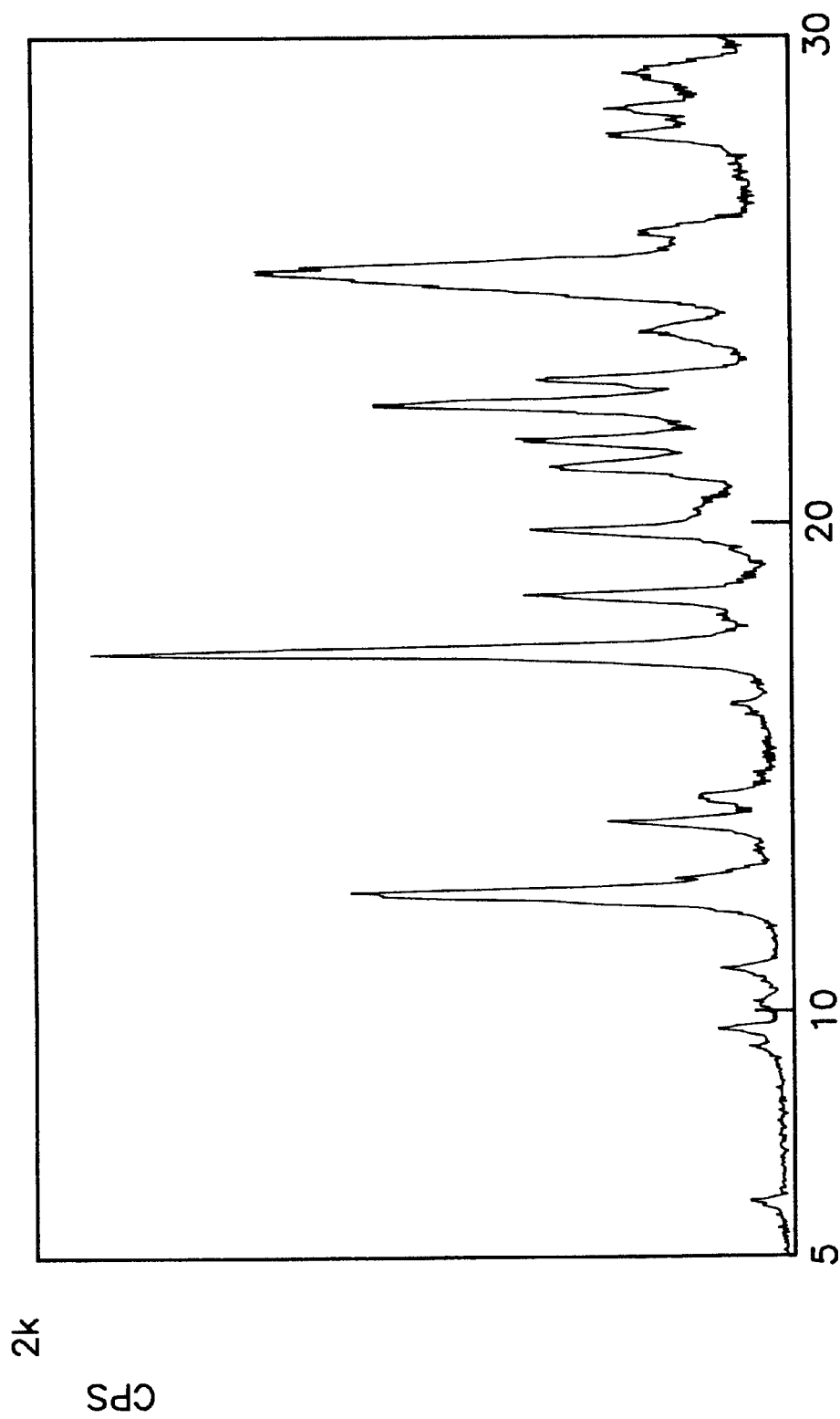
FIG. 24 is clear powder X-ray diffraction pattern of the polymorph (IV).
Figure 25:
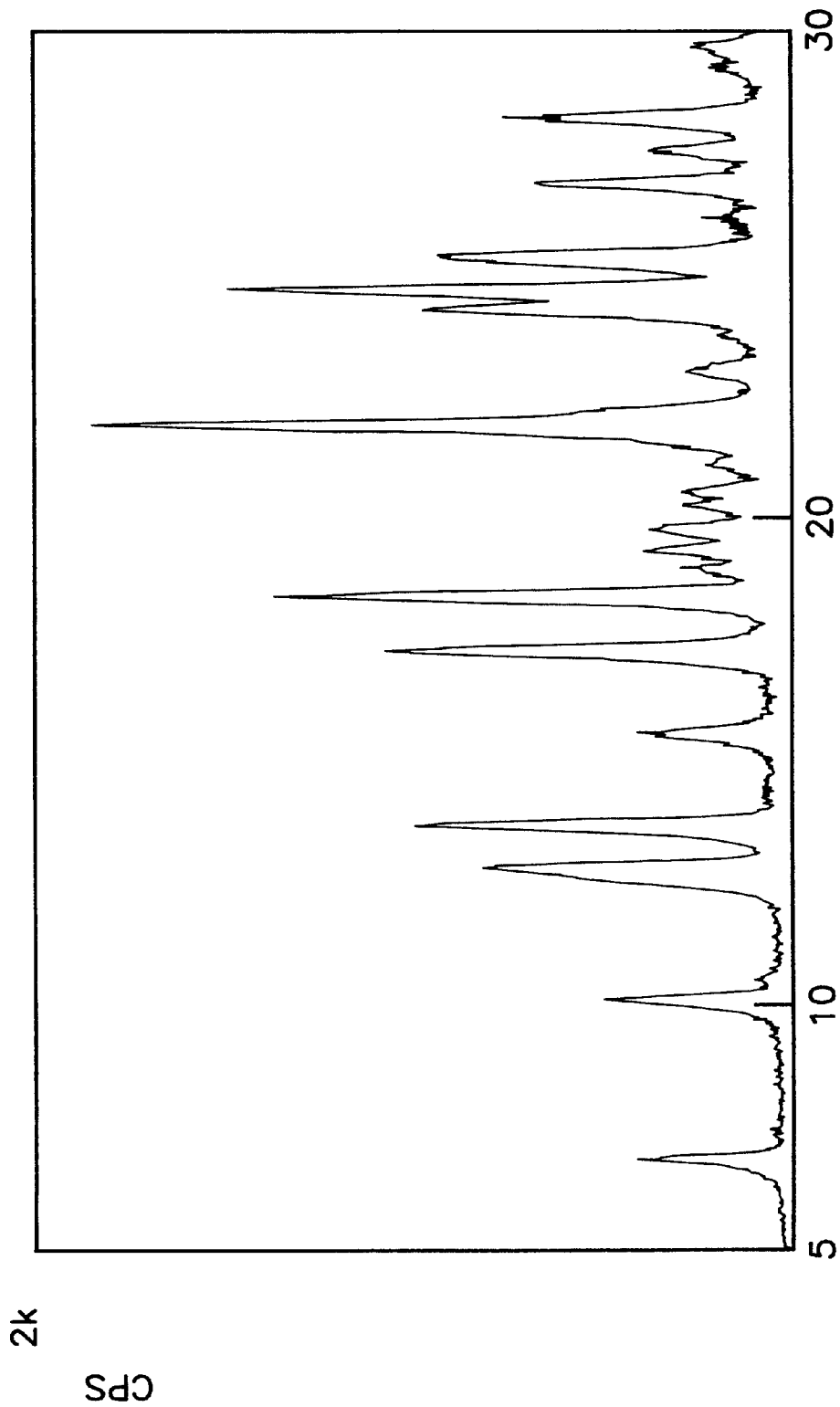
FIG. 25 is clear powder X-ray diffraction pattern of the polymorph (V).
Figure 26:
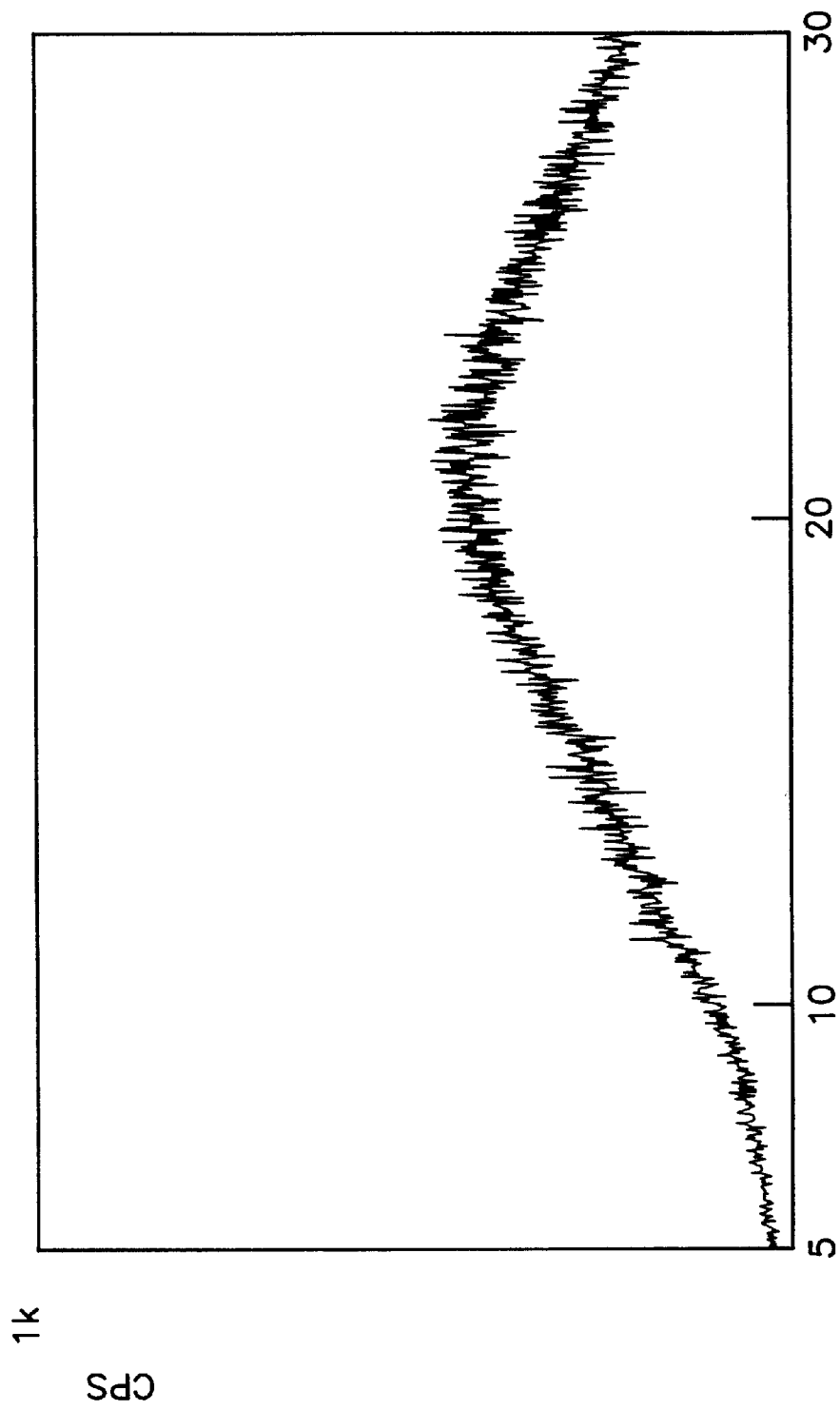
FIG. 26 is clear powder X-ray diffraction pattern of the Amorphous form.
Figure 27:
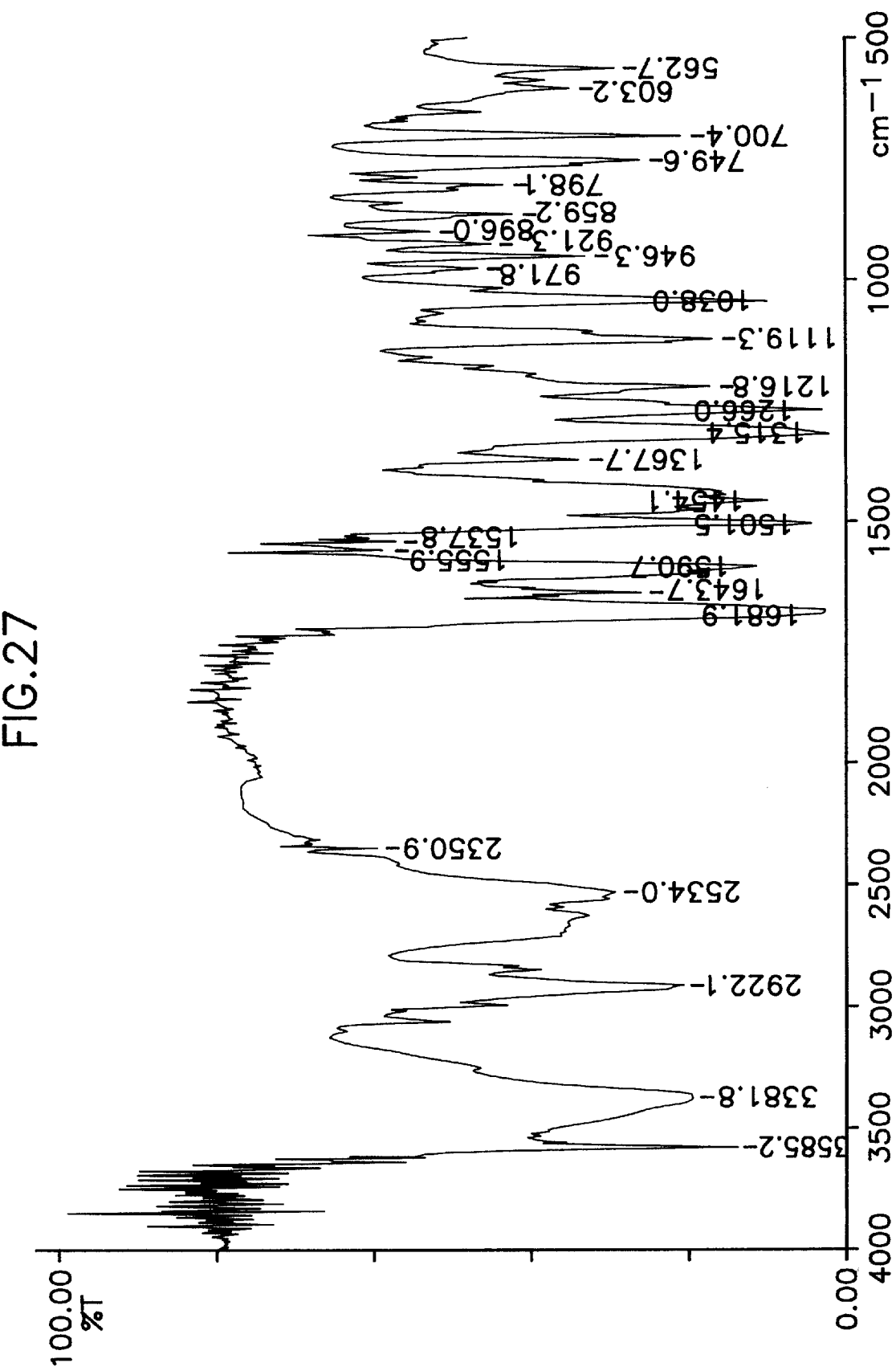
FIG. 27 is clear infrared absorption in potassium bromide of the polymorph (I).
Figure 28:
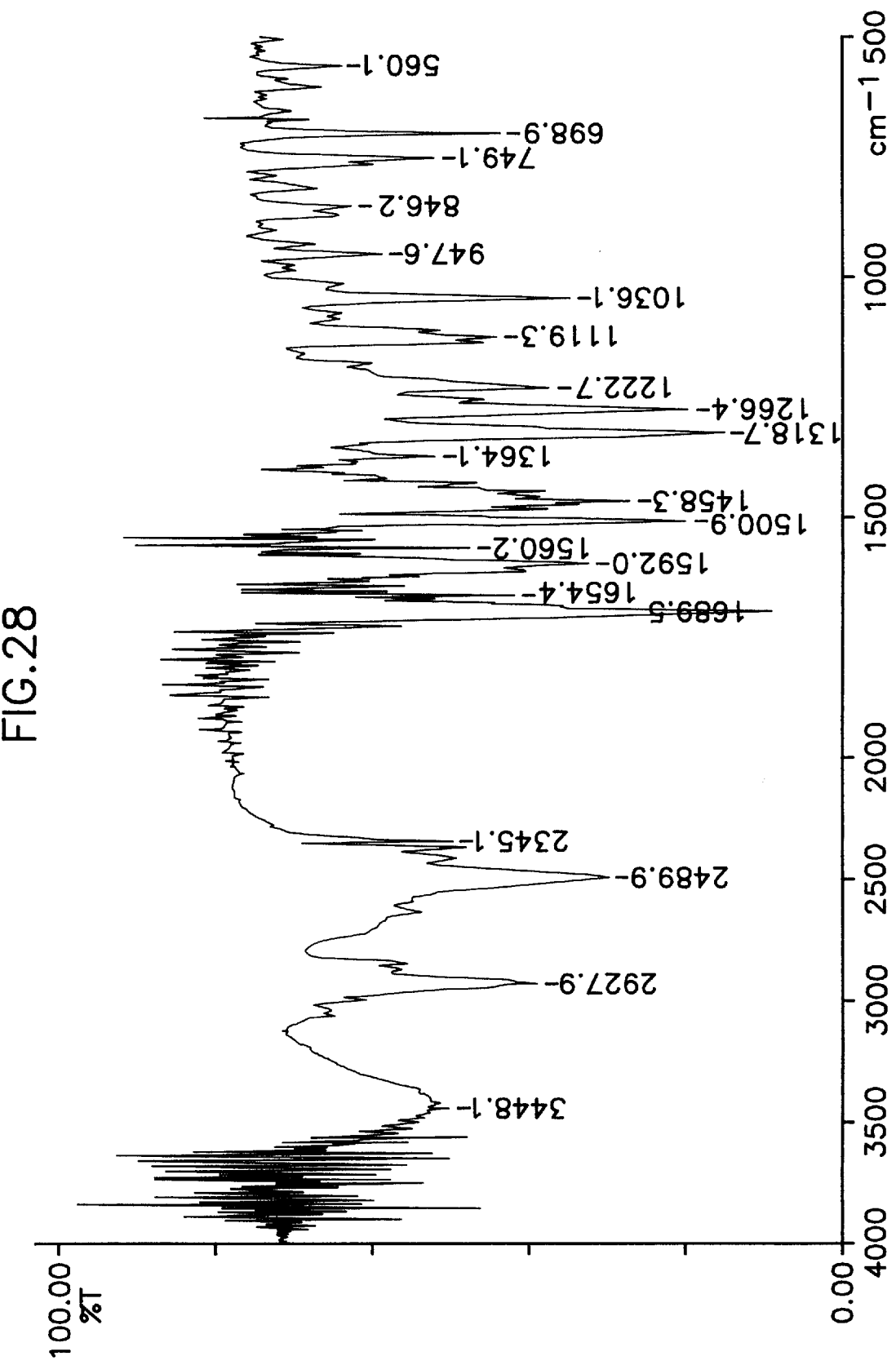
FIG. 28 is clear infrared absorption in potassium bromide of the polymorph (II).
Figure 29:
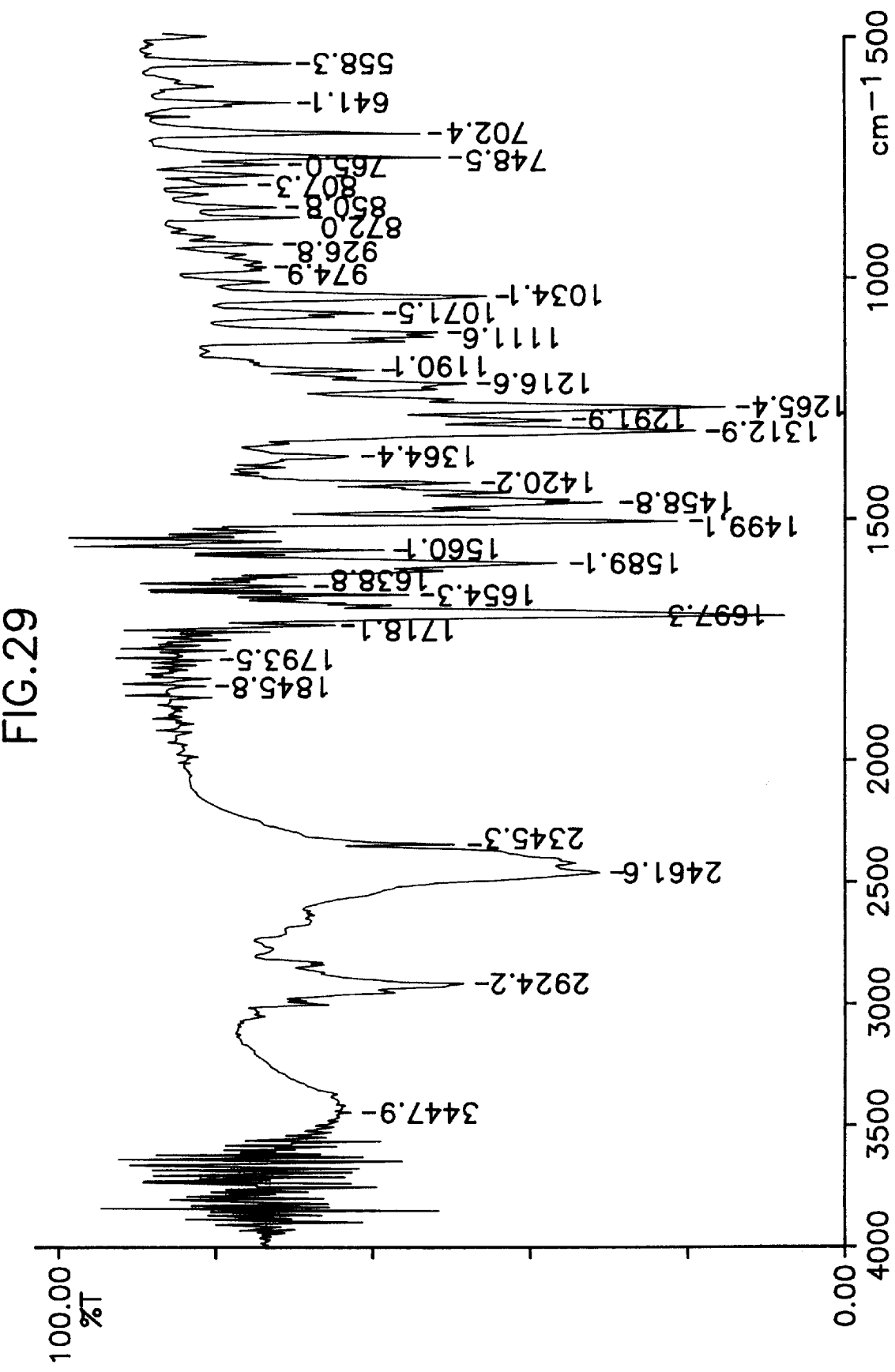
FIG. 29 is clear infrared absorption in potassium bromide of the polymorph (III).
Figure 30:
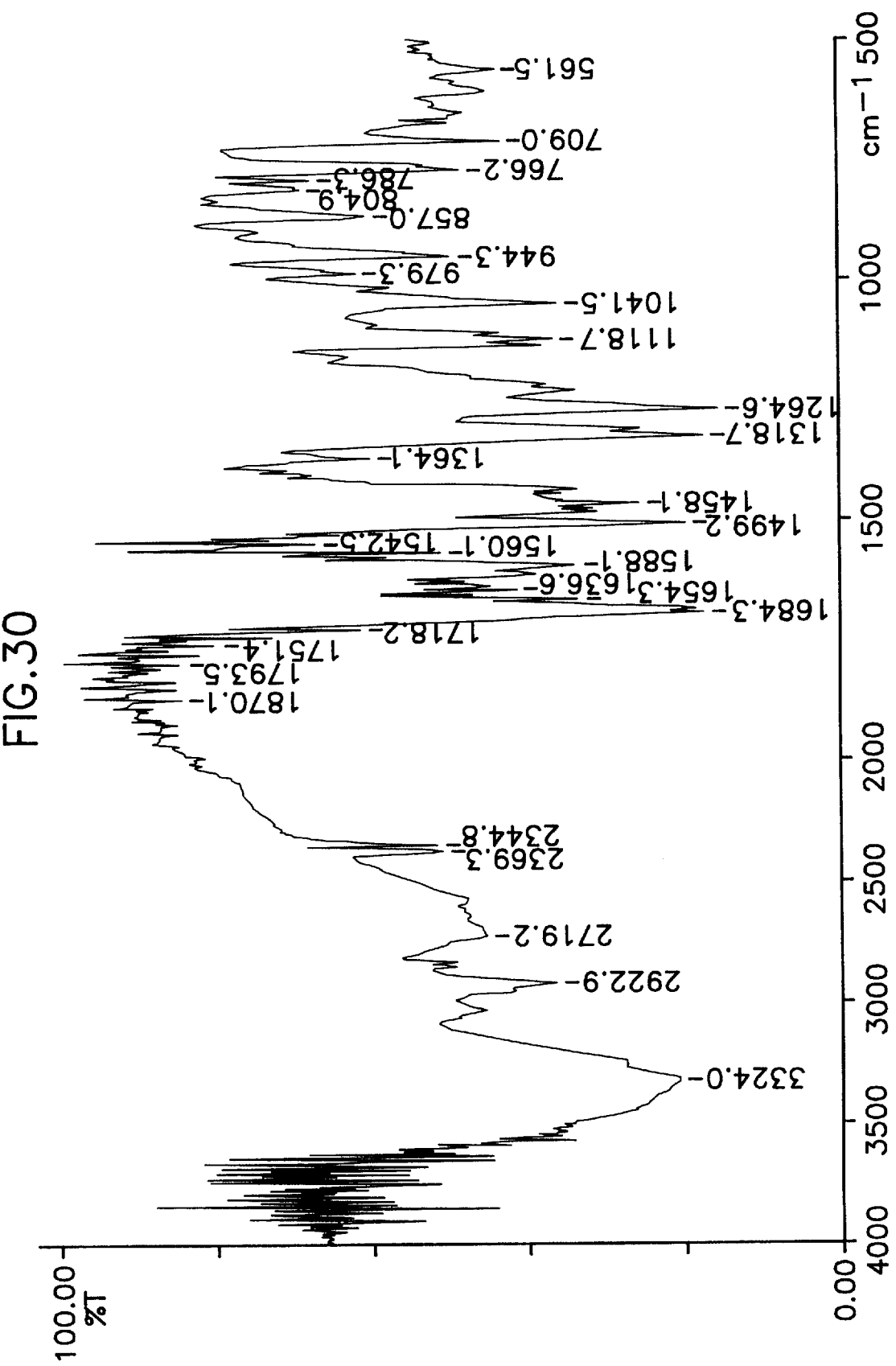
FIG. 30 is clear infrared absorption in potassium bromide of the polymorph (IV).
Figure 31:
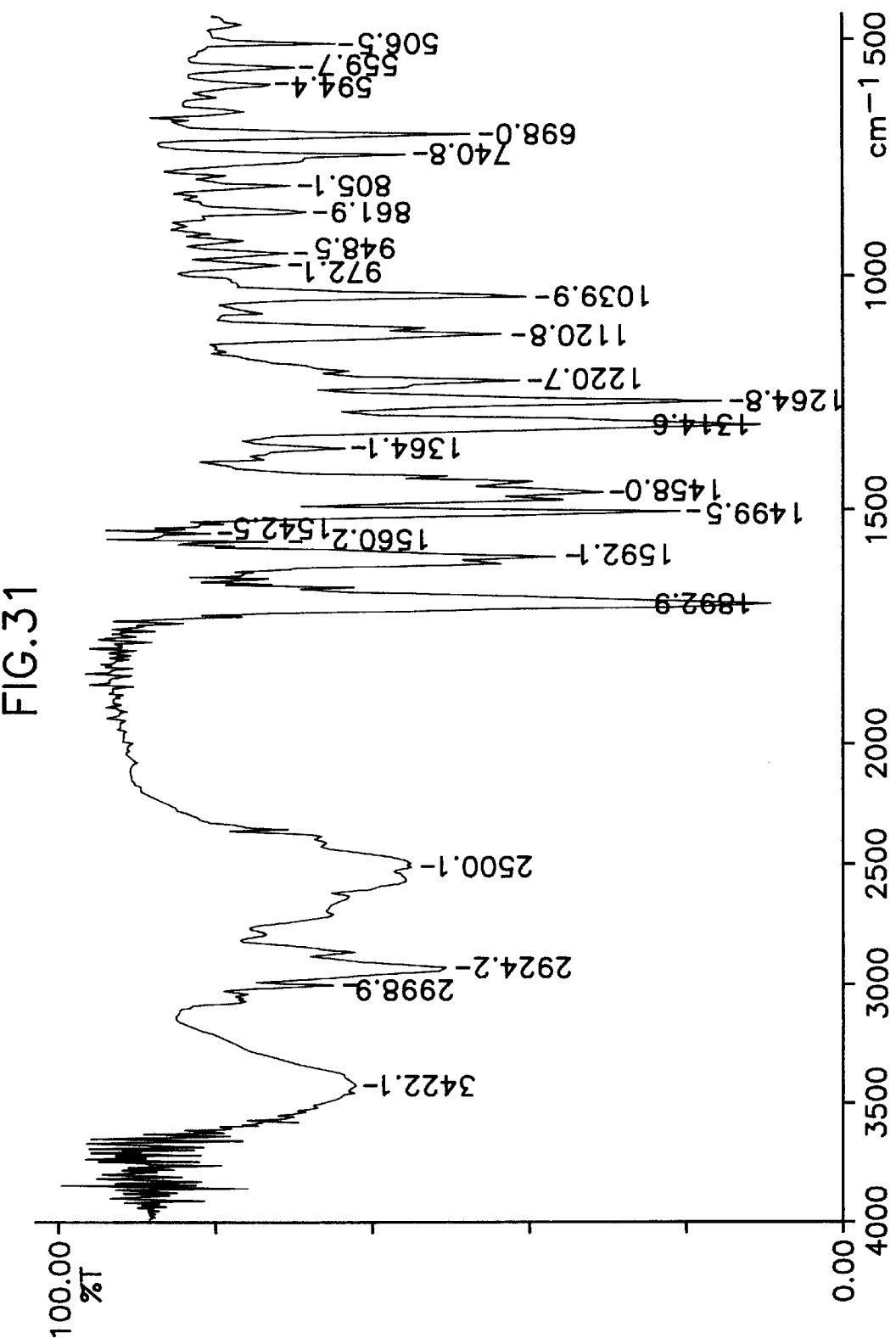
FIG. 31 is clear infrared absorption in potassium bromide of the polymorph (V).
Figure 32:
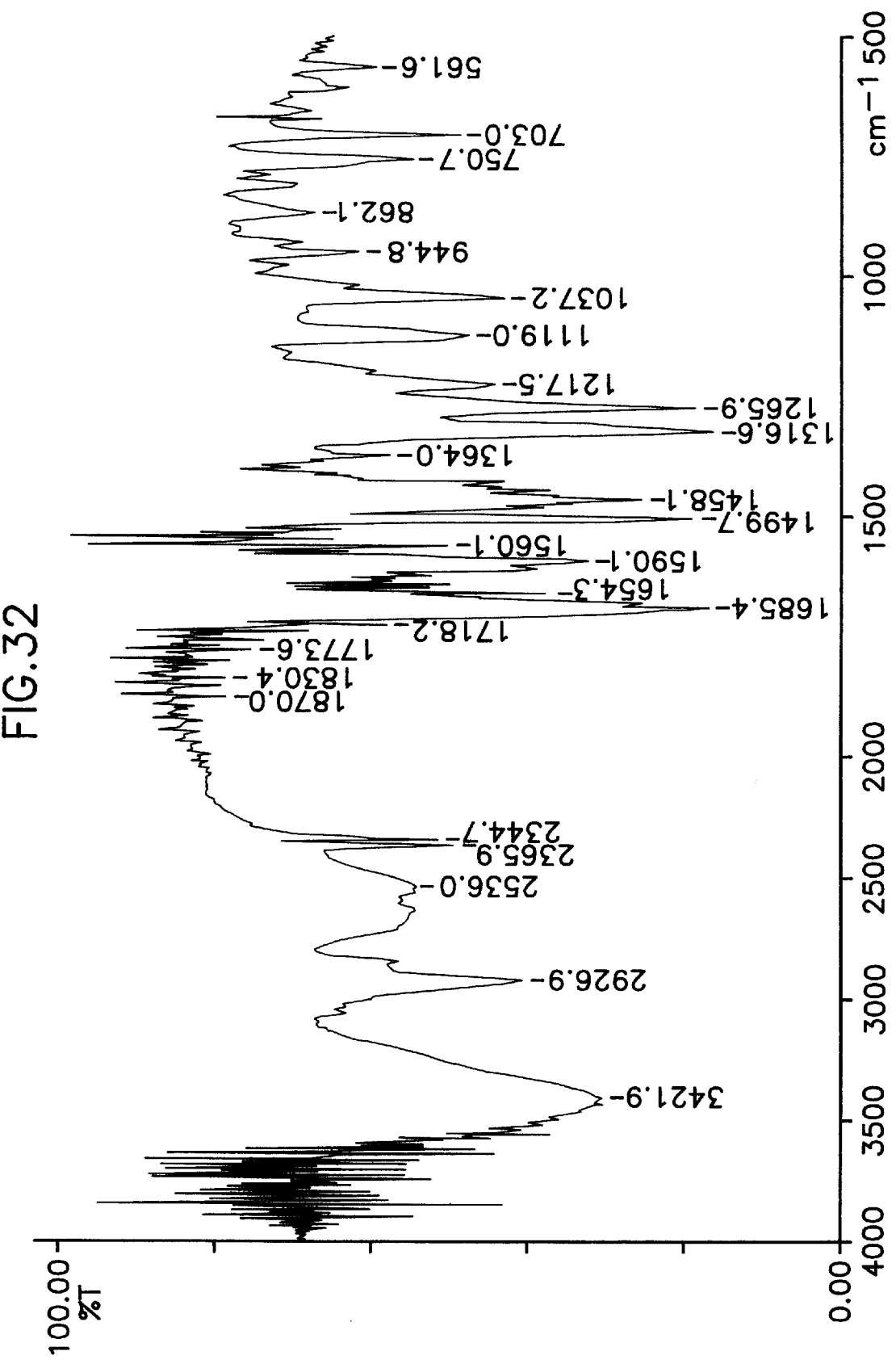
FIG. 32 is clear infrared absorption in potassium bromide of the amorphous form.
Figure 33:
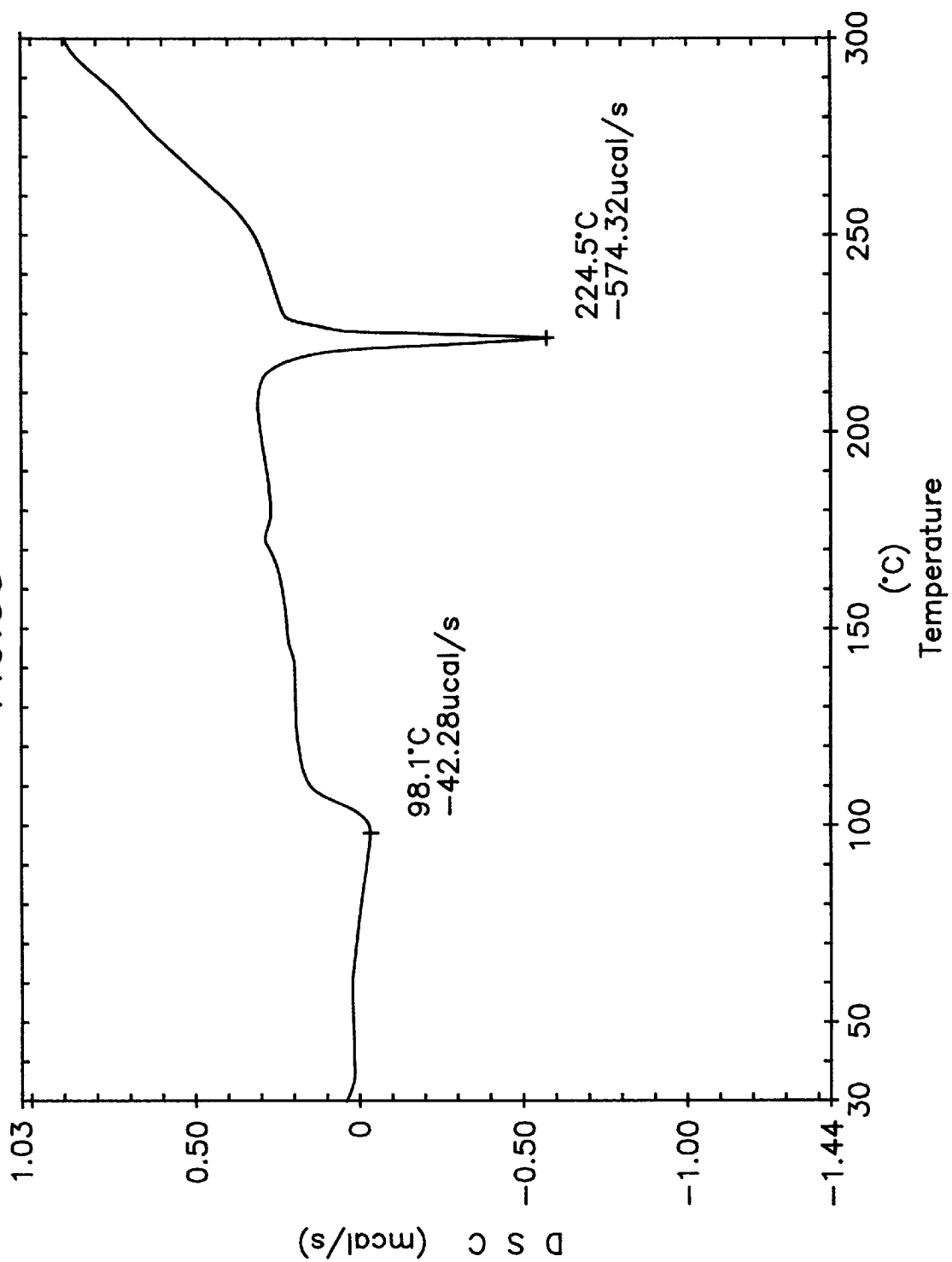
FIG. 33 is clear thermogravimetric and differential thermal analysis (TG-DTA) of the polymorph (I).
Figure 34:
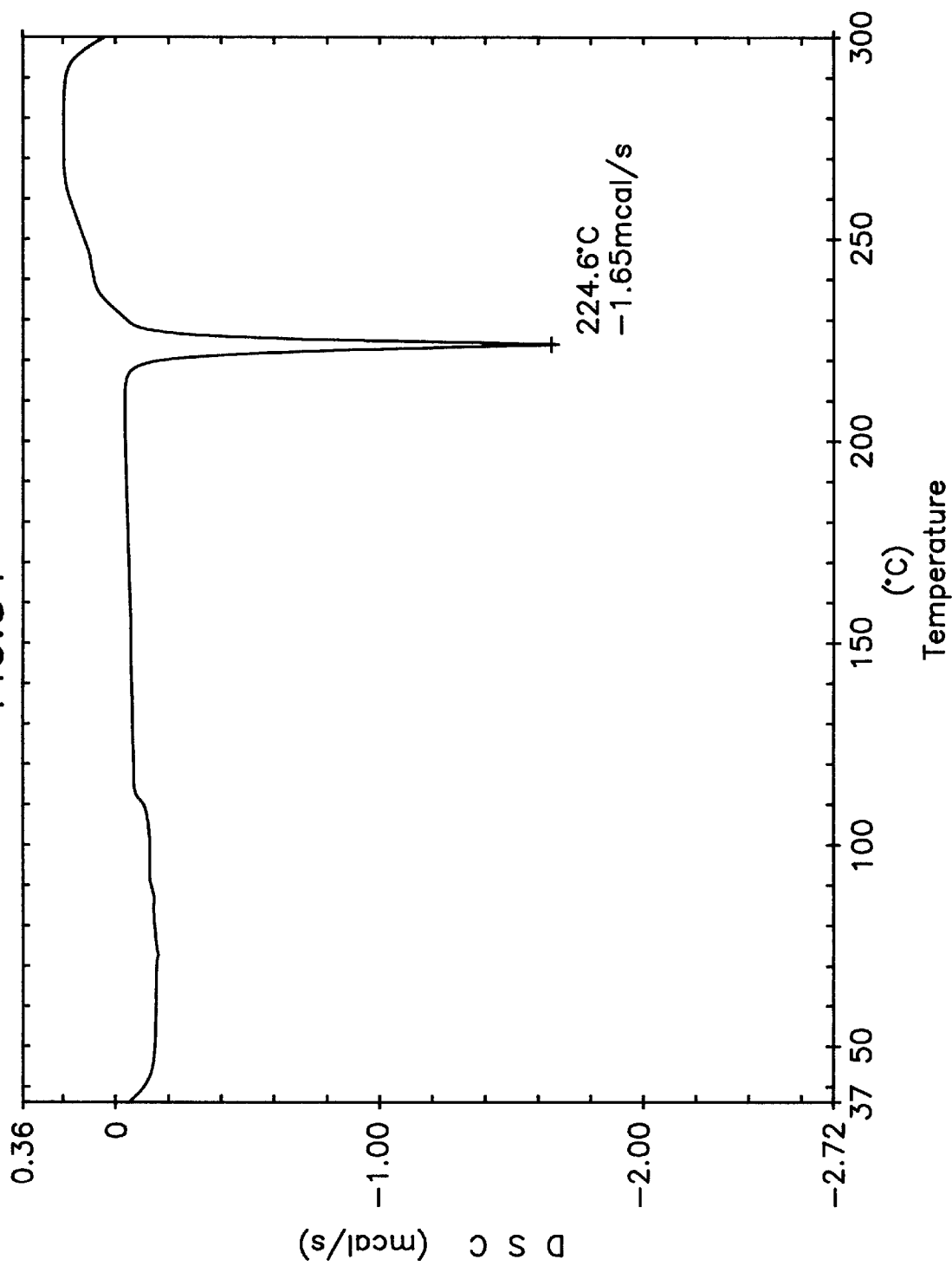
FIG. 34 is clear thermogravimetric and differential thermal analysis (TG-DTA) of the polymorph (II).
Figure 35:
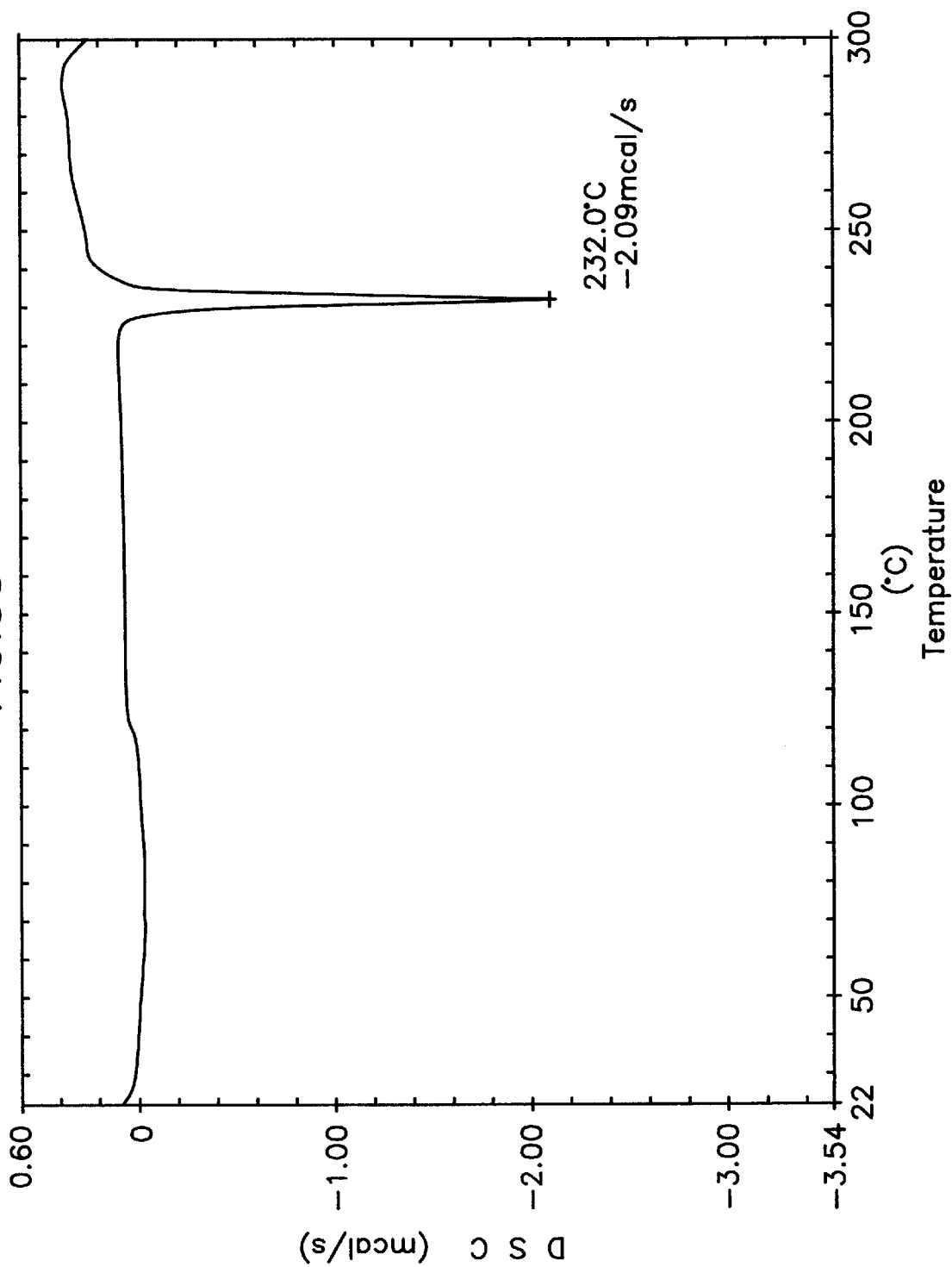
FIG. 35 is clear thermogravimetric and differential thermal analysis (TG-DTA) of the polymorph (III).
Figure 36:
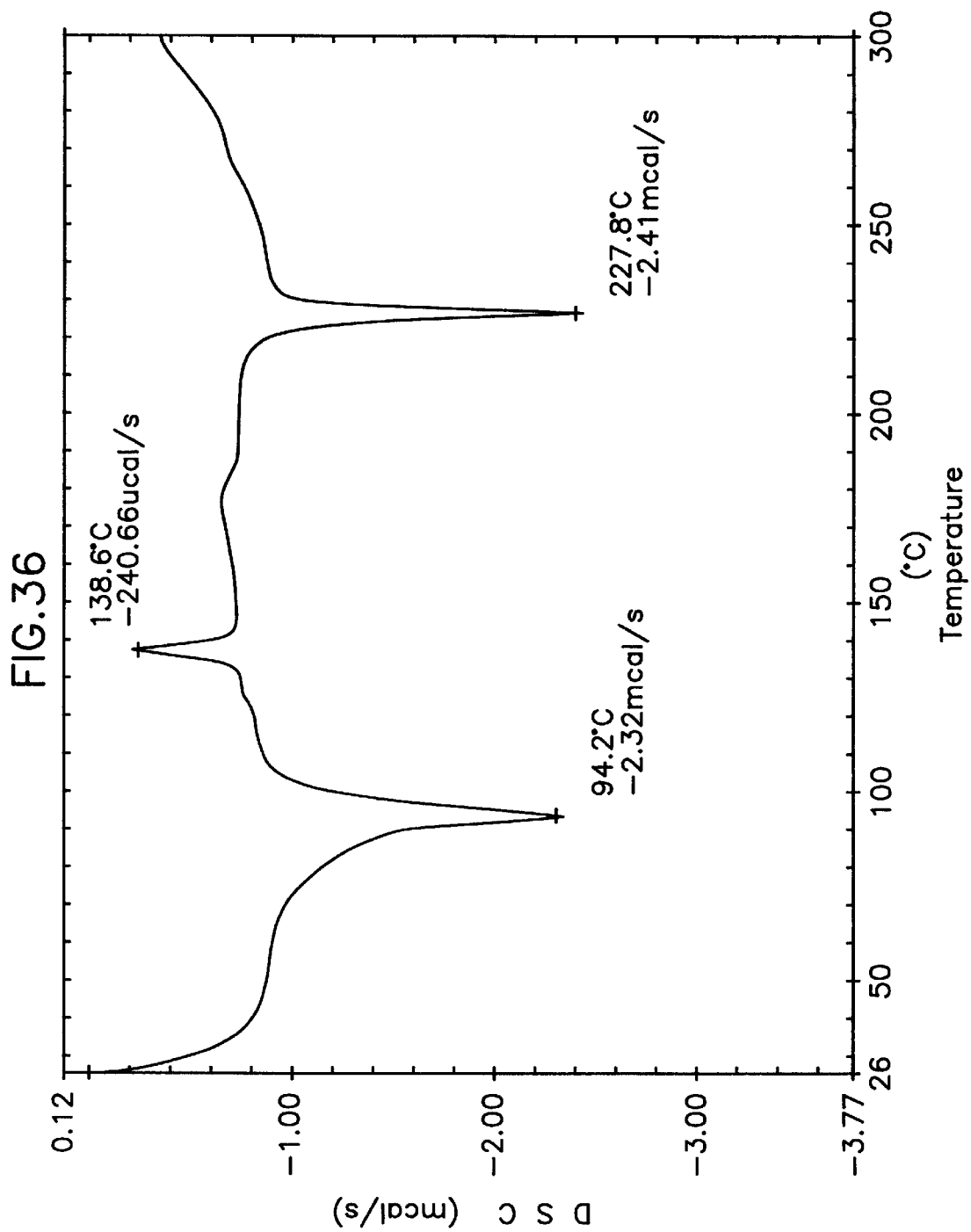
FIG. 36 is clear thermogravimetric and differential thermal analysis (TG-DTA) of the polymorph (IV).
Figure 37:
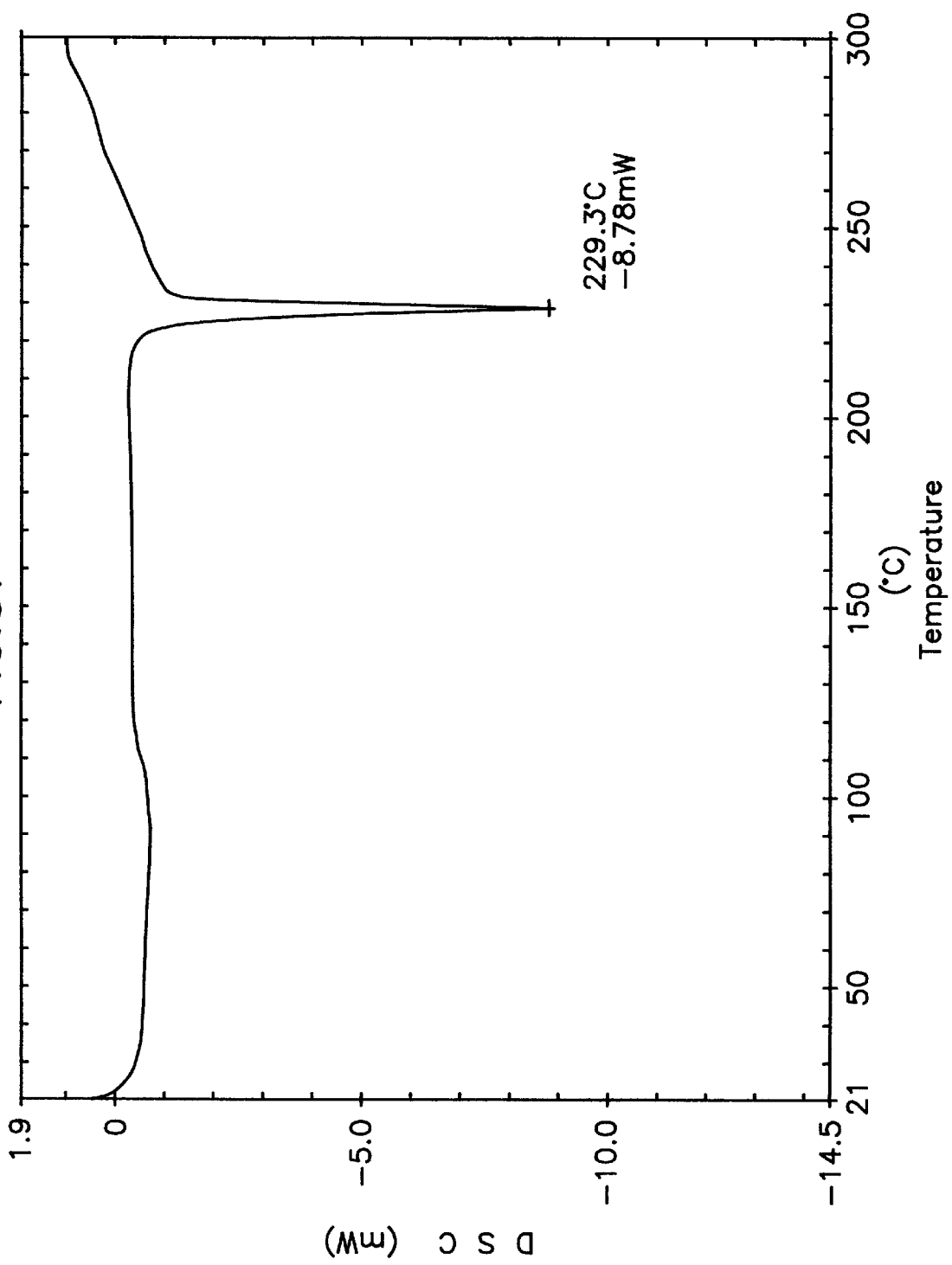
FIG. 37 is clear thermogravimetric and differential thermal analysis (TG-DTA) of the polymorph (V).
Figure 38:
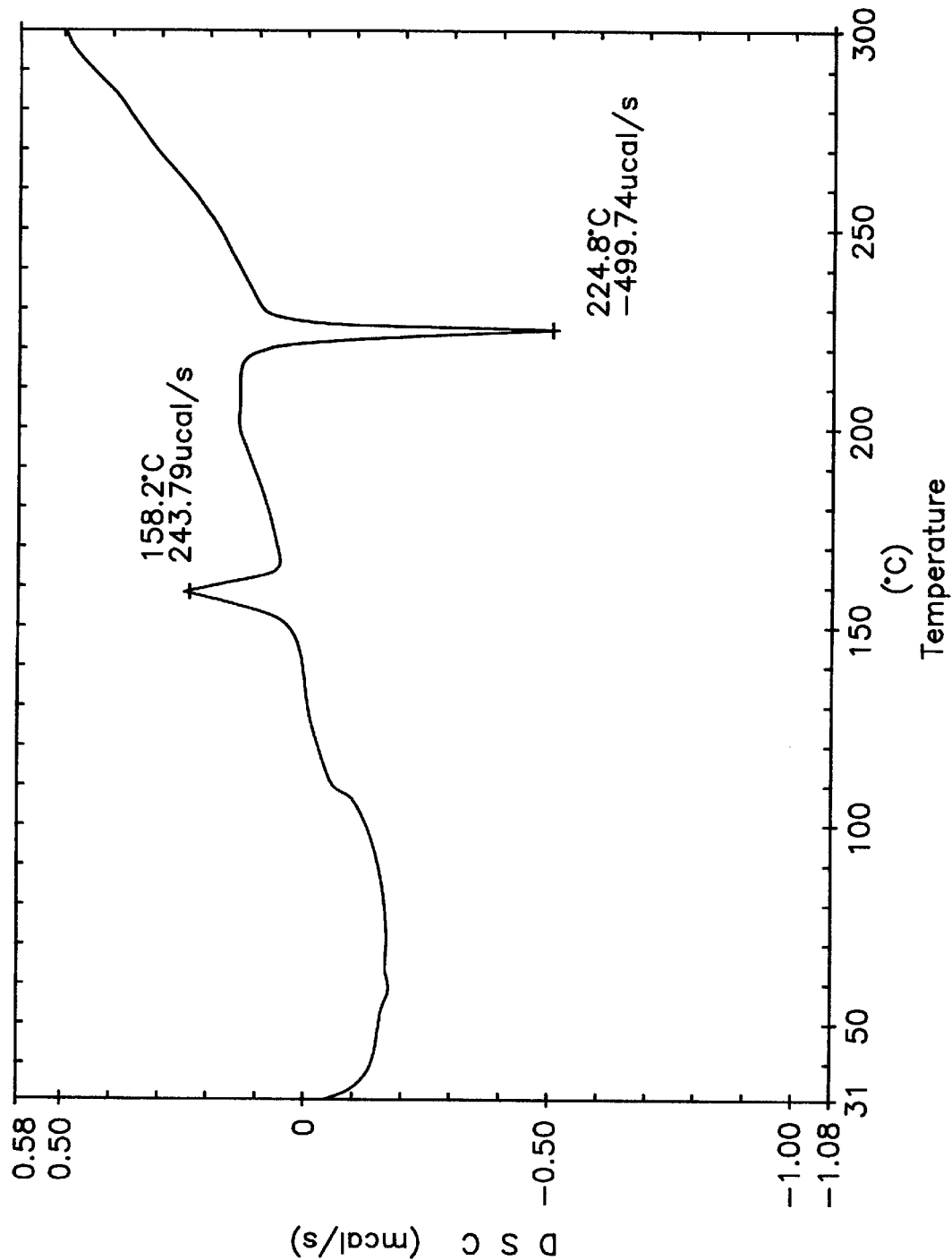
FIG. 38 is clear thermogravimetric and differential thermal analysis (TG-DTA) of the amorphous form.

Results (refer to FIG. 20)

| Relative Humidity | Water contents (%) Polymorph | | | | |
|---|---|---|---|---|---|
| (%) | (I) | (II) | (III) | (IV) | Amorphous |
| Initiation | 4.34 | 0.26 | 0.11 | 12.87 | 2.03 |
| 10.6 | 4.54 | 0.28 | 0.15 | 10.70 | 4.09 |
| 22.2 | 4.75 | 0.29 | 0.14 | 10.60 | 4.78 |
| 31.0 | 5.07 | 0.32 | 0.26 | 10.77 | 5.61 |
| 42.8 | 5.25 | 0.39 | 0.13 | 11.03 | 7.80 |
| 51.0 | 5.38 | 0.43 | 0.15 | 11.28 | 9.29 |
| 61.8 | 5.49 | 0.40 | 0.18 | 11.40 | 12.01 |
| 75.0 | 5.65 | 1.73 | 0.15 | 11.62 | 13.89 |
| 84.0 | 5.64 | 13.70 | 0.16 | 11.72 | 13.74 |
| 93.0 | 5.76 | 13.99 | 0.15 | 11.84 | 14.51 |
| 96.6 | 5.88 | 14.18 | 0.17 | 11.80 | 14.53 |
| 100.0 | 10.37 | 15.93 | 9.71 | 12.26 | 15.44 |

In the above results, the polymorphs (I) to (IV) did not show hygroscopicity until a relative humidity of 96.6%, until 75.0%, until 96.6%, until 100%, respectively. The amorphous Donepezil hydrochloride showed hygroscopicity at and thereafter 10.6%. Those experimental results show that the polymorphs of Donepezil hydrochloride (I) to (IV) have an excellent heat stability and a low hygroscopicity.

We claim:

1. Donepezil hydrochloride, 1-benzyl-4-[(5,6-dimethoxy-1-indanon)-2-yl]methylpiperdine hydrochloride, in the form of polymorphs selected from the group consisting of (II), (IV) and (V), each polymorph being specified by peaks at below shown diffraction degrees with the below shown intensity in terms of I/I$_o$ in x-ray powder diffraction pattern and the below shown absorption peaks in infrared absorption spectra in potassium bromide in terms of reciprocal centimeters:

| Polymorph (II) Peaks in the powder X-ray diffraction pattern are: | |
|---|---|
| Diffraction angles (2θ, °) | Intensity (I/I$_o$) |
| 10.10 | 76 |
| 12.64 | 14 |
| 15.74 | 85 |
| 15.82 | 86 |
| 16.20 | 100 |
| 16.46 | 87 |
| 17.40 | 50 |
| 17.50 | 48 |
| 17.88 | 31 |
| 18.36 | 28 |
| 18.58 | 51 |
| 18.66 | 46 |
| 19.48 | 42 |
| 20.18 | 81 |
| 20.80 | 36 |
| 22.26 | 45 |
| 23.38 | 86 |
| 23.52 | 59 |
| 24.06 | 34 |
| 24.32 | 55 |
| 25.14 | 44 |
| 25.44 | 50 |
| 25.72 | 39 |
| 25.96 | 35 |
| 26.14 | 25 |
| 28.06 | 25 |
| 28.20 | 34 |
| 28.38 | 34 |

Wave numbers (cm$^{-1}$) if infrared absorption spectra in potassium bromide are:

560.1, 698.9, 749.1, 846.2, 947.6, 1036.1, 1119.3, 1222.7, 1266.4, 1318.7, 1364.1, 1458.3, 1500.9, 1522.3, 1534.0, 1542.6, 1560.2, 1570.3, 1592.0, 1637.0, 1647.9, 1654.4, 1689.5, 1718.3, 1734.7, 1751.7, 1773.9, 1793.8, 1830.7, 1846.0, 1870.1, 2354.1, 2489.9, 2927.9, 3448.1 cm$^{-1}$

Polymorph (IV)
Peaks in the powder X-ray diffraction pattern are:

| Diffraction angles (2θ, °) | Intensity (I/I$_o$) |
|---|---|
| 9.64 | 11 |
| 10.92 | 11 |
| 12.46 | 63 |
| 12.72 | 17 |
| 13.86 | 27 |
| 14.42 | 12 |
| 17.36 | 100 |
| 18.54 | 39 |
| 19.90 | 37 |
| 21.18 | 35 |
| 21.74 | 39 |
| 22.48 | 60 |
| 22.96 | 36 |
| 24.10 | 17 |
| 25.28 | 70 |
| 28.00 | 27 |
| 28.50 | 27 |

Wave numbers (cm$^{-1}$) of infrared absorption spectra in potassium bromide are:
561.5, 709.0, 766.2, 786.3, 804.9, 857.0, 944.3, 979.3, 1041.5,
1118.7, 1264.6, 1318.7, 1364.1, 1458.1, 1499.2, 1542.5, 1560.1,
1588.1, 1636.6, 1647.8, 1654.3, 1684.3, 1718.2, 1734.4, 1751.4,
1773.7, 1793.5, 1830.5, 1845.8, 1870.1, 2344.8, 2369.3, 2719.2,
2922.9, 3324.0 cm$^{-1}$ Polymorph (V)

| Diffraction angles (2θ, °) | Intensity (I/I$_o$) |
|---|---|
| 6.58 | 7 |
| 6.86 | 27 |
| 10.12 | 32 |
| 12.54 | 33 |
| 12.90 | 43 |
| 13.64 | 64 |
| 15.58 | 27 |
| 17.22 | 69 |
| 18.44 | 72 |
| 18.96 | 19 |
| 19.30 | 25 |
| 19.64 | 19 |
| 19.74 | 25 |
| 20.30 | 19 |
| 20.46 | 17 |
| 21.10 | 15 |
| 21.96 | 100 |
| 22.24 | 32 |
| 24.22 | 63 |
| 24.66 | 96 |
| 25.36 | 60 |
| 26.14 | 15 |
| 26.82 | 44 |
| 27.52 | 24 |
| 27.96 | 15 |
| 28.20 | 49 |
| 29.58 | 13 |
| 29.66 | 17 |
| 29.76 | 17 |

Wave numbers (cm$^{-1}$) of infrared absorption spectra in potassium bromide are:
506.5, 559.7, 594.4, 698.0, 740.8, 805.1, 861.9, 948.5, 972.1,
1039.9, 1120.8, 1220.7, 1264.8, 1314.6, 1364.1, 1458.0, 1499.5,
1542.5, 1560.2, 1592.1, 1692.9, 2500.1, 2924.2, 2998.9, 3422.1, cm$^{-1}$.

2. A process for producing the polymorph (II) of Donepezil hydrochloride as defined in claim 1, which comprises the steps of dissolving Donepezil hydrochloride in ethanol and adding diethyl ether or isopropyl ether to the solution.

3. A process for producing the polymorph (II) of Donepezil hydrochloride as defined in claim 1, which comprises the steps of dissolving Donepezil hydrochloride in ethanol, adding isopropyl ether to the solution, stirring the mixture for 10 to 30 minutes after having precipitated and filtrating the crystalline precipitates.

4. A process for producing the polymorph (II) of Donepezil hydrochloride as defined in claim 1, which comprises the steps of dissolving Donepezil and hydrochloric acid or hydrogen chloride in ethanol and adding diethyl ether to the solution.

5. A process for producing the polymorph (II) of Donepezil hydrochloride as defined in claim 1, which comprises the steps of dissolving Donepezil in ethanol, adding hydrochloric acid or hydrogen chloride to the solution and concentrating the mixture.

6. A process for producing the polymorph (II) of Donepezil hydrochloride as defined in claim 1, which comprises the steps of dissolving Donepezil in ethanol, adding hydrochloric acid or hydrogen chloride to the solution and adding isopropyl ether to the mixture.

7. The process as claimed in claim 6, which further comprises filtrating crystalline precipitates after having stirred for 10 to 60 minutes.

8. A process for producing the polymorph (IV) of Donepezil hydrochloride as defined in claim 1, which comprises the step of humidifying the polymorph (II) as defined in claim 1.

9. A process for producing the polymorph (II) of Donepezil hydrochloride as defined in claim 1, which comprises the steps of dissolving Donepezil in ethanol, adding hydrochloric acid or hydrogen chloride to the solution and adding tert-butyl methyl ether successively.

10. A process for producing the polymorph (II) of Donepezil hydrochloride as defined in claim 1, which comprises the steps of dissolving Donepezil in isopropyl alcohol or in methylene chloride and adding hydrochloric acid or hydrogen chloride to the solution.

11. A process for producing the polymorph (II) of Donepezil hydrochloride as defined in claim 1, which comprises the steps of dissolving Donepezil in acetone, adding hydrochloric acid or hydrogen chloride to the solution and filtrating the crystalline precipitates within 30 minuets from the separation of crystals.

12. A process for producing the polymorph (II) of Donepezil hydrochloride as defined in claim 1, which comprises the steps of dissolving Donepezil hydrochloride in ethanol and adding tert-butyl methyl ether to the solution at temperature in the range of 10 to 30° C.

13. A process for producing the polymorph (II) of Donepezil hydrochloride as defined in claim 1, which comprises the steps of dissolving Donepezil hydrochloride in ethanol and adding this solution to diisopropyl ether.

14. A process for producing the polymorph (II) of Donepezil hydrochloride as defined in claim 1, which comprises the steps of dissolving Donepezil hydrochloride in methylene chloride and adding tert-butyl methyl ether to the solution.

15. A process for producing the polymorph (II) of Donepezil hydrochloride as defined in claim 1, which comprises the step of drying the polymorph (I) or amorphous form of Donepezil hydrochloride.

16. A process for producing the polymorph (IV) of Donepezil hydrochloride as defined in claim 1, which comprises the step of humidifying the polymorph (II) as defined in claim 1.

17. A process for producing the polymorph (IV) of Donepezil hydrochloride as defined in claim 1, which comprises the steps of dissolving Donepezil in water with or without tetrahydrofuran and adding hydrochloric acid or hydrogen chloride to the solution.

18. A process for producing the polymorph (IV) of Donepezil hydrochloride as defined in claim 1, which comprises the steps of dissolving Donepezil in hydrochloric acid and adding tetrahydrofuran to the solution.

19. A process for producing the polymorph (IV) of Donepezil hydrochloride as defined in claim 1, which comprises the steps of dissolving Donepezil in toluene and adding hydrochloric acid to the solution.

20. A process for producing the polymorph (IV) of Donepezil hydrochloride as defined in claim 1, which comprises the steps of dissolving Donepezil in n-hexane and adding hydrochloric acid to the solution.

21. A process for producing the polymorph (IV) of Donepezil hydrochloride as defined in claim 1, which comprises the step of crystallizing Donepezil in a mixture of methanol and hydrochloric acid.

22. A process for producing the polymorph (IV) of Donepezil hydrochloride as defined in claim 1, which comprises the step of crystallizing Donepezil hydrochloride from water.

23. A process for producing the polymorph (IV) of Donepezil hydrochloride as defined in claim 1, which comprises the step of humidifying the amorphous form of Donepezil hydrochloride.

24. A process for producing the polymorph (IV) of Donepezil hydrochloride as defined in claim 1, which comprises the step of humidifying the polymorph (II) of Donepezil hydrochloride.

25. A process for producing the polymorph (V) of Donepezil hydrochloride as defined in claim 1, which comprises the step of drying the polymorph (IV) of Donepezil hydrochloride.

26. A method for treating a disease accompanied by acetylcholinesterase activity which comprises administering to a human patient in need thereof a pharmacologically effective amount of the Donepezil hydrochloride in the form of a polymorph as defined in claim 1 for inhibiting the acetylcholinesterase activity.

27. The method as claimed in claim 1, in which the disease is senile dementia.

28. The method as claimed in claim 1, in which the disease is senile dementia of the Alzheimer type.

29. A therapeutical composition which comprises a pharmacologically effective amount of Donepezil hydrochloride in the form of polymorph as defined in claim 1 and a pharmaceutically acceptable carrier.

30. The Donepezil hydrochloride as claimed in claim 1, which is in the form of polymorph (II).

31. The Donepezil hydrochloride as claimed in claim 1, which is in the form of polymorph (III).

32. The Donepezil hydrochloride as claimed in claim 1, which is in the form of polymorph (IV).

33. The Donepezil hydrochloride as claimed in claim 1, which is in the form of polymorph (V).

* * * * *

UNITED STATES PATENT AND TRADEMARK OFFICE
CERTIFICATE OF CORRECTION

PATENT NO.   : 5,985,864
DATED        : November 16, 1999
INVENTOR(S)  : Akio Imai et al.

It is certified that error appears in the above-identified patent and that said Letters Patent is hereby corrected as shown below:

Column 34,
Lines 26-27, delete claim 31.

Signed and Sealed this

Sixth Day of July, 2004

JON W. DUDAS
*Acting Director of the United States Patent and Trademark Office*

Disclaimer

5,985,864—Akio Imai; Hideaki Watanabe; Takashi Kajima; Yasushi Ishihama; Akiyo Ohtsuka; Tomohide Tanaka; Yukio Narabu, all of Ibaraki, Japan. POLYMORPHS OF DONEPEZIL HYDROCHLORIDE AND PROCESS OF PRODUCTION. Patent dated November 16, 1999. Disclaimer filed May 1, 2007 by Assignee, Elsai, Co., Ltd.

Hereby enters this disclaimer to claims 1-30, 32 and 33, of said patent.

*(Official Gazette, June 19, 2007)*